(12) United States Patent
Alvarez et al.

(10) Patent No.: US 9,080,963 B2
(45) Date of Patent: Jul. 14, 2015

(54) DEVICES AND METHODS FOR COLLECTION OF DATA

(71) Applicant: ITEL Laboratories, Inc., Jacksonville, FL (US)

(72) Inventors: Steve M. Alvarez, Jacksonville, FL (US); Sergio Passalacqua, St. Johns, FL (US); Raymond Darrell Jester, Jacksonville, FL (US); Lonnie Dale Romine, Jacksonville, FL (US); Henrik Georg Stahre, Jacksonville, FL (US); Carl Jonas Peter Schonning, Jacksonville, FL (US); Percy F. Shadwell, Jr., Jacksonville, FL (US)

(73) Assignee: ITEL LABORATORIES, INC., Jacksonville, FL (US)

( * ) Notice: Subject to any disclaimer, the term of this patent is extended or adjusted under 35 U.S.C. 154(b) by 0 days.

(21) Appl. No.: 14/538,722

(22) Filed: Nov. 11, 2014

(65) Prior Publication Data

US 2015/0134285 A1    May 14, 2015

Related U.S. Application Data

(60) Provisional application No. 61/903,264, filed on Nov. 12, 2013.

(51) Int. Cl.
| | |
|---|---|
| *G01N 21/359* | (2014.01) |
| *G01F 17/00* | (2006.01) |
| *G06T 7/00* | (2006.01) |
| *G06T 17/00* | (2006.01) |
| *G01B 11/00* | (2006.01) |

(52) U.S. Cl.
CPC .............. *G01N 21/359* (2013.01); *G01F 17/00* (2013.01); *G06T 7/00* (2013.01); *G06T 17/00* (2013.01); *G01B 11/00* (2013.01)

(58) Field of Classification Search
CPC ........... G06T 7/00; G06T 17/00; G01F 17/00; G01B 11/00
USPC ........ 702/81; 717/174, 178; 705/7.12, 28, 25, 705/321, 7.14, 7.25; 455/410, 418, 420
See application file for complete search history.

(56) References Cited

U.S. PATENT DOCUMENTS

| | | | |
|---|---|---|---|
| 6,011,550 A | * | 1/2000 | Capps et al. ................... 715/788 |
| 7,080,080 B1 | | 7/2006 | Miller |

(Continued)

FOREIGN PATENT DOCUMENTS

CN    102722840 A * 10/2012

OTHER PUBLICATIONS

International Search Report, PCT/US2014/065009, 4 pages (Mar. 26, 2015).

(Continued)

*Primary Examiner* — Carol S Tsai
(74) *Attorney, Agent, or Firm* — Choate, Hall & Stewart LLP

(57) ABSTRACT

Devices and methods for remotely collecting data for the assessment of value and/or like, kind, and quality are provided, including a mobile device equipped with an application configured to enable collection of data; the data acquired using the device are received by a service provider; and following the assessment transmitting of the assessment analysis by the service provide to the display of the mobile device of the user.

13 Claims, 36 Drawing Sheets

(56) References Cited

U.S. PATENT DOCUMENTS

| | | |
|---|---|---|
| 7,747,460 B2 | 6/2010 | Vandrilla |
| 7,805,382 B2 * | 9/2010 | Rosen et al. ................. 705/321 |
| 7,853,470 B2 * | 12/2010 | Sonnleithner et al. ....... 705/7.12 |
| 7,902,507 B1 * | 3/2011 | Garvey et al. ................. 250/330 |
| 8,428,520 B2 * | 4/2013 | Kobayashi et al. ........ 455/67.13 |
| 8,929,860 B2 * | 1/2015 | Ye et al. ....................... 455/410 |
| 2003/0213315 A1 | 11/2003 | Charters et al. |
| 2004/0236620 A1 * | 11/2004 | Chauhan et al. ................. 705/9 |
| 2006/0026145 A1 | 2/2006 | Beringer et al. |
| 2006/0229896 A1 * | 10/2006 | Rosen et al. ....................... 705/1 |
| 2007/0263968 A1 * | 11/2007 | Lath .............................. 385/120 |
| 2008/0004993 A1 * | 1/2008 | Horspool et al. ............... 705/28 |
| 2010/0267521 A1 * | 10/2010 | Matsunaga ....................... 482/9 |
| 2011/0213718 A1 | 9/2011 | Leger |
| 2012/0311053 A1 | 12/2012 | Labrie et al. |
| 2013/0239104 A1 * | 9/2013 | Savant et al. .................. 717/178 |
| 2013/0268416 A1 | 10/2013 | Sandow |
| 2014/0025433 A1 | 1/2014 | Leger |
| 2014/0138435 A1 * | 5/2014 | Khalid .......................... 235/380 |
| 2014/0270480 A1 * | 9/2014 | Boardman et al. ............ 382/154 |

OTHER PUBLICATIONS

Written Opinion, PCT/US2014/065009, 7 pages (Mar. 26, 2015).

* cited by examiner

B

C

DEVICES AND METHODS FOR COLLECTION OF DATA

CROSS-REFERENCE TO RELATED APPLICATION

This patent application claims priority to and the benefit of, U.S. provisional patent application Ser. No. 61/903,264, filed on Nov. 12, 2013, the entire contents of which are herein incorporated by reference.

BACKGROUND

Property owners, installers, builders, and insurance claim representatives have long been frustrated with the expense and difficulty of onsite analysis for product replacement and/or new installation. The expense and difficulty is particularly acute for building materials used in the construction trades, such as flooring, carpet, siding, roofing, etc. because of a desire to match or find similar like, kind or quality from diverse types and varieties of products. Replacement typically requires that someone collect samples at a client site and send those samples to a lab for analysis. During this evaluation, a client must wait for results. Thus, there is a need in the art for a more efficient approach for performing insurance claims adjustments involving building materials.

SUMMARY

Among other things, the present disclosure provides devices and methods for remote data collection for analysis of building materials. In general, a method for remote analysis of building materials products is provided. Some embodiments of the present disclosure obviate a need for onsite collection of material samples for off-site analysis. In some embodiments, methods for on-site assignment of value and/or like, kind, and quality assessment, include steps of providing, for access by a remote, mobile client computing device, an interactive program configured to enable collection of data from the remote client computing device for assignment of value assessment and/or like, kind, and quality assessment, wherein the interactive program is configured to display to a user a sequence of screens on the remote computing device prompting entry of user input about a building material sample; receiving, by a processor of a service provider computing device, over a network, from the remote computing device, the user input about the sample; and transmitting, by the processor of the service provider computing device, to the remote client computing device, results of an analysis for assignment of value and/or like, kind, and quality assessment, for display to the user.

In some embodiments, a user input may be at least one photo of a sample. In some aspects an interactive program is configured with a photo display to prompt the user to acquire a photo of a sample using a mobile client computing device. In some embodiments, an interactive program is configured to manipulate a photo of a sample before a receiving step when a user accesses a prompt displayed on at least one screen for photo management.

In some embodiments, a user input may be entry at a sequence of screens prompting one or more graphical prompts, for example photographic, schematic, pictorial prompts or combinations thereof instructing a user in acquiring a photo of a sample using a mobile client computing device.

In various embodiments, an interactive program is further configured to prompt a user to acquire additional photos for a user input before a receiving step. In some embodiments, an interactive program is further configured to prompt a user to delete an at least one photo from a user input before a receiving step.

According to some embodiments, a user input comprises at least one piece of information indicative of a sample, for example, identification of a corresponding user, identification of a corresponding site, identification of a sample number, etc. or combinations thereof.

In some embodiments, an at least one piece of information indicative of a sample comprises a characteristic corresponding to a building material sample. In some embodiments, a characteristic corresponding to a building material sample is a measurement of the building material sample, a type of material of the building material sample, or combinations thereof. In some embodiments, a type of material of the building material sample is carpet, wood, vinyl, laminate, tile, siding, roofing, rug, or combinations thereof.

In some embodiments, entry of an at least one piece of information indicative of a sample ensues from a selection by a user from a dynamic list displayed on a remote computing device. In some embodiments, entry of an at least one piece of information indicative of a sample follows one or more prompts displayed on at least one screen presented based on responses provided by a user on one or more preceding screens.

In some embodiments, a dynamic list is displayed as a text box. In some embodiments, a dynamic list is displayed as a dropdown list box. In some embodiments, a dynamic list is displayed as a radio button.

In some embodiments of the present disclosure, a providing step includes identifying whether all required data about a building material sample has been entered by a user before a receiving step and, if it is determined that there is missing data, prompt a user to enter missing data. In some embodiments, an interactive program is further configured to assess an incorrect entry of user input about a building material sample and prompt a user to correct.

According to various embodiments, an interactive program is further configured to store user input when a remote computing device is offline.

In some embodiments, an interactive program is further configured to connect a user to an offsite analyst. In some embodiments, entry of user input is substantially concurrent with connection to the analyst. In some embodiments, an interactive program is configured to display queries by an offsite analyst regarding a building material sample and/or user input, for example, prompting a user to supply missing data and/or to correct erroneous data.

In some embodiments, a providing step includes transmitting a prompt for a user to provide a response to a query posed by an offsite analyst, so that if an offsite analyst determines data, for example, is missing, incomplete, incorrect through an app an offsite analyst can request appropriate information and/or correction.

According to some embodiments, results of an offsite analysis are transmitted to a mobile client computing device within about 5 hours of receipt of user input, thereby allowing on-site completion of an assignment of value and/or like, kind, and quality assessment. In some embodiments, results of analysis are transmitted to a mobile client computing device within about 4 hours of receipt of user input. In some embodiments, results of analysis are transmitted to a mobile client computing device within about 3 hours of receipt of user input. In some embodiments, results of analysis are transmitted to a mobile client computing device within about 2 hours of receipt of user input. In some embodiments, results of analysis are transmitted to a mobile client computing device within about 1 hour of receipt of user input.

In some embodiments, an interactive program is further configured to display an application help system.

In some aspects, an interactive program is further configured to associate user input with a physical sample of a building material sample sent by a user to a lab.

According to some aspects of the present disclosure, wherein a characteristic corresponding to a building material sample is a type of material. In some embodiments, a type of material may be, for example, carpet, wood, vinyl, laminate, tile, siding, roofing, and/or rug.

In some embodiments, at least one piece of information indicative of a sample comprises information about a user and/or a site, such as a test location.

In some embodiments, a characteristic corresponding to a building material sample is a measurement.

According to some aspects, user input comprises at least one photo of a building material sample corresponding to at least one piece of information indicative of a building material sample.

In some embodiments, a receiving step succeeds entry of a plurality of user inputs about a building material sample separately collected.

According to some embodiments, the present disclosure is directed to a device for collection of data from a remote, mobile client computing device for assignment of value and/or like, kind, and quality assessment, including: a housing; a device platform within and/or upon the housing; an adjustable angle stand or cradle within and/or upon the device platform for placement of the remote, mobile computing device; and a sample platform comprising one or more (i) stop pins, (ii) raised edges, and/or (iii) clamps to align and/or secure a building material sample for collecting data using a mobile computing device.

In some embodiments, a device for collection of data from a remote, mobile client computing device for assignment of value and/or like, kind, and quality assessment also includes a cavity defined within the housing to facilitate location of a camera of the remote, mobile computing device.

In some embodiments, a device for collection of data from a remote, mobile client computing device for assignment of value and/or like, kind, and quality assessment also includes a mirror positioned relative to the platform to facilitate photographing a building material sample.

In some embodiments, a device for collection of data from a remote, mobile client computing device for assignment of value and/or like, kind, and quality assessment also includes a light source configured to illuminate at least a portion of a building material sample for collecting data about a building material sample using a remote, mobile computing device placed on a platform. In some aspects, a device for collection of data from a remote, mobile client computing device for assignment of value and/or like, kind, and quality assessment may also include a magnifier assembly positioned in relation to a platform to facilitate obtaining magnified photographic data using a remote, mobile computing device.

In some aspects, a device for collection of data from a remote, mobile client computing device for assignment of value and/or like, kind, and quality assessment also includes an elevation stand to facilitate angling of a mobile computing device for improved collection of data from a top of the building material sample.

In some embodiments, a device for collection of data from a remote, mobile client computing device for assignment of value and/or like, kind, and quality assessment also includes at least one at least one adjustable extension flap laterally disposed on the sample platform to support an oversized building material sample. In some embodiments, an at least adjustable extension flap laterally disposed on the sample platform includes a pair arms designed to hold hard surface samples of various widths. In some embodiments, an adjustable extension flap laterally disposed on the sample platform is configured to support an oversized material sample, for example, uncut and/or long boards, without an additional supporting surface.

The present disclosure, according to some embodiments is directed to a mobile near infrared spectrometer for qualitative material analysis, including: a programmable infrared light source comprising a plurality of infrared LEDs, each producing illuminating light at a unique, differentiable wavelength; an analog multiplexer, constant current LED driver, and microcontroller configured to sequentially illuminate a plurality of infrared LEDs one at a time for illumination of a material sample; optics for directing an illuminating light onto a material sample; a photodiode for receiving reflected infrared light from a material sample; a signal amplifier and/or conditioner for conversion of a signal from a photodiode corresponding to received, reflected infrared light to an appropriate voltage range; an analog to digital converter for conversion of amplified and/or conditioned signal to a digital signal; and a processor for recording, storing, transmitting, and/or analyzing a digital signal.

In some aspects, the present disclosure is directed to a mobile near infrared spectrometer for qualitative material analysis, wherein each of a plurality of LEDs produce light at each of a plurality of discrete wavelengths, for example, monochromatic LEDs suitable for distinguishing between a known plurality of categories of materials based on obtained signals, wherein a plurality of wavelengths consists of 2350+/−25 nm, 2050+/−25 nm, 1950+/−25 nm, 1850+/−25 nm, and/or 1750+/−25 nm, for example.

According to some embodiments, the present disclosure provides methods of distinguishing materials for qualitative analysis including steps of: providing, a mobile, near infrared spectrometer, a plurality of infrared LEDs, each producing illuminating light at a unique, differentiable wavelength an analog multiplexer, constant current LED driver, and microcontroller configured to sequentially illuminate a plurality of infrared LEDs one at a time for illumination of a material sample; optics for directing illuminating light onto a material sample; a photodiode for receiving reflected infrared light from a material sample; a signal amplifier and/or conditioner for conversion of a signal from a photodiode corresponding to received, reflected infrared light to an appropriate voltage range; an analog to digital converter for conversion of amplified and/or conditioned signal to a digital signal; and a processor for recording, storing, transmitting, and/or analyzing a digital signal; illuminating an infrared LEDs one at a time for illumination of a material sample; collecting data corresponding to each of a plurality of discrete wavelengths associated with LEDs; analyzing, by a processor, data obtained; and identifying a best match for a material sample.

In some aspects, methods of the present disclosure are directed to a mobile near infrared spectrometer for qualitative material analysis, wherein each of a plurality of LEDs produce light at each of a plurality of discrete wavelengths, for example, monochromatic LEDs suitable for distinguishing between a known plurality of categories of materials based on obtained signals, wherein a plurality of wavelengths consists of 2350+/−25 nm, 2050+/−25 nm, 1950+/−25 nm, 1850+/−25 nm, and/or 1750+/−25 nm, for example.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present disclosure are apparent in the detailed description that follows. It should be understood, however, that the detailed description, while indicating embodiments of the present disclosure, is given by way of illustration only, not limitation. Various changes and modifications within the scope of the invention will become apparent to those skilled in the art from the detailed description.

BRIEF DESCRIPTION OF THE DRAWING

The foregoing and other objects, aspects, features, and advantages of the present disclosure will become more apparent and better understood by referring to the following description taken in conjunction with the accompanying figures in which.

Figure 1:
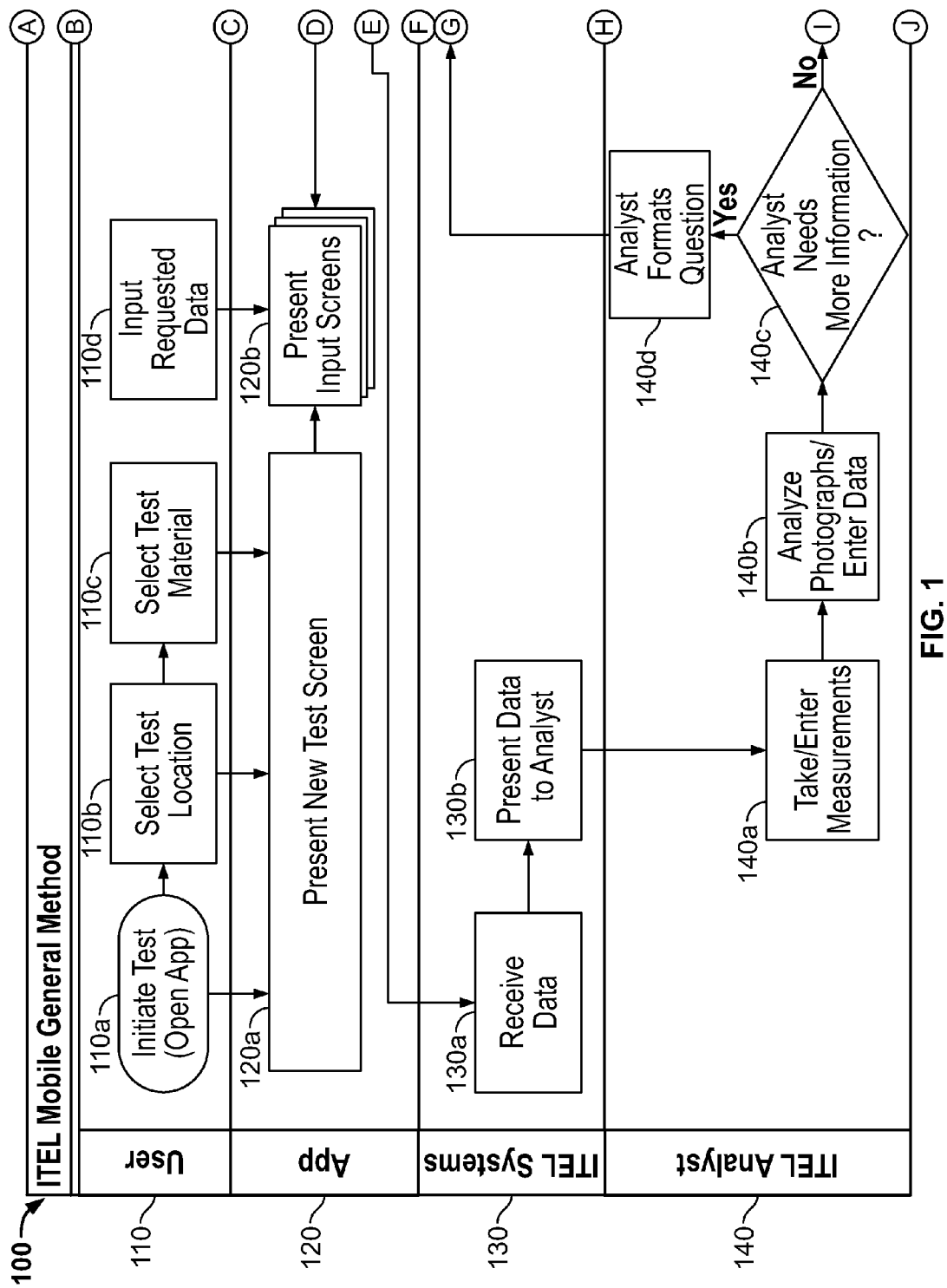
FIG. 1 shows an exemplary logic flow diagram in accordance with a general method of the present disclosure.
Figure 1:
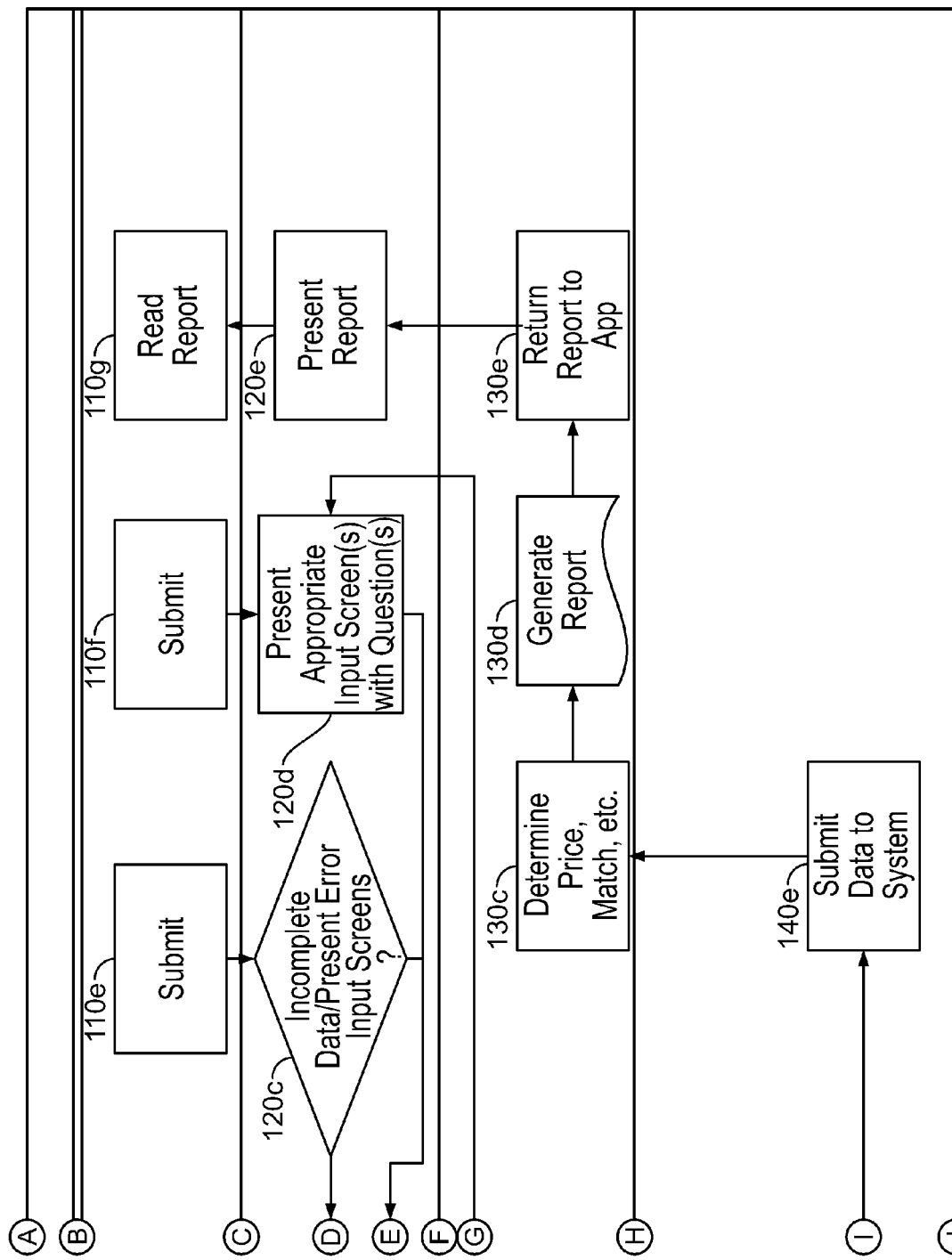

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DEFINITIONS

In order for the present disclosure to be more readily understood, certain terms are first defined below. Additional definitions for the following terms and other terms are set forth throughout the disclosure.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Carpet Terminology

Construction: The main carpet construction is identified as tufted, woven, or needle punch. The "finish" of the carpet is also identified. Examples of finish include Saxony, Textured Saxony, Level and Multi-level Loop, Graphics Saxony, etc.

Fiber Type: The most common fiber types used today are Nylon, Polyester, Olefin (polypropylene), and wool.

Fiber Ply: The number of plies found in the yarn bundle. If the yarn is not plied it is referred to as a velour carpet. Most carpets are constructed of two-ply yarn that is twisted together and heat set to hold the twist in the yarn.

Stitch Rate: The stitch rate is the number of stitches per inch in a tufted carpet.

Gauge/Pitch: Gauge is the distance between needles on the needlebar that produced the carpet. Gauge is expressed in fractions of an inch. Pitch is the number of yarns per 27 inches of the width of a woven carpet.

Pile Height: The height of a finished carpet tuft from the top of the primary backing to the tip of the exposed tuft is measured in inches.

Backing Material: This refers to the secondary backing of the carpet. The backing is usually made of synthetic fiber (Jute, a natural fiber, is rarely used today).

Face Weight: The weight of the fiber, measured in ounces, in one square yard of carpet.

Tufts/SQ inch: The number of individual tufts in one square inch of carpet.

Vinyl Terminology

Product Form: The product form of the vinyl sample will be listed as sheet, tile, or plank.

Tile/Plank Size: If available, the size of a complete tile or plank will be listed.

Construction: The construction type of the sample is listed. Possible types include: inlaid, printed, homogenous, VCT, solid, and backing.

Inlaid: The pattern is created through placement of vinyl granules, chips, or cubes that are fused under heat and pressure.

Printed: The most common method. The pattern is printed on a core layer and covered by a wearlayer.

Homogenous: The flooring is manufactured by mixing chips or particles throughout the product. The pattern is visible on both sides of the product.

VCT: The flooring is created from vinyl particles fused under heat and pressure. No backing material or wearlayer will be present.

Solid: The sample is constructed of a solid piece of vinyl with no wearlayer.

Backing: Sheet vinyl products have a felt, vinyl or fiberglass backing Residential tile products have a dry-back or self-adhesive backing.

Wearlayer Type: Wearlayer is a thin protective layer on top of the flooring surface. The two basic wearlayers are vinyl and urethane, with urethane found on higher-end products. The new, enhanced urethane wearlayers may significantly affect price and will be noted as found in the analysis.

Wearlayer Thickness: The average thickness of the wearlayer, measured in mils.

Overall Thickness: The overall thickness of the sample, measured in mils.

Laminate Terminology

Product Form (Construction): The product form of the sample will be High Pressure Laminate (HPL), Direct Pressure Laminate (DPL), or Particle Board. HPL is constructed under 1400 psi while DPL is 1200 psi.

Surface Texture: Evaluated as Smooth, Tic, Embossed, or Embossed in Register. Embossed In Register is when the wood grain embossing identically matches the wood grain pattern.

Locking System: The edges of the plank's width that connects each board. Locking system names are unique to each manufacturer. Various locking systems currently used are Swiftlock, Uniclic, Duraloc, Surelock and M Lock.

Class: Class refers to the laminate's impact resistance. The class of flooring will be listed as residential only, residential/light commercial, moderate commercial, or heavy commercial.

Width: The overall width of the flooring sample.

Core Density: Core Density describes the type of core. In today's market, HDF (High Density Fiberboard) is the most common.

Core Thickness: The overall thickness of the core of the sample is measured in millimeters.

Abrasion Resistance (AC Rating): Also referred to as the wear rating, it is the European Standard AC Rating. The range runs from the least resistant rating of AC1 To AC5, the most resistant to abrasion.

Attached Pad: Indicates if the laminate flooring is manufactured with an attached pad.

Wood Terminology

Product Form (Construction): The product forms of wood are described as engineered, solid, or hybrid.

Board Thickness: The overall thickness of the sample is measured in inches

Cut: The direction of the grain in the veneer.

Engineered Wood: Sometimes referred to as laminated wood. Engineered wood is constructed with 3-12 plies of wood compressed together.

Hybrid: Hard surface flooring with a laminate core and a thin veneer of wood on the surface.

Locking Type: The method of installation is evaluated as self-adhesive, glued, stapled, nailed, or floating (glueless).

Ply: Number of layers of wood on engineered and hybrid flooring samples.

Visual: The physical appearance of the wood sample.

Width: The overall width of the flooring sample.

Species: The wood type of the sample. In an engineered wood sample, the species of the veneer is typically different then the inner plies.

Veneer Thickness: The thickness of the veneer in an engineered or hybrid wood sample measured in inches.

Surface Finish: The application of the finish. On-site finished are applied after the wood floor has been installed. Factory finishes are applied during the manufacturing process.

Ply Composition: For engineered wood, the type(s) of wood used in the layers.

Stained Finish: Indicates if the received sample had a finish applied (either on-site or pre-finished).

Siding Terminology

Nail Hem: The top of the edge of a panel that gets nailed to the wall.

Lock: Where two siding panels join, or lock together.

Profile: Side view of a siding panel.

Shadow Line: The shadow pattern cast by a particular siding in the sunlight. Shadow line is influenced by the style and butt height of the siding.

Square: Unit of measure of siding equal to 100 SF.

Butt Edge: The section of vinyl siding that projects from the wall. As a rule of thumb, a larger butt edge creates a more pronounced shadow line and a stiffer panel.

Clapboard: This architectural term refers to a thin, narrow board with one edge thicker than the other and is used as siding.

Dutchlap: This architectural term refers to a flat, horizontal band. In the vinyl business it refers to the wide trim that runs along the roof line.

Exposure: The width of each board of siding. Also referred to as a reveal.

Finish/Pattern: Refers to the texture (and sometimes to the gloss level) of a siding panel.

DETAILED DESCRIPTION OF CERTAIN EMBODIMENTS

The present disclosure provides, among other things, devices and methods for data collection. Various embodiments of the present disclosure acknowledge that assessment of value and/or like, kind, and quality for building materials products, such as flooring, carpet, siding, roofing, etc., typically occurs at an installed location that is remote to a lab setting. A value and/or like, kind, and quality assessment would require a user to travel to a remote site and obtain a physical sample and then ship a sample to a lab site for analysis and comparison to known building material products. A user then waits 2-4 days for results. After analysis and identification of a building material product for matching value and/or like, kind, and quality by a lab, a report of assessment is sent to a property owner, installer, builder, or insurance claim adjuster. Ultimately, this process is both inefficient and time consuming.

The present disclosure appreciates inefficiencies that result from a multi-stage, multi-location procedure. Devices and methods of the present disclosure address these inefficiencies. In some embodiments, methods of the present disclosure are directed to an on-site value and/or like, kind, and quality assessment. In some embodiments, the present disclosure provides access to specially trained personnel and lab protocols to provide results in near real time. According to some embodiments, methods of the present disclosure include providing a user of a remote, mobile computing device with an application ("app") for collecting information, data, and photos for value assessment and/or like, kind, and quality assessment of building materials products. In some embodiments, an app is configured to display to a series of interactive screens on a device prompting entry of information, data, and photos about a building material sample. In some embodiments, methods of the present disclosure include receiving by a service provider information, data, and photos about a building material sample. Following a value assessment and/or like, kind, and quality assessment of a building materials products, in accordance with some embodiments of the present disclosure, a service provider is transmitting results of analysis to a user's mobile computing device.

In some embodiments, devices and methods of the present disclosure rely on a highly flexible paradigm which permits adapting an app to address changing customer requirements in the most efficient manner. Adaptability permits flexibility, speed, ease of use, reduced frustration, usability from disconnected and/or remote locations, and security to facilitate a user with little or no training to collect and enter information, photo(s), and/or data indicative of unknown building material samples for on-site value assessment and/or like, kind, and quality assessment.

In some embodiments, an app is built on a core of three layout styles or user input workflows. In some embodiments, an app layout style is "Photo Only," wherein a user input displays a photo display, camera button, delete button, and an add additional photos option. Upon adding additional photos, a photo ribbon may be shown. Additionally, photo management capabilities may be displayed to the user.

In various aspects of the present disclosures, there is an app layout style for "Data" that allows a user to provide user input as information selected from text boxes, dropdown list boxes, radio buttons. In some embodiments, a data layout is configurable through a framework as above described and may be rearranged or changed (e.g. data types, controls and validations) as needed.

According to some implementations, a "Conditional" layout provides a user with a display having a simple yes/no paradigm for adapting a workflow to a situation. A confidential layout allows a system to require additional user input or alteration of a workflow when necessary.

In some embodiments, a user may access a combination of these layout styles, such that a user seamlessly moves through all three to adequately enter information, data, and photos.

Workflow

Illustrated in FIG. 1 is an exemplary logic workflow diagram [100] in accordance with the general method of the present disclosure. In some embodiments, a workflow [100] is performed using apparatus as described herein. In some embodiments, use of apparatus to perform workflow [100] is according to the present methods and/or as described herein. In some embodiments, the workflow paradigm of an app of the present disclosure is designed such that it leads a user through an efficient, wizard-style interface. In some aspects, as a user enters information or selects from available choices, such antecedent screen choices affect display screens and choices in subsequent screens. This interface/layout creates a cohesive and consistent input experience for a user.

According to some embodiments, to proceed through the process workflow, the user provides user input entry. In some aspects, this user input can include information input, data input, photographic input, or any combination of those. In some embodiments, where a user takes, inputs, enters, and/or uploads a photograph, a user may include multiple photographs, for example showing different angles of the identified feature. Additionally, in some embodiments, the app may ask the user a question to define or clarify a specific situation and depending upon the response, present additional options for input.

Referring to the User level of the diagram [110], in some embodiments, a user opens the app to initiate a test [110a]. In some embodiments, a user inputs general claim information and designates the location wherein data, information, and/or photos will be taken either on-site or in a lab [110b]. In some embodiments, a user will select from a list of choices of material types representative of an unknown sample [110c].

Referring to the App level of the diagram [120], in some embodiments, a user is presented with a new test screen [120a]. In some embodiments, a new test screen [120a] for example initiates a test for a user and presents a user with input screens for location information and/or materials. In some embodiments, a list of materials presented to a user may include for example: carpet, wood, laminate, vinyl, tile, siding, roofing or rug. In some embodiments, in response to user input identifying the material type, the app presents a user with a material specific workflow and present input screens

[120b] for collecting required and optional information needed. In some embodiments, at a User level [110], a user inputs requested data [110d] in response to presented input screens [120b]. In some embodiments, an app presents to a user an Incomplete Data/Present Error Input screen [120c] so that a user may add additional information, data, and/or photos as needed and/or helpful for identification of value and/or like, kind, and quality assessment. In some embodiments, a user submits additional information, data, and/or photos [110e] in response to an Incomplete Data/Present Error Input screen [120c].

Referring to the ITEL Systems level of the diagram [130], in some embodiments, a service provider computing device receives data provided by a user through a mobile client computing device [130a]. In some embodiments, a service provider computing device presents received data [130a] to an off-site analyst [130b].

Referring to the ITEL Analyst level of the diagram [140], in some embodiments, an offsite analyst for a service provide takes and enters measurements [140a]. In some embodiments, an offsite analyst for a service provide analyzes photographs, and enters data [140b]. In some embodiments, an offsite analyst requires additional information [140c]. In some embodiments, when an offsite analyst requires additional information, then an offsite analyst may pose a query to a user through an app to prompt a user to provide a response to a query [140d], for example an analyst may need additional data, measurements, and/or photos. In some embodiments, in response to an offsite analyst formatting a question [140d] at the App level of the diagram [120], an app presents appropriate input screen(s) with question(s) [120d]. In some embodiments, in response to an app presenting appropriate input screen(s) with question(s) at the User level of the diagram [110], a user submits [110f], for example additional information such as additional data, measurements, and/or photos. At the ITEL Systems level of the diagram [130], in some embodiments, a service provider computing device receives data [130a] provided by a user through a mobile client computing device from a user submission [110f], for example, additional information such as additional data, measurements, and/or photos. In some embodiments, a service provider computing device presents received data [130a] to an off-site analyst [130b]. In some embodiments, an offsite analyst then submits collected information [140e], including for example, data, photos, and/or measurements to the ITEL system for determination of price, match, etc.

Referring to the ITEL Systems level of the diagram [130], in some embodiments, a service provider computing device receives data provided by an analyst and determines a price, match, etc. [130c]. In some embodiments, a service provider computing device generates a report [130d]. In some embodiments, a service provider computing device returns a report to an app [130e].

Referring to the App level of the diagram [120], in some embodiments, an app presents a report [120e] that was provided by a service provider computing device.

Referring to the User level of the diagram [110], in some embodiments, a user reads a report presented on an app.

Application for Use on a Mobile Computing Device

As illustrated in FIG. 2 through FIG. 8, across various implementations, screen layouts enable a user to access all necessary user input displays; including: a camera, photo manipulation tools, and information and data entry screens. In some embodiments, a display requiring user inputs are populated with a number of selectable options. Display interfaces decrease a possibility of mistyping information. In some embodiments, display interfaces are dropdown lists, text boxes, and/or radio buttons are populated with options from dynamic lists that may change, depending on customer needs or changing lab needs.

FIG. 2 through FIG. 5 show an exemplary screenshots for a new test for a carpet sample in accordance with the present disclosure. In some embodiments, through a photo display, a user input entry will be in a form of a photo or a series of photos depicting a variety of visual angles of an unknown sample of a building material, such as carpet, wood, etc. According to some embodiments, photos may be taken through an app installed on a remote, mobile computing device in accordance with the present disclosure. In some embodiments, photos may be uploaded from a remote, mobile computing device or an external storage as provided below in more detail.

FIG. 2 through FIG. 8 show a series of screenshots presenting an input entry interface on a remote, mobile computing device to a user in accordance with the present disclosure. Evident from screen layouts shown in FIG. 2, FIG. 2 through FIG. 8 is an ability to navigate. As shown in FIG. 2A, referring to a screenshot of a Claim Info screen [210], is a top navigation bar [210a] that displays navigation buttons. Navigation buttons [210a] allow, for example, a user to navigate back to a prior screen, forward to a next screen, or allow a user to navigate to a home screen.

Figure 2:
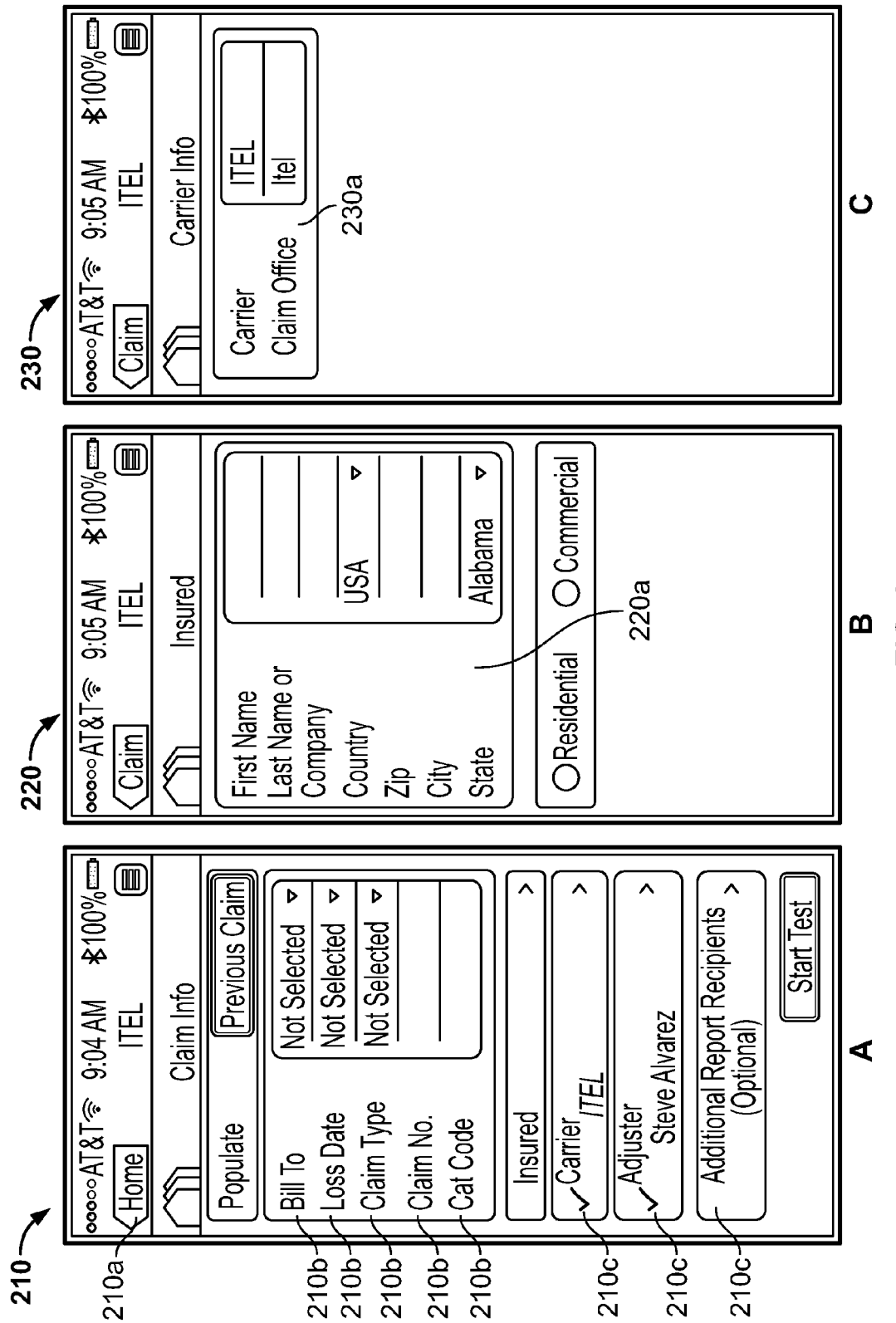
FIG. 2 shows a series of screenshots presenting an input entry interface on a remote, mobile computing device to a user in accordance with the present disclosure.

FIG. 2 shows a series of screenshots presenting an input entry interface on a remote, mobile computing device to a user in accordance with the present disclosure. In some embodiments, as shown in FIG. 2, a user initiates a new claim. FIG. 2A through FIG. 2C show exemplary screenshots for gathering information about a claim, an insured party, and/or a carrier.

In some embodiments, depending of a type of transaction, a user may be asked to enter claim information [210b], for example, billing name and/or address, claim information, loss date and claim no. FIG. 2A shows an exemplary user drop down menu [210c] to select, for example, insured information, carrier information, etc. FIG. 2A also shows a start test button [210d] that initiates a test. FIG. 2B shows an exemplary Insured user input screen [220], including a screenshot of an app presenting fields for entering information regarding an insured party [220a], such as an address. FIG. 2C shows an exemplary Carrier Info user input screen [230], including a screenshot of an app presenting fields for entering information regarding a carrier [230a].

Figure 3:
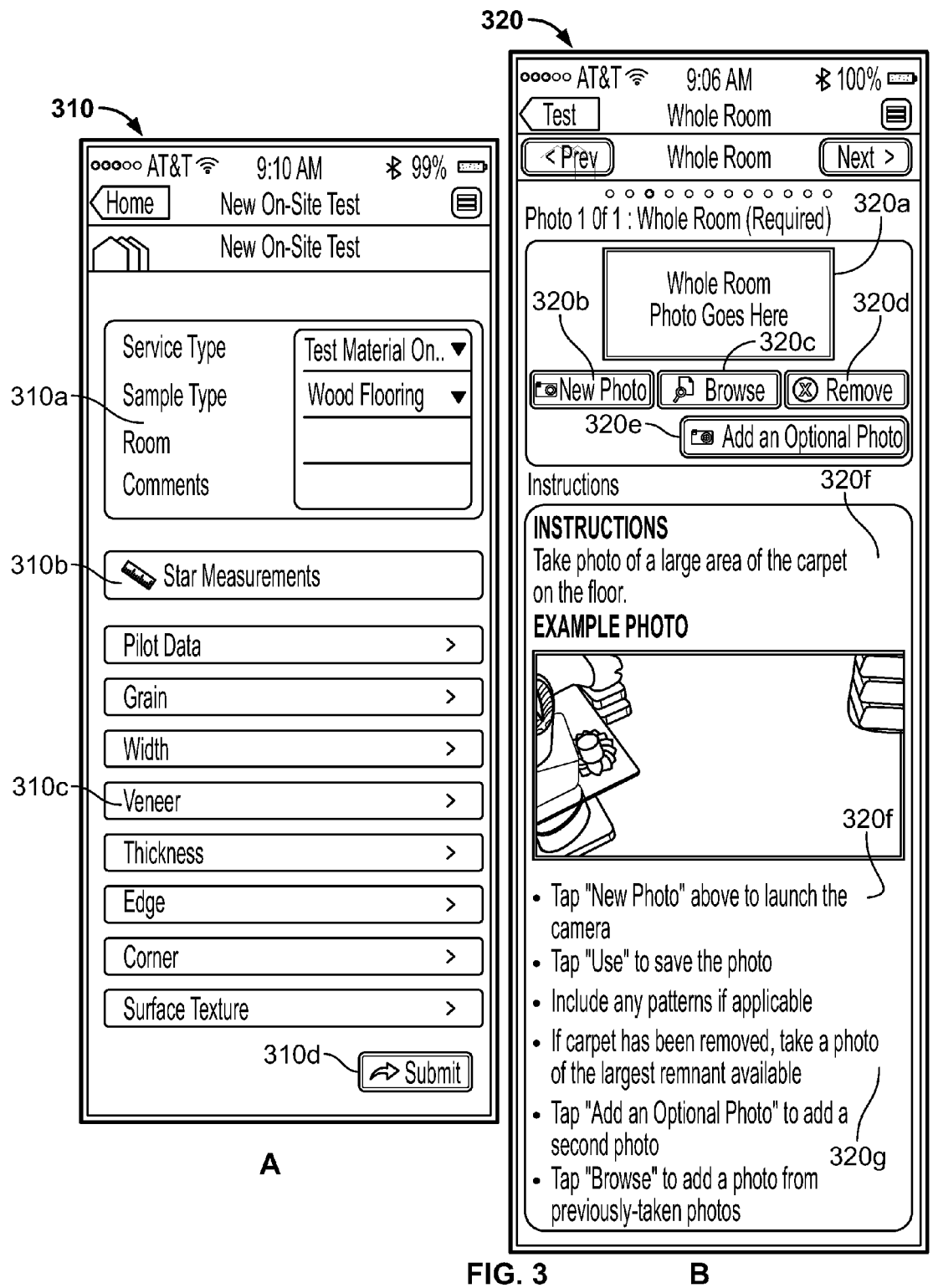
FIG. 3 shows a series of screenshots providing a new on-site test for entry of user input and photos for carpet acquired from a remote, mobile computing device in accordance with the present disclosure.
Figure 3:
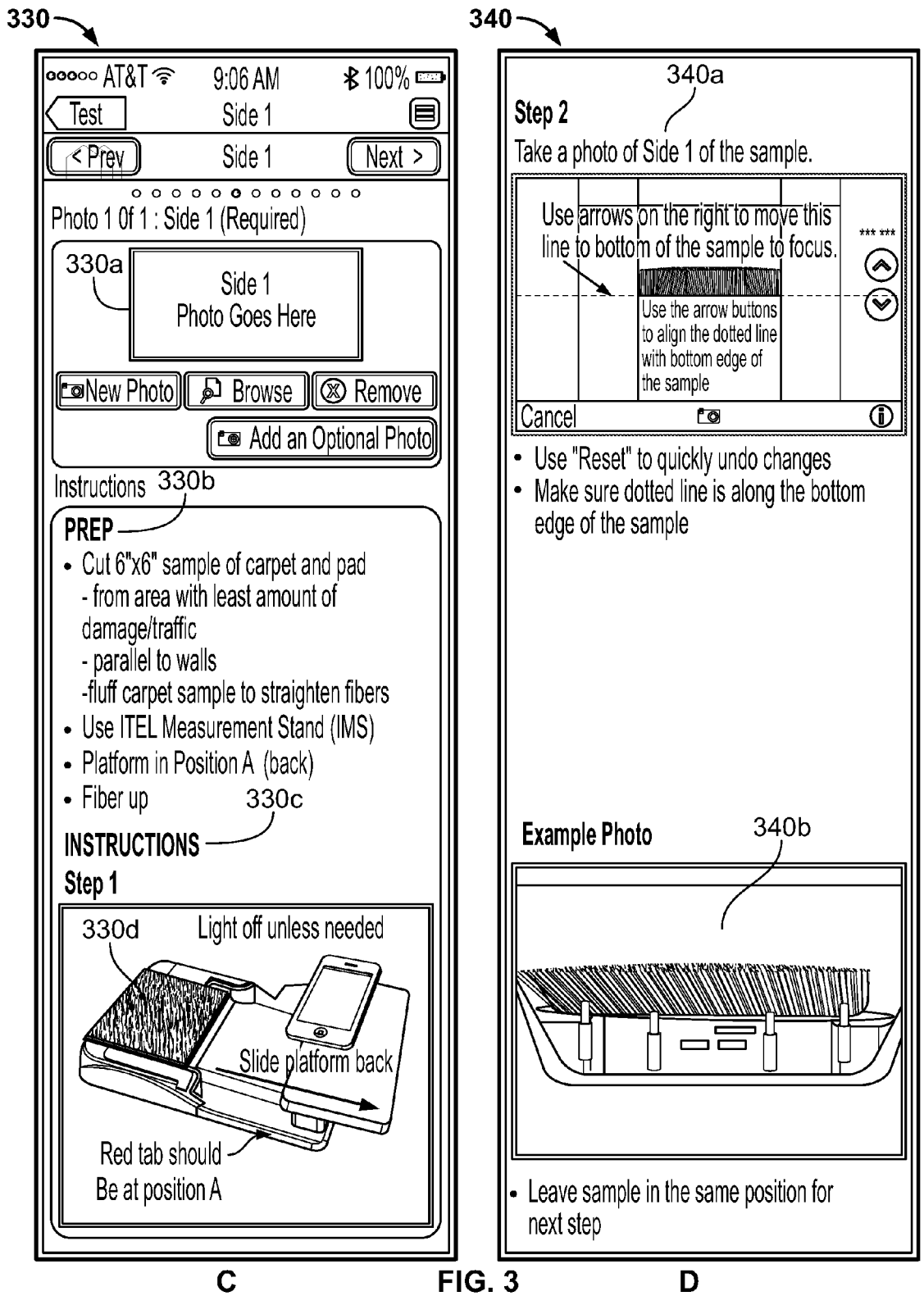
Figure 3:
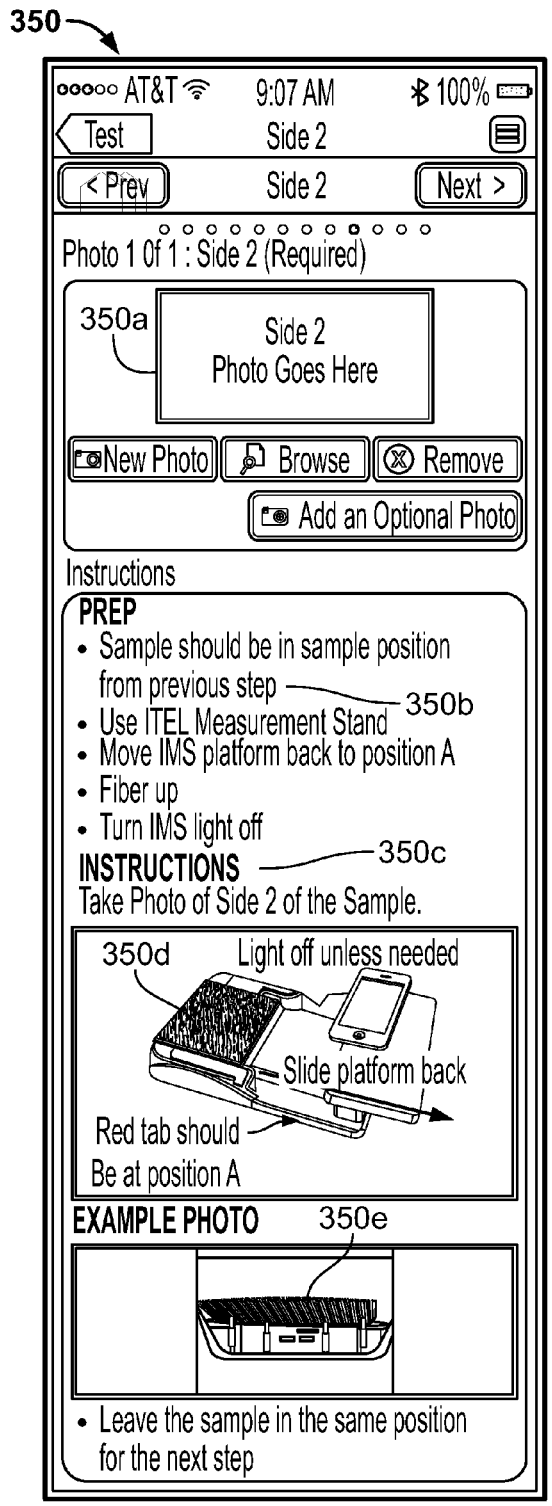

FIG. 3 shows a series of screenshots presenting an input entry interface on a remote, mobile computing device to a user in accordance with the present disclosure. In some embodiments, as shown in FIG. 3, a user initiates a new onsite test. FIG. 3A-D shows a new on-site test for a carpet sample.

FIG. 3A shows a screenshot of an app presenting fields for entering information regarding a new on-site test [310]. FIG. 3A shows an input screen so that a user may populate information fields [310a], such as service type, sample type, and room, for example. FIG. 3A shows a button so that a user can initiate taking measurements [310b]. In some embodiments, a user takes a variety of measurements of an unknown sample, such as a carpet sample (as shown herein). In some embodiments, a display on an app prompts a user to take measurements. In some embodiments, screens prompting a user to take measurements are presented one display screen at a time. In some embodiments, user input provided on a preceding screen affects subsequent screen displays to a user. In some embodiments, a user may use an app and a remote, mobile computing device to acquire measurements. In some embodiments, a user may acquire photos of a building material sample adjacent to a measurement device, such as a ruler. In some embodiments, a user may acquire measurements using a separate application on a remote, mobile computing device, for example, a measurement app. In some embodiments, a user may manually acquire measurements and enter each measurement into an app entry screen. FIG. 3A shows exemplary drop down menus that display different building material characteristics for a user to select when describing a sample [310c]. A drop down menu may include, for example, depending on a building material choice a user is evaluating: pilot data, grain, width, veneer, thickness, edge, corner, and/or surface texture. Referring to the bottom of the new onsite test screen [310], is a Submit button [310d]. A submit button [310d] is used to save information, data, and photos before moving to a next screen.

FIG. 3B shows a screenshot of an app presenting fields for entering a photo, such as a whole room photo of a carpet sample [320]. FIG. 3B shows options including taking a whole room photo using a mobile computing device camera [320a]. FIG. 3B shows a button to select when a user want to take a new photo [320b]. FIG. 3B shows options including uploading a photo previously taken using for example a mobile computing device camera or another camera [320c]. FIG. 3B shows a button to select when a user want to take remove a previously added photo [320d]. FIG. 3B shows a button to select when a user want to take additional photos [320e]. FIG. 3B shows instructions for taking, for example, a whole room photo [320f]. FIG. 3B also shows instructions for acquiring photos of a carpet remnant when a carpet sample was previously removed [320g].

FIG. 3C and FIG. 3D show screenshots of an app presenting fields for entering information regarding a Side 1 of a carpet sample. FIG. 3C and FIG. 3D show instructions, Step 1 and Step 2, for acquiring at least one photo of Side 1 of a carpet sample using a remote, mobile computing device.

FIG. 3C shows a screenshot of an app presenting fields regarding a Side 1 of a carpet sample [330]. FIG. 3C shows options entering a photo of a Side 1 using a mobile computing device camera [330a]. FIG. 3C shows options including taking a photo of a Side 1 using a mobile computing device camera. FIG. 3C also shows options including uploading a photo previously taken using for example a mobile computing device camera or another camera and options for including additional photos. FIG. 3C shows a button to select when a user want to take remove a previously added photo and a button to select when a user want to take additional photos. FIG. 3C shows instructions for a user to prepare a carpet sample for acquiring a Side 1 photo of a carpet using a remote, mobile computing device [330b]. FIG. 3C shows a Step 1 for acquiring at least one photo of Side 1 of a carpet sample using a remote, mobile computing device [330c]. FIG. 3C shows a Step 1 for acquiring a Side 1 photo and provides an illustration showing correct use of an apparatus for collection of at least one photo of a Side 1 of a carpet sample from a remote, mobile client computing device for assignment of value and/or like, kind, and quality assessment of the present disclosure [330d].

FIG. 3D shows a screenshot of an app presenting fields for entering information regarding a Side 1 of a carpet sample [340]. FIG. 3D specifically shows Step 2 for acquiring at least one photo of Side 1 of a carpet sample. FIG. 3D shows Step 2 for acquiring a Side 1 photo and provides instructions for acquiring an image [340a] and provides an example photo to compare with a photo a user acquires during a Step 2 [340b].

FIG. 3E shows a screenshot of an app presenting fields regarding Side 2 a carpet sample [350]. FIG. 3E shows options including entering a photo of Side 2 using a mobile computing device camera [350a]. FIG. 3E shows options for taking a photo of Side 2 using a mobile computing device camera. FIG. 3E shows options including uploading a photo previously taken using for example a mobile computing device camera or another camera. FIG. 3E shows a button to select when a user want to take remove a previously added photo and a button to select when a user want to take additional photos. FIG. 3E shows instructions for a user to prepare a carpet sample for acquiring a Side 2 photo of a carpet using a remote, mobile computing device [350b]. FIG. 3E shows instructions for acquiring at least one photo of Side 2 of a carpet sample [350c]. FIG. 3E provides an illustration showing correct use of an apparatus for collection of at least one photo of a Side 2 of a carpet sample from a remote, mobile client computing device for assignment of value and/or like, kind, and quality assessment of the present disclosure [350d]. FIG. 3E shows an example photo to compare with a photo a user acquires during acquisition of a Side 2 photo [350e].

Figure 4:
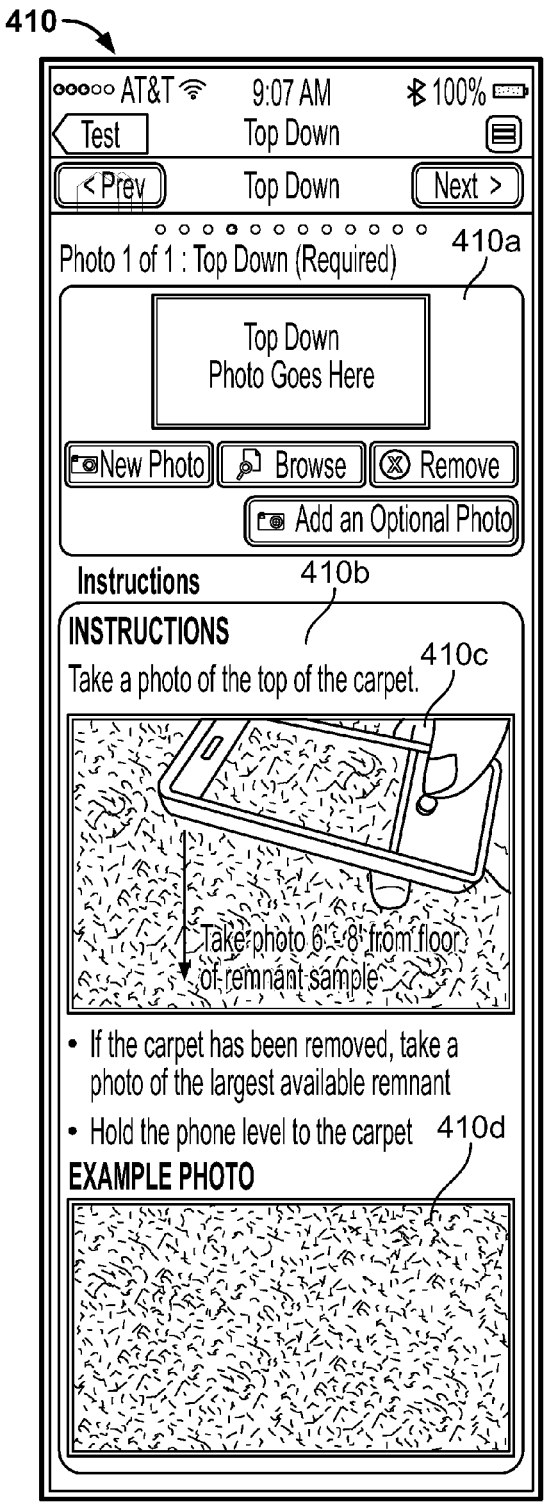
FIG. 4 shows a series of screenshots providing entry of photos for carpet acquired from a remote, mobile computing device in accordance with the present disclosure.
Figure 4:
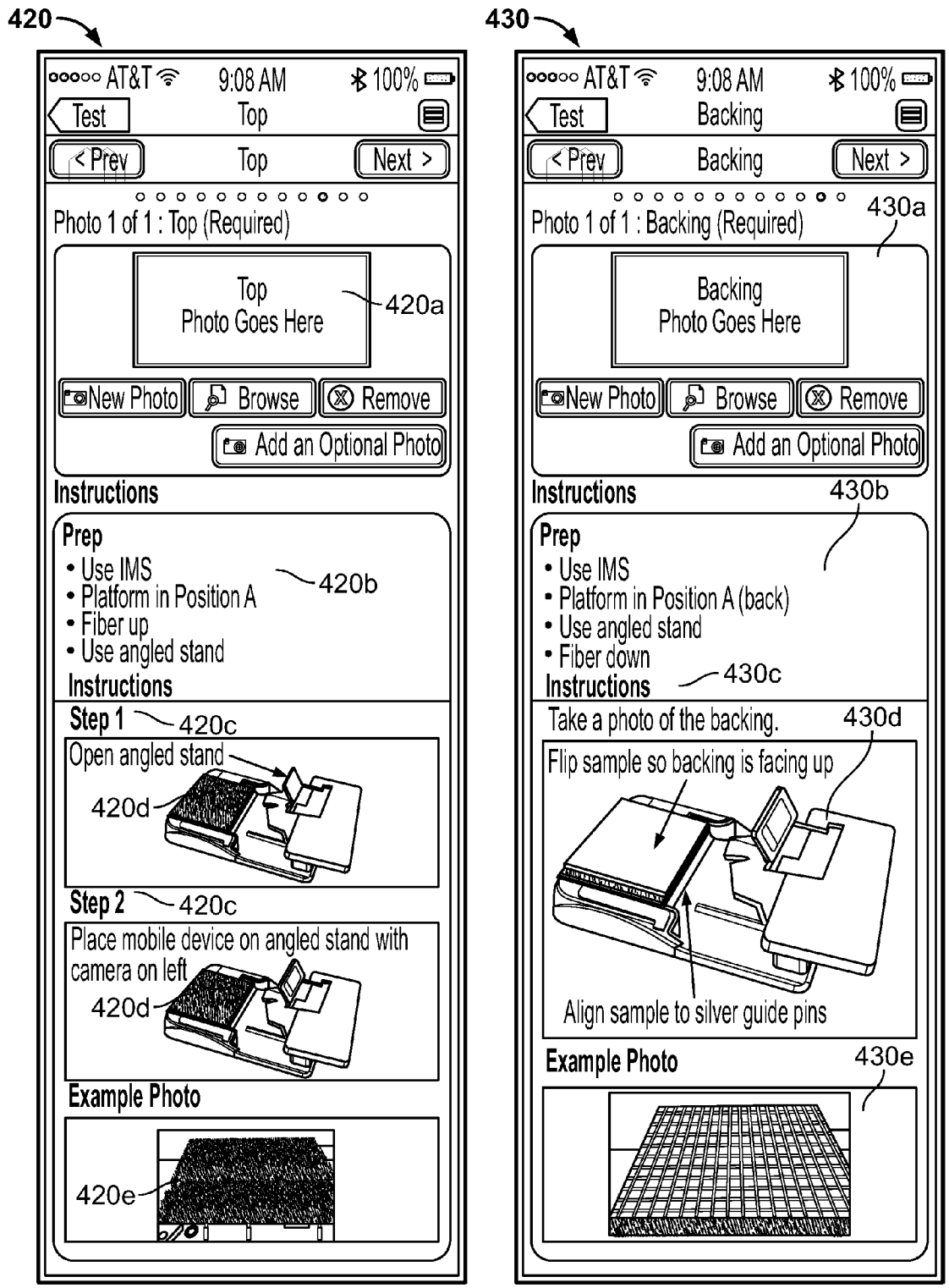

FIG. 4 shows a series of screenshots presenting an input entry interface on a remote, mobile computing device to a user in accordance with the present disclosure. FIG. 4A through FIG. 4C show acquisition of information, data, and/or photos of a top and backing of a carpet sample.

FIG. 4A shows a screenshot of an app presenting fields regarding a top down photo of a carpet [410]. FIG. 4A shows options for entering a top down photo of a carpet using a mobile computing device camera [410a]. FIG. 4A shows options for taking a top down photo of a carpet using a mobile computing device camera. FIG. 4A shows options including uploading a photo previously taken using for example a mobile computing device camera or another camera. FIG. 4A shows a button to select when a user want to take remove a previously added photo and a button to select when a user want to take additional photos. FIG. 4A shows instructions for acquiring at least one photo of a top of a carpet sample [410b]. FIG. 4A shows instructions for acquiring photos of a carpet remnant when a carpet sample was previously removed [410c]. FIG. 4A shows an example photo to compare with a photo a user acquires during acquisition of a top down photo [410d].

FIG. 4B shows a screenshot of an app presenting fields regarding a top of a carpet sample [420]. FIG. 4B shows options for entering a photo of a top of a carpet sample using a mobile computing device camera [420a]. FIG. 4B shows options including uploading a photo previously taken using for example a mobile computing device camera or another camera. FIG. 4B shows a button to select when a user want to take remove a previously added photo and a button to select when a user want to take additional photos. FIG. 4B shows instructions for a user to prepare a carpet sample for acquiring a photo of a top of a carpet sample using a remote, mobile computing device [420b]. FIG. 4B shows instructions for acquiring at least one photo of a top of a carpet sample, step 1 and step 2 [420c]. FIG. 4B provides an illustration showing correct use of an apparatus for collection of a photo of a top of a carpet sample from a remote, mobile client computing device for assignment of value and/or like, kind, and quality assessment of the present disclosure [420d]. FIG. 4B shows an example photo to compare with a photo a user acquires during acquisition of a Side 2 photo [420e].

FIG. 4C shows a screenshot of an app presenting fields regarding a backing of a carpet sample [430]. FIG. 4C shows options for entering a photo of a backing of a carpet sample using a mobile computing device camera [430a]. FIG. 4C shows options including uploading a photo previously taken using for example a mobile computing device camera or another camera. FIG. 4C shows a button to select when a user want to take remove a previously added photo and a button to select when a user want to take additional photos. FIG. 4C shows instructions for a user to prepare a carpet sample for acquiring a photo of a backing of a carpet sample using a remote, mobile computing device [430b]. FIG. 4C shows instructions for acquiring at least one photo of a backing of a carpet sample [430c]. FIG. 4C provides an illustration showing correct use of an apparatus for collection of a photo of a backing of a carpet sample from a remote, mobile client computing device for assignment of value and/or like, kind, and quality assessment of the present disclosure [430d]. FIG. 4C shows an example photo to compare with a photo a user acquires during acquisition of a photo a backing of a carpet sample [430e].

Figure 5:
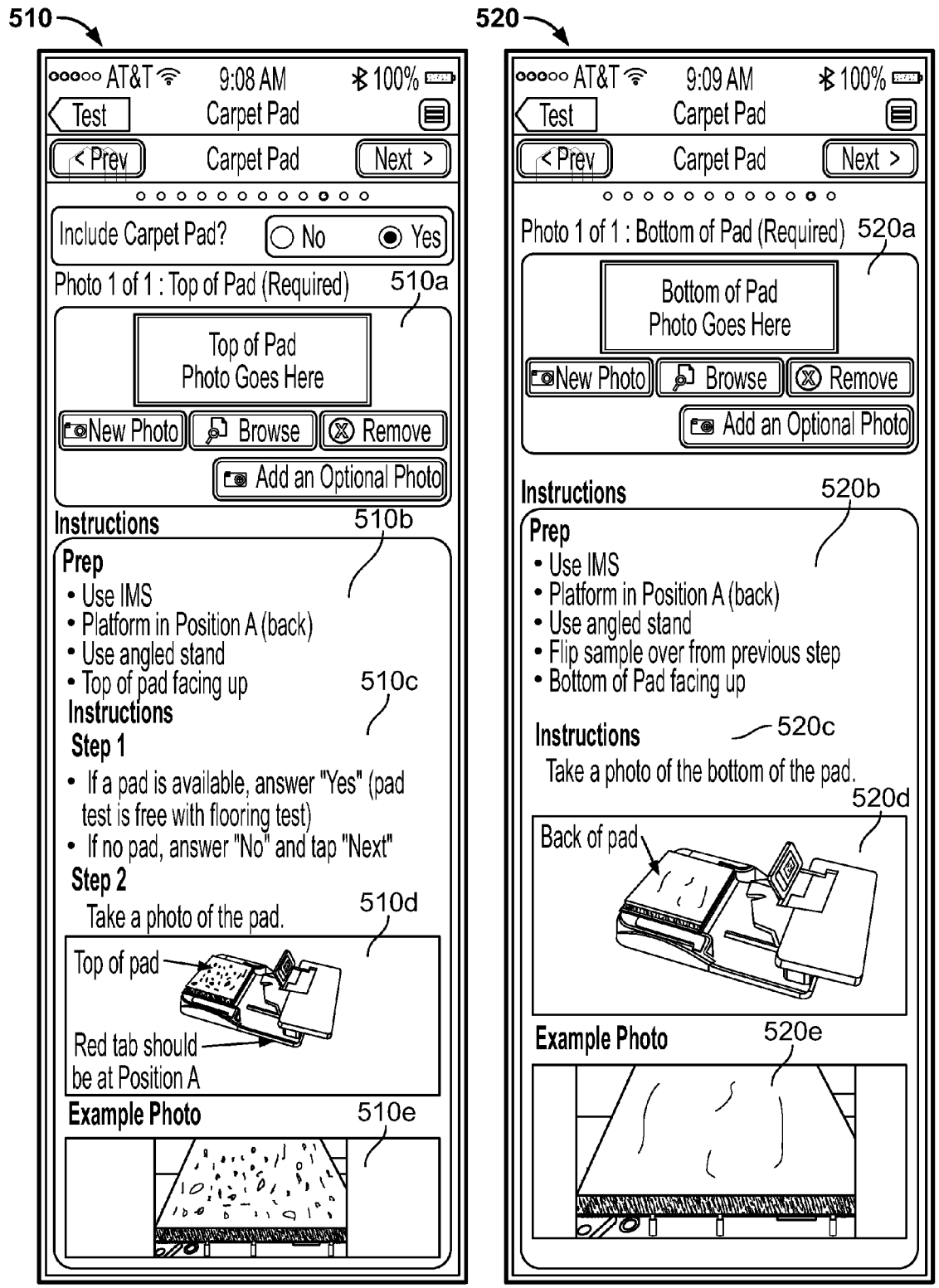
FIG. 5 shows a series of screenshots providing entry of user input and photos for carpet pad acquired from a remote, mobile computing device in accordance with the present disclosure.

FIG. 5 shows screenshots presenting an input entry interface on a remote, mobile computing device to a user in accordance with the present disclosure. In some embodiments, a display prompts entry from a user to identify whether there is a flooring pad to assess. FIG. 5A shows a radio button so that a user can indicate (e.g. by proving an indication of 'yes' or 'no') whether a carpet pad is present. FIG. 5A shows a screenshot when a user indicates a carpet pad is present. In some embodiments, when a user indicates a carpet pad is not present photo entry screens and input entry displays do not appear to a user. FIG. 5A and FIG. 5B show acquisition of information, data, and/or photos of a carpet pad sample.

FIG. 5A shows a screenshot of an app presenting fields regarding a carpet pad sample [510]. FIG. 5A shows options for entering a photo of a carpet pad sample using a mobile computing device camera [510a]. FIG. 5A shows options including uploading a photo previously taken using for example a mobile computing device camera or another camera. FIG. 5A shows a button to select when a user want to take remove a previously added photo and a button to select when a user want to take additional photos. FIG. 5A shows instructions for a user to prepare a carpet pad sample for acquiring a photo of a carpet pad sample using a remote, mobile computing device [510b]. FIG. 5A shows instructions for acquiring at least one photo of a carpet pad sample [510c]. FIG. 5A provides an illustration showing correct use of an apparatus for collection of a photo of a carpet pad sample from a remote, mobile client computing device for assignment of value and/or like, kind, and quality assessment of the present disclosure [510d]. FIG. 5A shows an example photo to compare with a photo a user acquires during acquisition of a photo a carpet pad sample [510e].

FIG. 5B shows a screenshot of an app presenting fields regarding a backing of a carpet pad sample [520]. FIG. 5B shows options for entering a photo of a backing of a carpet pad sample using a mobile computing device camera [520a]. FIG. 5B shows options including uploading a photo previously taken using for example a mobile computing device camera or another camera. FIG. 5B shows a button to select when a user want to take remove a previously added photo and a button to select when a user want to take additional photos. FIG. 5B shows instructions for a user to prepare a carpet pad sample for acquiring a photo of a backing of a carpet pad sample using a remote, mobile computing device [520b]. FIG. 5B shows instructions for acquiring at least one photo of a backing of a carpet pad sample [520c]. FIG. 5B provides an illustration showing correct use of an apparatus for collection of a photo of a backing of a carpet pad sample from a remote, mobile client computing device for assignment of value and/or like, kind, and quality assessment of the present disclosure [520d]. FIG. 5B shows an example photo to compare with a photo a user acquires during acquisition of a photo a backing of a carpet pad sample [520e].

Figure 6:
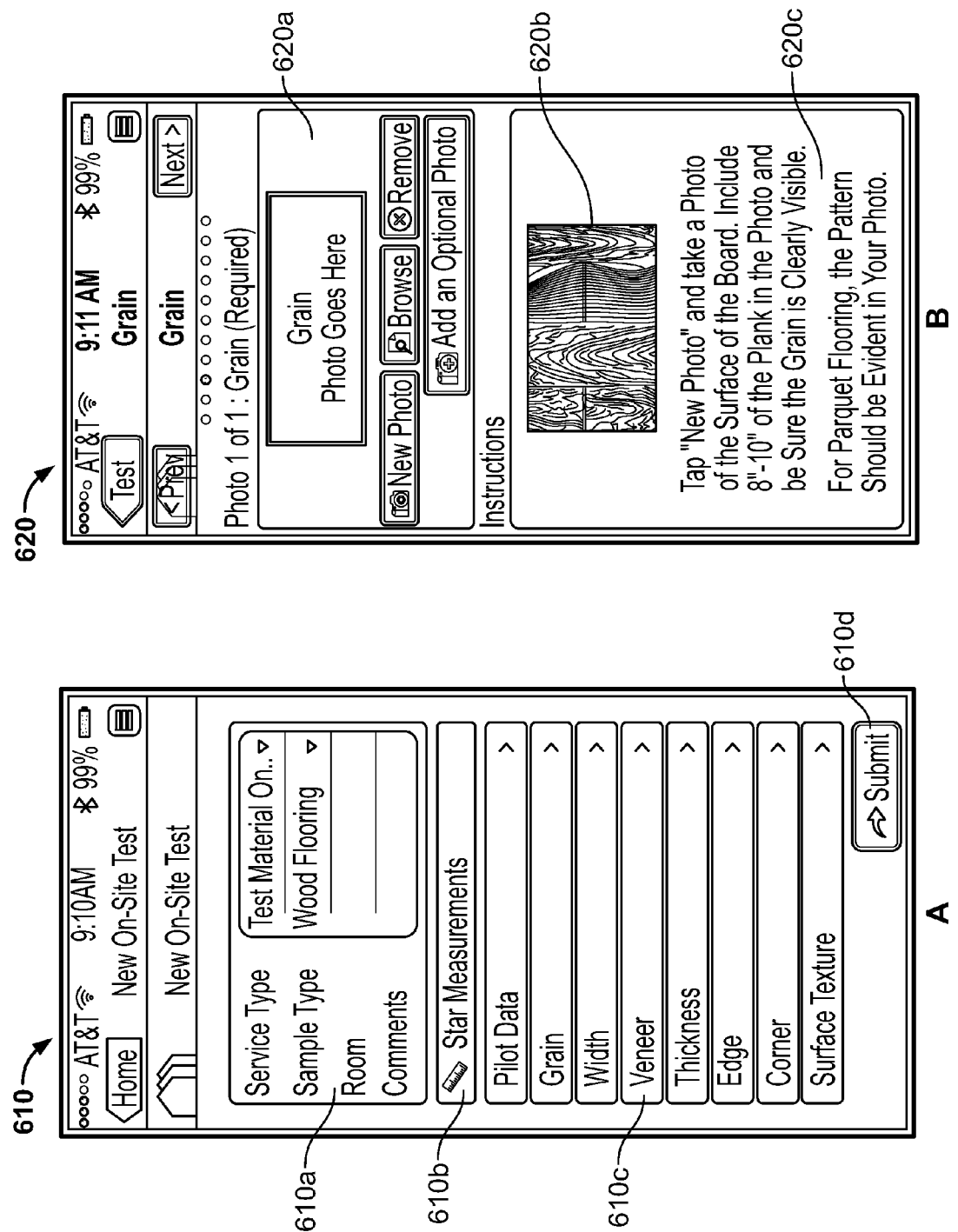
FIG. 6 shows a series of screenshots providing entry of user input and photos for wood flooring acquired from a remote, mobile computing device in accordance with the present disclosure.
Figure 6:
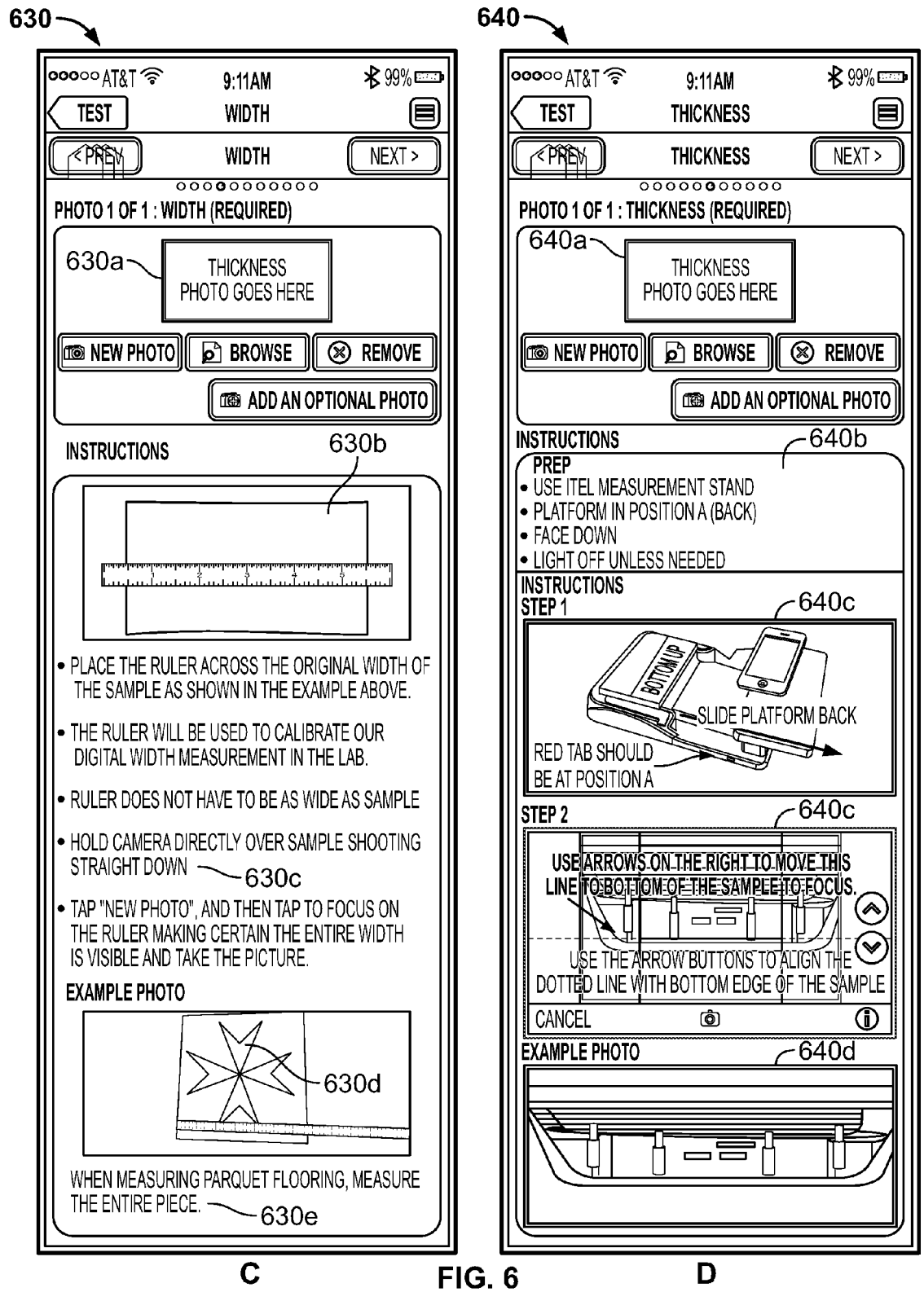

FIG. 6 shows a series of screenshots presenting an input entry interface on a remote, mobile computing device to a user in accordance with the present disclosure. In contrast to a carpet workflows shown above, FIG. 6 depicts a series of screenshots showing entry of user input and photos for wood flooring. In some embodiments, as shown in FIG. 6, a user initiates a new onsite test. FIG. 6A through FIG. 6D shows a new on-site test for wood flooring, including acquisition of information, data, and/or photos of a wood flooring sample.

FIG. 6A shows a screenshot of an app presenting fields for entering information regarding a new on-site test [610]. FIG. 6A shows an input screen so that a user may populate information fields [610a], such as service type, sample type, and room, for example. FIG. 6A shows a button so that a user can initiate taking measurements [610b]. In some embodiments, a user takes a variety of measurements of an unknown sample, such as a wood or parquet flooring sample (as shown herein). In some embodiments, a display on an app prompts a user to take measurements. In some embodiments, screens prompting a user to take measurements are presented one display screen at a time. In some embodiments, user input provided on a preceding screen affects subsequent screen displays to a user. In some embodiments, a user may use an app and a remote, mobile computing device to acquire measurements. In some embodiments, a user may acquire photos of a building material sample adjacent to a measurement device, such as a ruler. In some embodiments, a user may acquire measurements using a separate application on a remote, mobile computing device, for example, a measurement app. In some embodiments, a user may manually acquire measurements and enter each measurement into an app entry screen. FIG. 6A shows exemplary drop down menus that display different building material characteristics for a user to select when describing a sample [610c]. A drop down menu may include, for example, depending on a building material choice a user is evaluating: pilot data, grain, width, veneer, thickness, edge, corner, and/or surface texture. Referring to the bottom of the new onsite test screen [610], is a Submit button [610d]. A submit button [610d] is used to save information, data, and photos before moving to a next screen.

FIG. 6B shows a screenshot of an app presenting fields regarding a wood or parquet flooring sample [620]. FIG. 6B shows options for entering a photo of a wood or parquet flooring sample using a mobile computing device camera [620a]. FIG. 6B shows options including uploading a photo previously taken using for example a mobile computing device camera or another camera. FIG. 6B shows a button to select when a user want to take remove a previously added photo and a button to select when a user want to take additional photos. FIG. 6B shows an example photo to compare a photo a user acquires during acquisition of a photo a wood or parquet flooring sample [620b]. FIG. 6B shows instructions for acquiring at least one photo of a wood or parquet flooring sample [620c].

FIG. 6C shows a screenshot of an app presenting fields regarding a width of a wood or parquet flooring sample [630]. FIG. 6C shows options including taking measurements and at least one photo of a width using a remote, mobile computing device camera [630a]. FIG. 6C shows options including uploading a photo previously taken using for example a remote mobile computing device camera or another camera. FIG. 6C also shows for example options for including additional photos. FIG. 6C shows an example photo and instructions for acquiring measurements for a wood flooring sample using a ruler [630b]. FIG. 6C shows instructions for acquiring a photo of a ruler with a wood flooring sample while acquiring measurements using a ruler [630c]. FIG. 6C shows an example photo and instructions for acquiring measurements for a parquet flooring sample using a ruler [630*d*]. FIG. 6C shows instructions for acquiring a photo of a ruler with a parquet flooring sample while acquiring measurements using a ruler [630*e*].

FIG. 6D shows a screenshot of an app presenting fields regarding a thickness of a wood or parquet flooring sample [640]. FIG. 6D shows options including taking measurements and at least one photo of a width using a mobile computing device camera [640*a*]. FIG. 6D shows options including uploading a photo previously taken using for example a mobile computing device camera or another camera. FIG. 6D shows for example options for including additional photos. FIG. 6D shows instructions for a user to prepare and acquire at least one photo of a wood or parquet flooring sample using a remote, mobile computing device [640*b*]. FIG. 6D provides an illustration of Step 1 and Step 2 showing correct use of an apparatus for collection of a photo of a wood or parquet flooring sample from a remote, mobile client computing device for assignment of value and/or like, kind, and quality assessment of the present disclosure [640*c*]. FIG. 6D shows an example photo to compare with a photo a user acquires during acquisition of a photo of a thickness of a wood or parquet flooring sample [640*d*].

Figure 7:
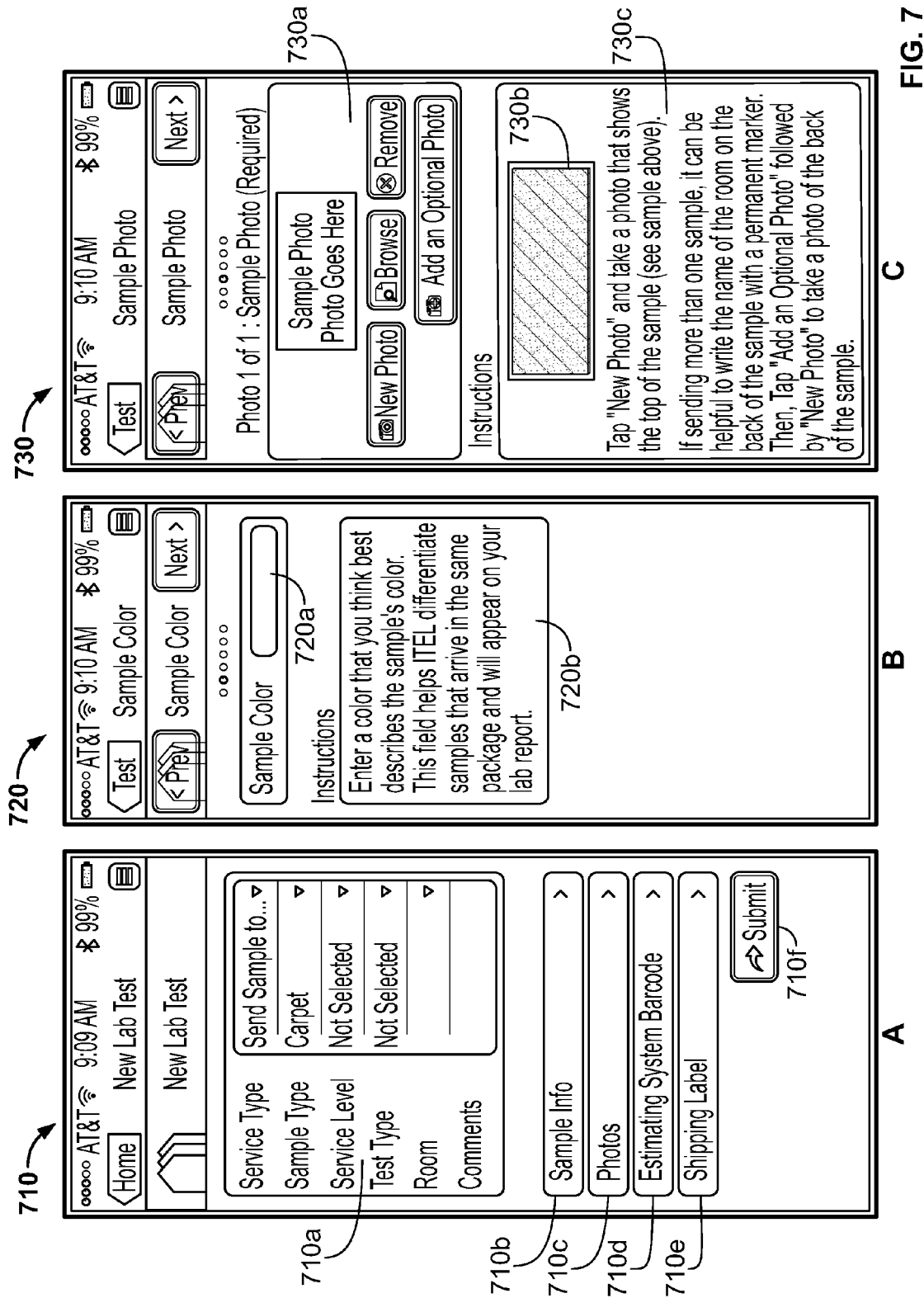
FIG. 7 shows a series of screenshots providing a new lab test entry of user input and photos acquired from a remote, mobile computing device in accordance with the present disclosure and shipping a sample.

FIG. 7 shows screenshots presenting an input entry interface on a remote, mobile computing device to a user in accordance with the present disclosure. FIG. 7 shows a series of screenshots displaying entry of user input and photos acquired from the remote, mobile computing device in accordance with the present disclosure submitted to a service provider computing device for evaluation. In some embodiments, a user will submit multiple samples for evaluation. In some embodiments, multiple physical samples are, for example from physical samples from different rooms. FIG. 7A through FIG. 7C show a new Lab Test order and shipment request for a building material sample.

FIG. 7A shows a screenshot of an app presenting fields regarding a new on-site test [710]. FIG. 7A shows an input screen so that a user may populate information fields [710*a*], such as service type, sample type, and room, for example. FIG. 7A shows a drop down box for entering and/or uploading sample information [710*b*]. FIG. 7A shows a drop down box for entering and/or uploading photos [710*c*]. FIG. 7A also shows a process of initiating shipment of a physical sample. FIG. 7A shows a drop down box for estimating a system barcode [710*d*] (shown in more detail in FIG. 8A). FIG. 7A shows a drop down box for requesting and preparing a shipping label [710*e*] (shown in more detail in FIG. 8B). FIG. 7A shows a Submit button [710*f*] for a user to save information, data, and photos before moving to a next screen.

FIG. 7B shows a screenshot of an app presenting fields regarding identifying a sample that is being shipped [720]. FIG. 7B shows a user entry point where a user may enter a more description so that an offsite analyst receiving multiple physical samples can differentiate physical samples [720*a*]. FIG. 7B also shows instructions to guide a user to enter a more description so that an offsite analyst receiving multiple physical samples can differentiate physical samples [720*b*].

FIG. 7C shows a screenshot of an app presenting fields regarding a photo of a sample for shipment [730]. FIG. 7C shows options including taking a photo of a sample for shipment using a mobile computing device camera [730*a*]. FIG. 7C shows options including uploading a photo previously taken using for example a mobile computing device camera or another camera. FIG. 7C shows for example options for including additional photos. FIG. 7C shows an example photo to compare with a photo a user acquires during acquisition of a photo of a sample for shipment [730*b*]. FIG. 7C shows instructions for a user to prepare and acquire at least one photo of a sample for shipment [730*c*]. FIG. 7C also shows instructions when acquiring at least one photo of more than one sample for shipment when shipping multiple physical samples.

Figure 8:
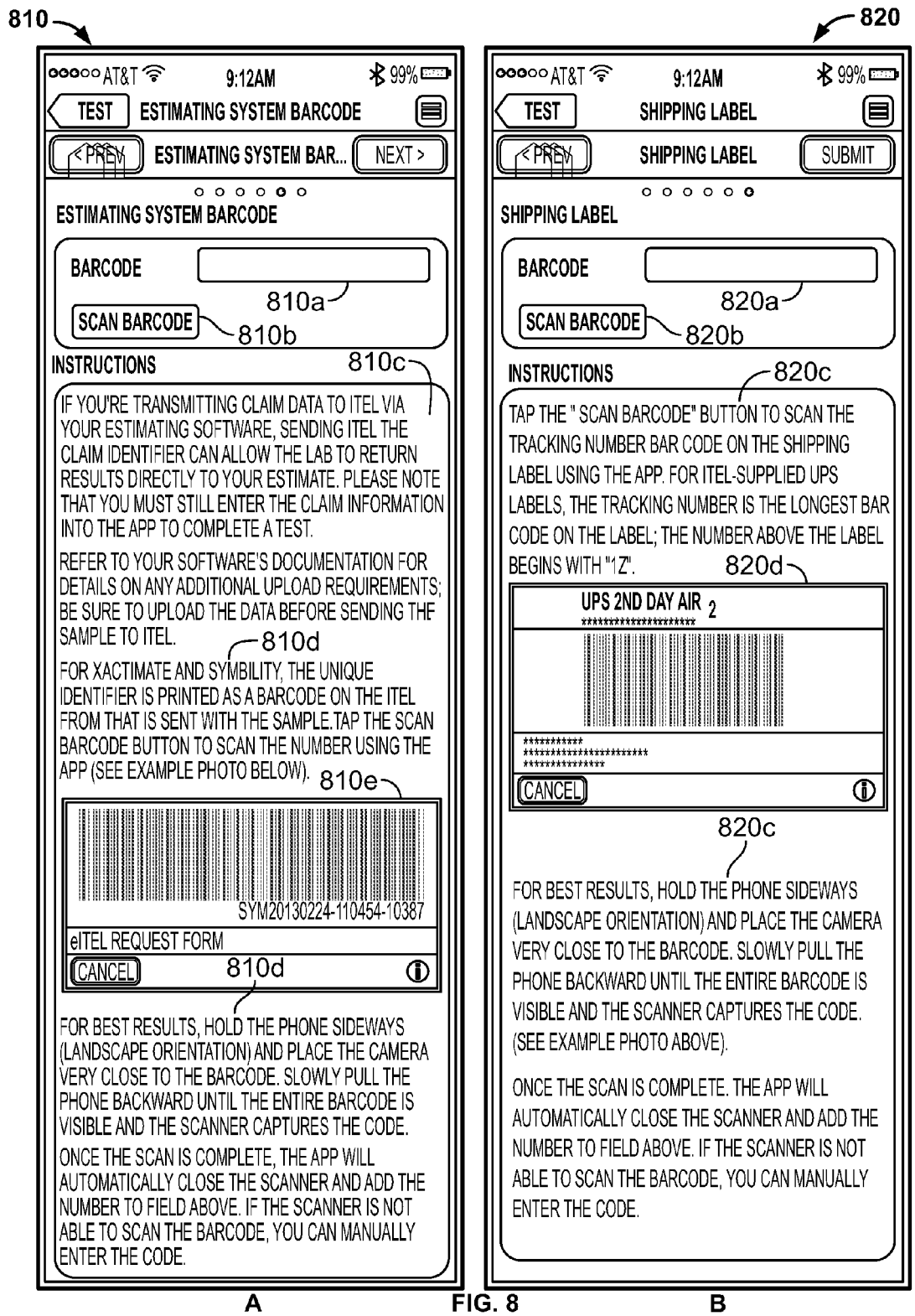
FIG. 8 shows a left screenshot providing acquisition of barcode data corresponding with entry of user input and photos acquired from a remote, mobile computing device in accordance with the present disclosure and a right screenshot showing barcode data corresponding to a shipping carrier label.

FIG. 8 shows screenshots presenting input entry interface on a remote, mobile computing device to a user in accordance with the present disclosure. In some embodiments, an app facilitates submittal of physical samples to a service provider and/or lab, for example if an external lab facility is used for analysis. In some aspects, an app facilitates a submittal of a physical sample without requiring a user to fill out a paper request. In some embodiments, an app allows a user to scan a tracking barcode from a shipping carrier shipping label. This permits a user or service provider with an ability to track a shipment and easily associate claim information, data, and photos with a physical sample sent to the lab.

FIG. 8A depicts screenshots regarding acquisition of barcode data and instructions for acquiring and correlating barcode data [810]. FIG. 8A shows a barcode entry that corresponds with entry of user input, including information, data, and photos acquired with the remote, mobile computing device in accordance with the present disclosure [810*a*]. FIG. 8A shows a barcode field readout [810*a*]. FIG. 8A shows a button that a user may acquire and import a scan using a camera of a remote, mobile computing device [810*b*]. FIG. 8A provides instructions for uploading information, data, and photos and correlating with a barcode on a shipping sample [810*c*]. FIG. 8A shows an example photo to guide a user with using a camera of a remote, mobile computing device for uploading information, data, and photos and correlating with a barcode on a shipping sample [810*e*].

FIG. 8B depicts screenshots regarding acquisition of barcode data and instructions for acquiring and correlating a barcode for shipping data [820]. FIG. 8B shows a barcode entry that corresponds with entry of user input, including information, data, and photos acquired with a remote, mobile computing device in accordance with the present disclosure [820*a*]. FIG. 8B shows a barcode field readout [820*a*]. FIG. 8B shows a button that a user may acquire and import a scan using a camera of a remote, mobile computing device [820*b*]. FIG. 8B provides instructions for acquiring a shipper barcode [820*c*]. FIG. 8B shows an example photo to guide a user with using a camera of a remote, mobile computing device for uploading information, data, and photos and correlating with a barcode on a shipping sample [820*d*].

According to some embodiments, an app is configured with an error detection and correction system to detect incorrect and/or incomplete input and allow a user to correct errors using a same paradigm and screen layout as a user experienced during an initial data entry stage. In some embodiments, error detection and correction allows for immediate and timely corrections to ensure a user receives results as fast as possible. An error correction system is also meta-data driven, providing timely update and dynamic workflow flexibility.

According to some embodiments, an app can work in a disconnected mode or in off line mode. An app operates even though a remote, mobile computing device does not have access to a network, such as the Internet or some other networking environment. An app permits a user to input and 'store and forward' data. An app caches all meta-data instructions providing a general user experience even though a remote, mobile computing device is not connected to the Internet (i.e. offline). In addition, an app maintains a secure login procedure that allows a user to authenticate, even when offline. In some aspects, offline mode will allow a user to enter user input, 'submit' data, and complete error checking and correction functions. So that when internet connection is restored and a user logs into an app or activates an app, saved data is automatically uploaded to a service provider computing device for analysis.

In some implementations, an app contains a question input feature. A question input feature connects a user to an offsite analyst. In some embodiments, an app allows an offsite analyst to post questions to a user. In some embodiments, a user or an offsite analyst poses a question or request. In some embodiments, questions are associated with an appropriate input screen. In some embodiments, an app displays associated screens accompanied with an offsite analyst's question and optional field for a user to respond with text input. For example, an analyst may ask a user to retake a picture because a first photo was received out of focus. When a user completes a response to a question or resubmits requested information, an offsite analyst may complete an analysis. While it is described herein as a text input, it is envisioned that a user-offsite analyst communication connection would be through any means.

According to some embodiments, an app is configured with a dynamic help system directly integrated into the display screen structure. In some implementations, help is always available without navigating off of a current display screen. Additionally, help is cached on a remote, mobile computing device for possible offline use and is automatically updated when help content changes.

Additionally, an app can provide a user with a capability to send a sample to a lab. In some embodiments, a sample is sent to the lab for testing for asbestos, for example. As described above and in further detail below, in some embodiments, an app correlates lab analysis of a physical sample with information, measurement data, and photos sent in by a user.

User Input Workflows

Figure 9:
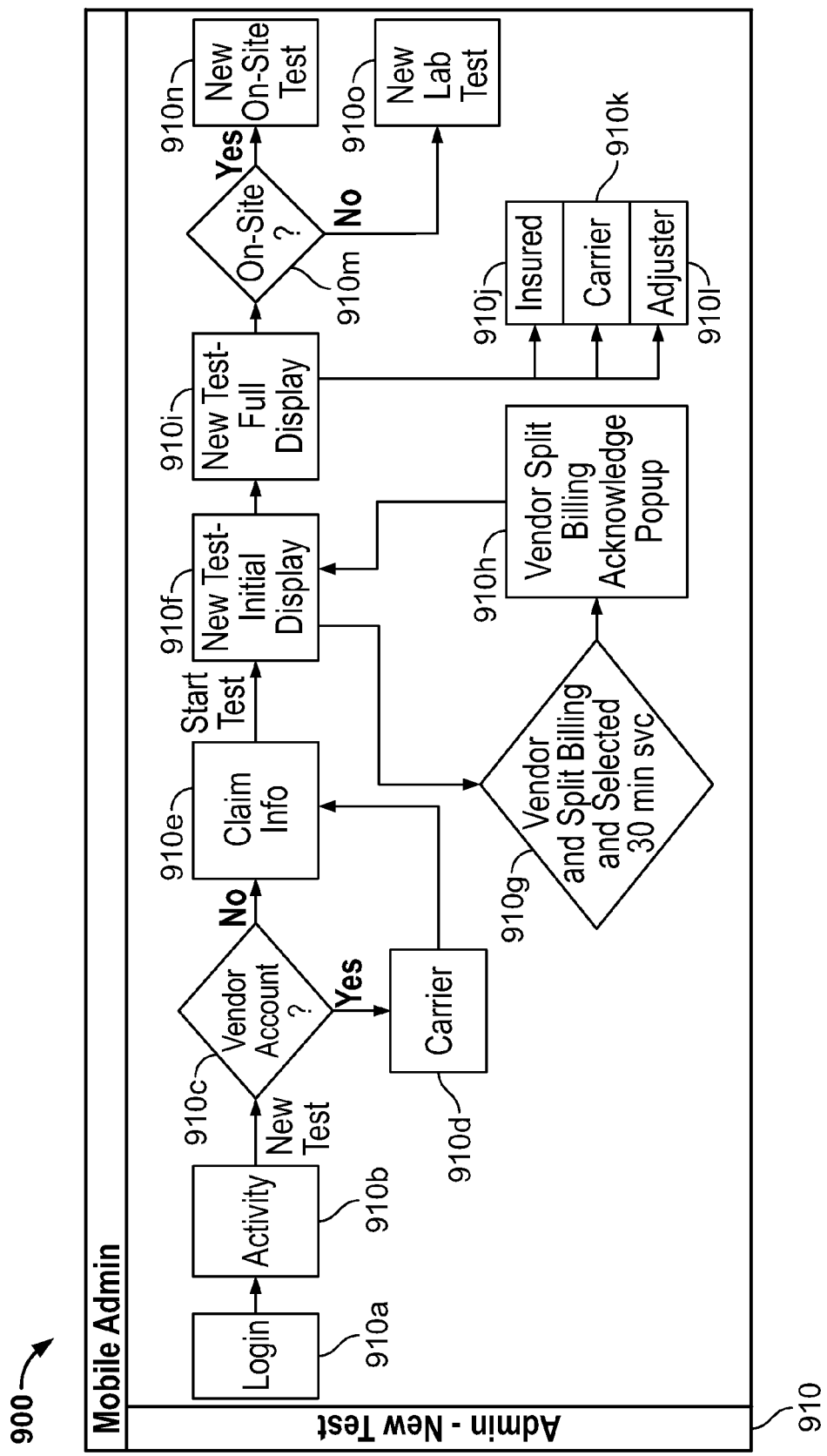
FIG. 9 shows an exemplary logic flow diagram for a new test in accordance with a general method of the present disclosure.

The general workflow method shown in FIG. 1 supports a plurality of unique product workflows. FIG. 9 illustrates a general workflow for a user initiating a new test. In some embodiments, a new test is an onsite test. In some embodiments, a new test is a new lab test.

FIG. 9 illustrates the displays and options for the user using the new on-site and/or new lab test workflow for mobile admin [900]. In some embodiments, workflow [900] is performed using apparatus as described herein. In some embodiments, use of apparatus to perform workflow [900] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows as adaptable, and, thus, these are exemplary. Moreover, the building materials products shown are exemplary and not intended to be limiting.

Referring to the Siding level of the diagram [910], in some embodiments, a user enters login [910a]. In some embodiments, a user indicates an activity, such as a new test [910b]. In some embodiments, a next display screen is a conditional point where a user indicates whether there is a vendor account [910c]. In some embodiments, if a user indicates that there is a vendor account then a user next indicates a carrier [910d]. In some embodiments, a next display or if a user did not indicate that there was a vendor account at [910c] a user enters claim information [910e]. In some embodiments, a user then for example starts a new test. In some embodiments, a new test or initial display [910f] provides a user with options to indicate vendor and split billing and selected 30 minutes service [910g]. In some embodiments, if a user indicates a vendor split billing, then an acknowledgement pops up to confirm [910h]. In some embodiments, after a new test or initial display [910f] is a new test-full display [910i], which provides a user options to enter insured information [910j], carrier information [910k], and/or adjuster information [910l]. In some embodiments, after a new test-full display [910i] a user indicates whether a new test is an on-site test [910m]. A user indicating it is a new on-site test proceeds to a new on-site test [910n]. A user indicating that it is not a new on-site test proceeds to a new lab test [910o].

Figure 10:
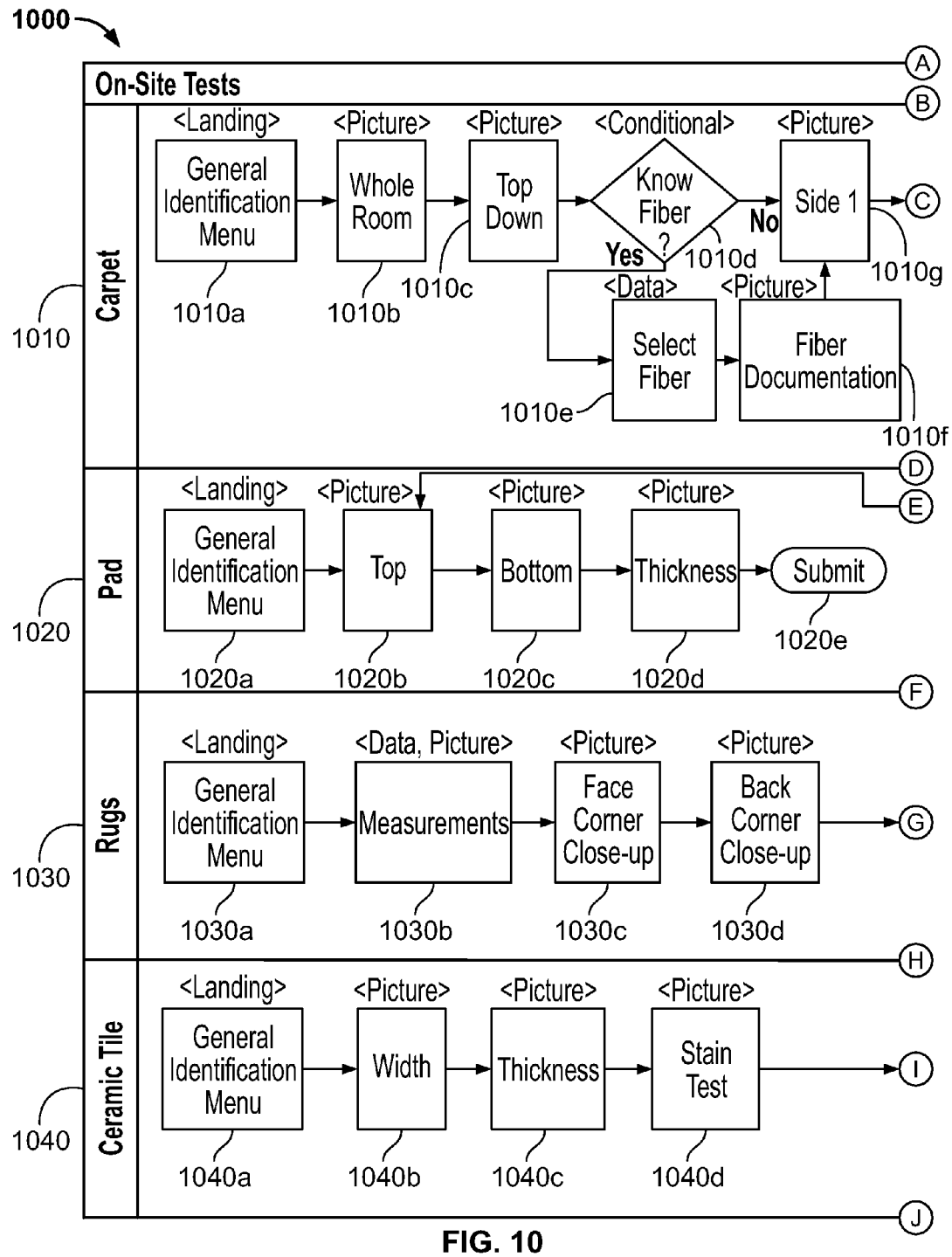
FIG. 10 shows an exemplary logic flow diagram for on-site testing of carpet, carpet pad, rugs, and ceramic tile in accordance with methods of the present disclosure.
Figure 10:
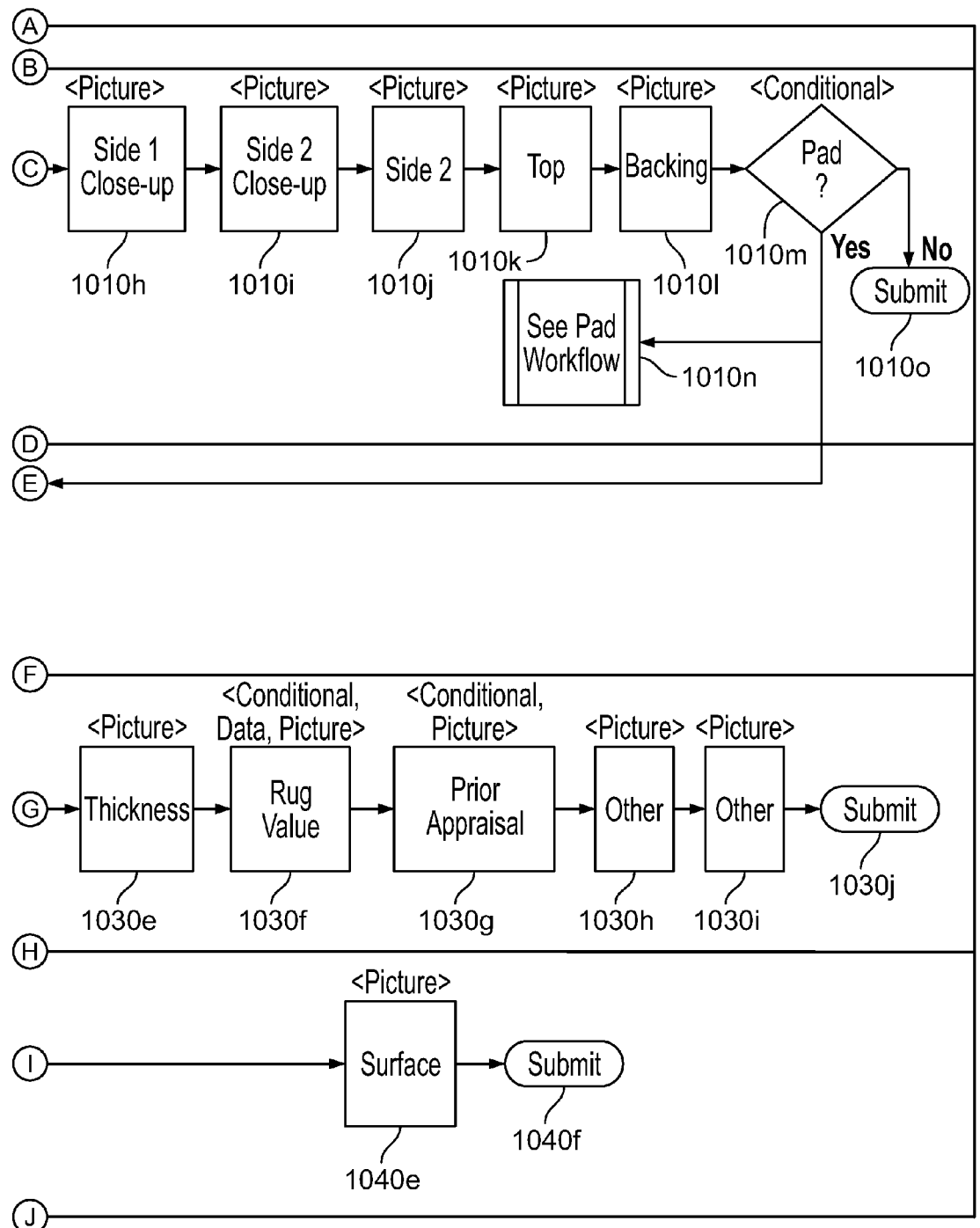
Figure 11:
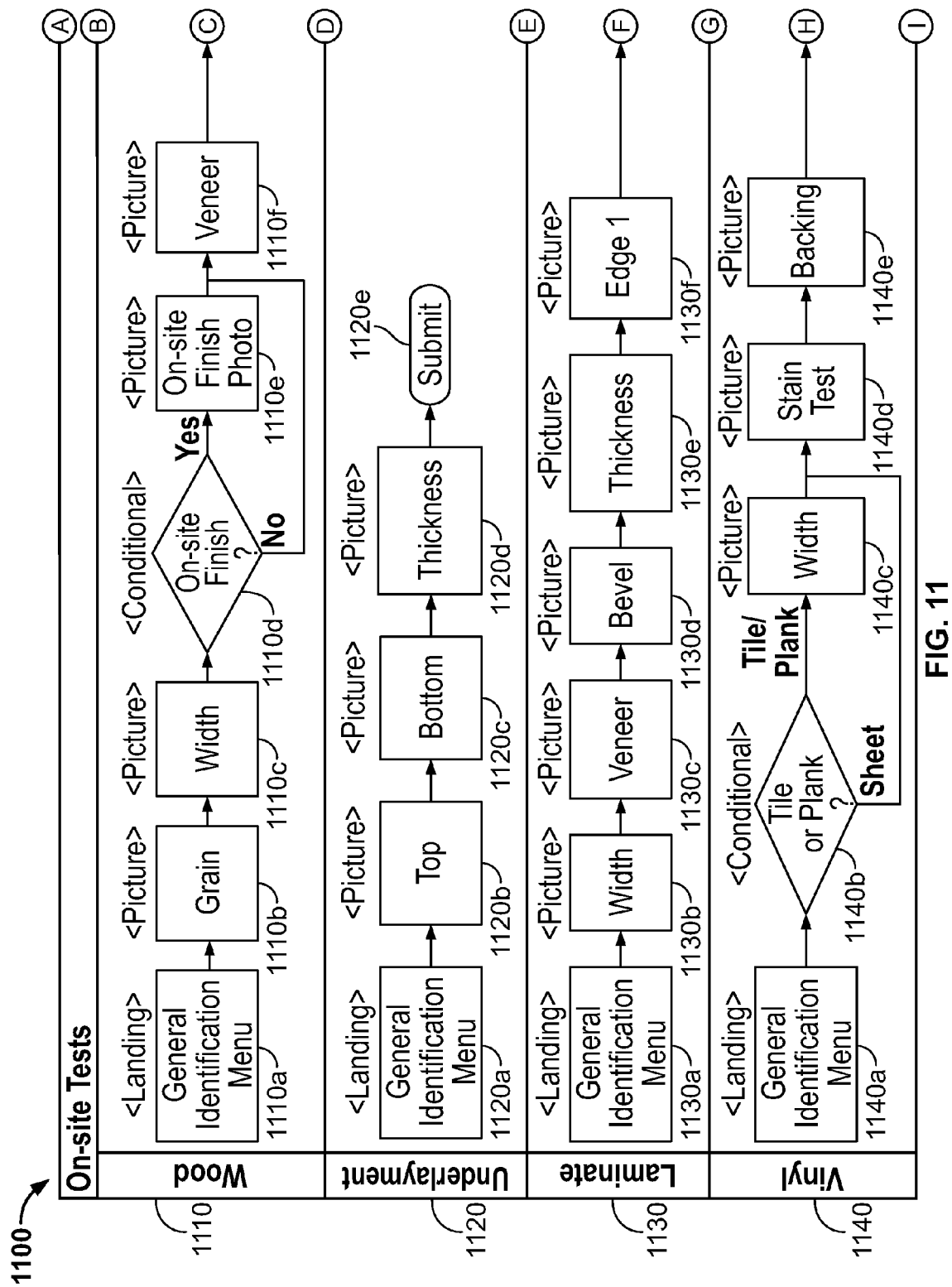
FIG. 11 shows an exemplary logic flow diagram for on-site testing of wood, underlayment, laminate, and vinyl in accordance with methods of the present disclosure.
Figure 11:
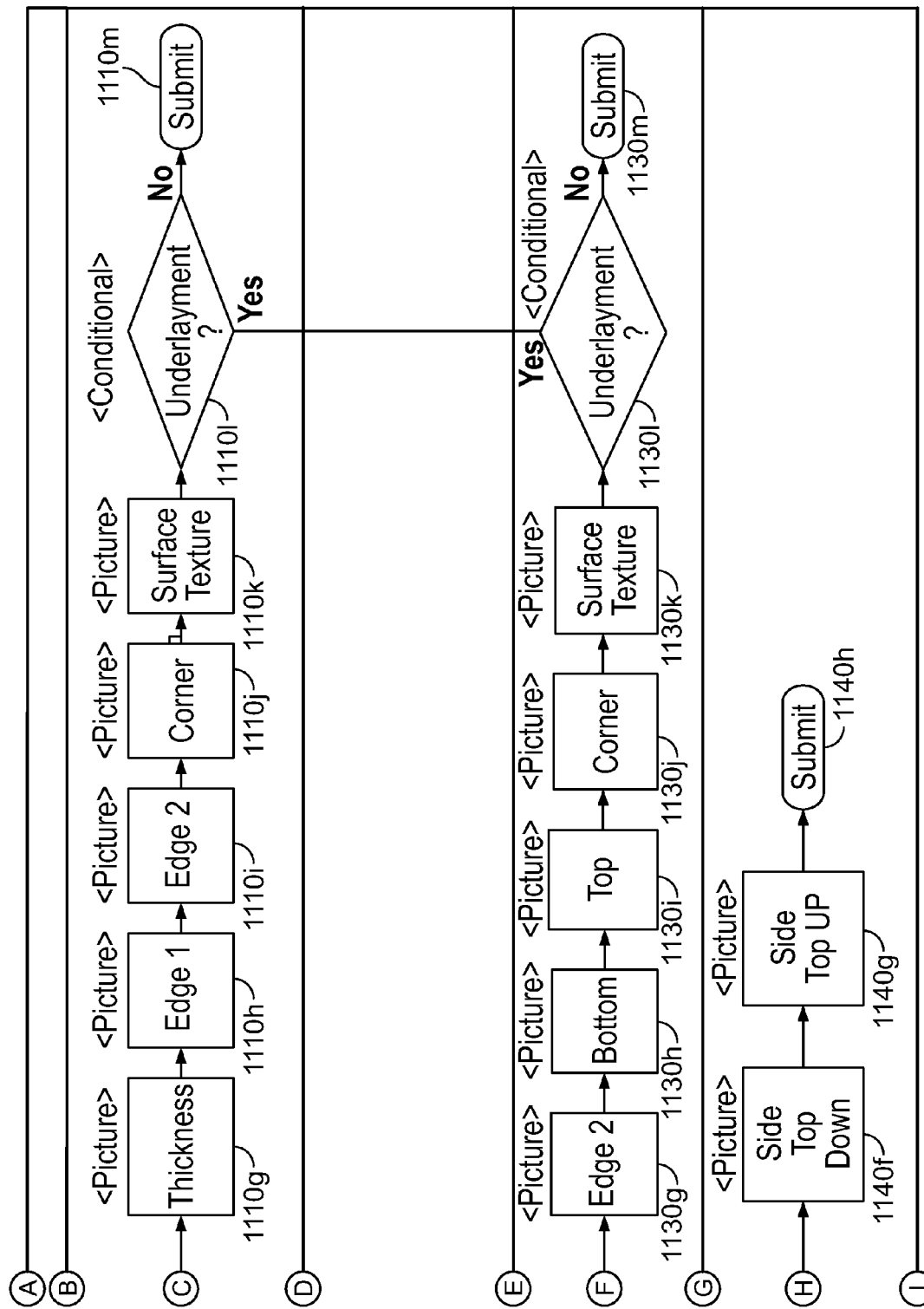
Figure 12:
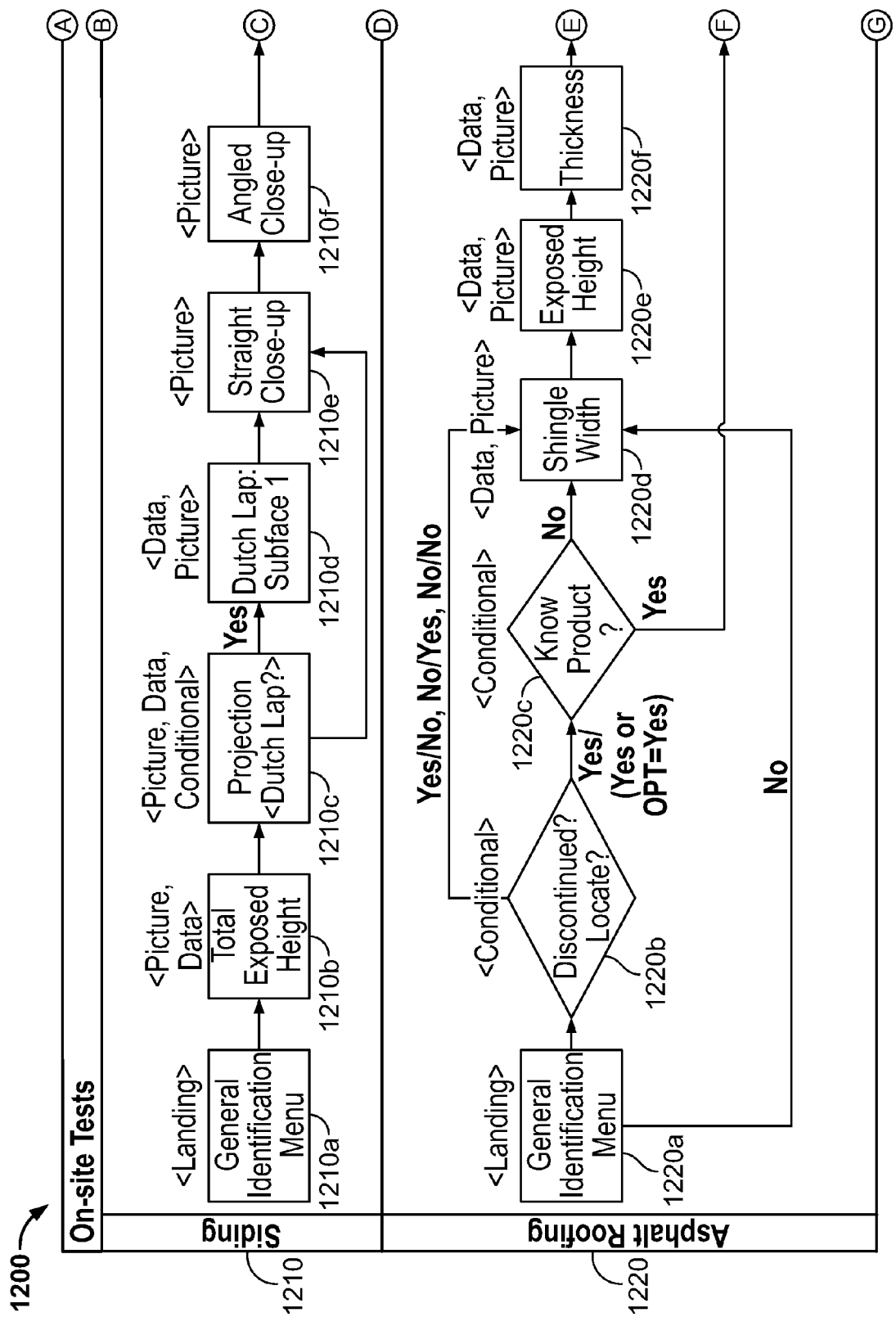
FIG. 12 shows an exemplary logic flow diagram for on-site testing of asphalt roofing and siding products in accordance with methods of the present disclosure.
Figure 12:
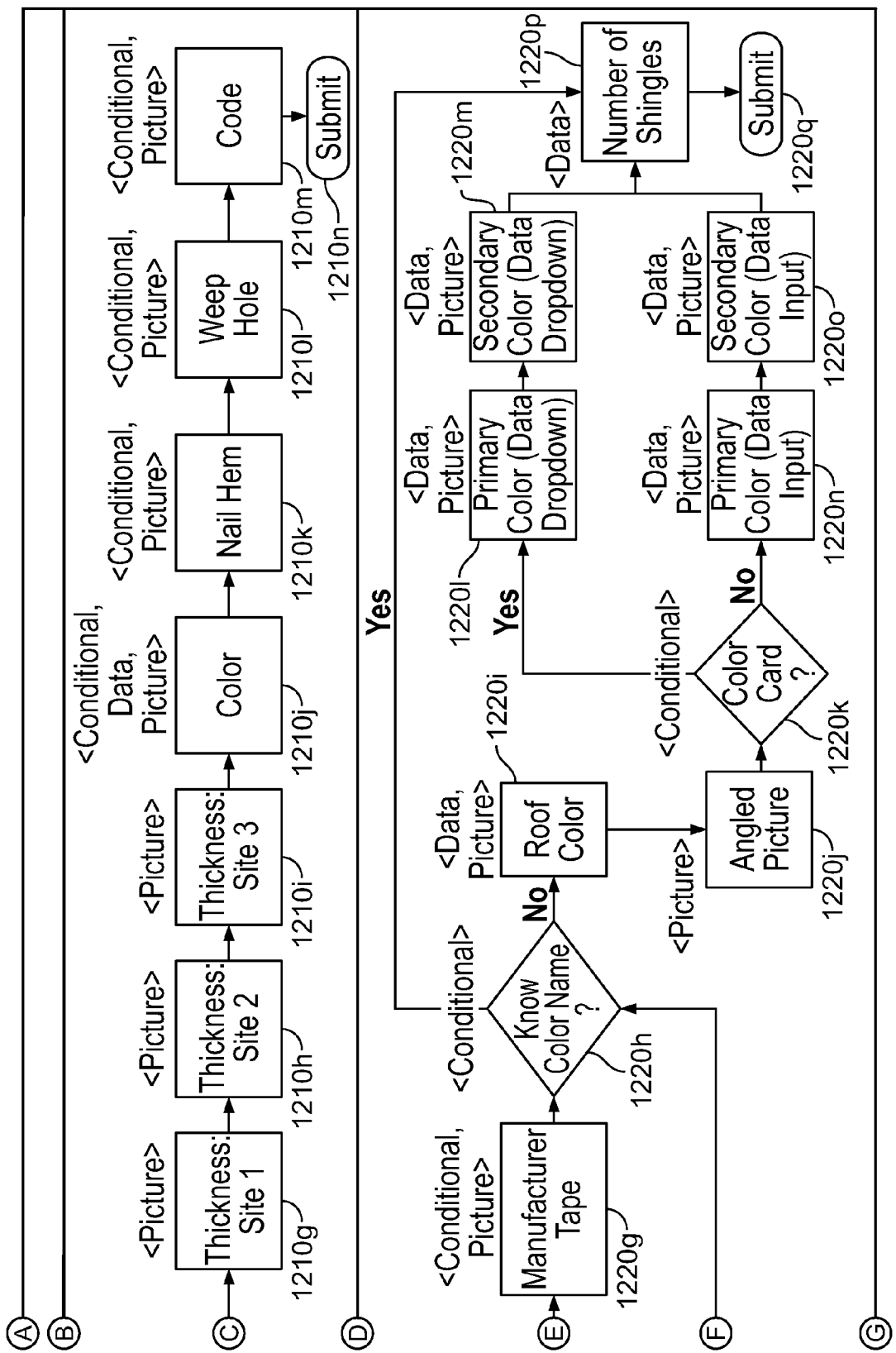

FIG. 10, FIG. 11, and FIG. 12 illustrate ten distinct on-site testing workflows. On site work flows guide the user through display screens and options for various material types.

FIG. 10 illustrates the displays and options for the user using the on-site workflow for carpet, carpet pad, rugs, and ceramic tile [1000]. In some embodiments, workflow is performed using apparatus as described herein. In some embodiments, use of apparatus to perform workflow [1000] is according to the present methods and/or as described herein. As indicated above, in some embodiments, the workflow paradigm of an app of the present disclosure is designed such that it leads a user through an efficient, wizard-style interface. In some aspects, as a user enters information or selects from available choices, such antecedent screen choices affect display screens and choices in subsequent screens. This interface/layout creates a cohesive and consistent input experience for a user.

In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input.

Referring to the Carpet level of the diagram [1010], in some embodiments, a user opens an app to initiate a new on-site test [1010a] and inputs general information regarding a claim and general identification information. In some embodiments, a user will next take a photograph of a whole room of carpet [1010b]. In some embodiments, a user will next takes a photograph showing a carpet from a top down [1010c]. In some embodiments, a next display screen is a conditional point where a user indicates whether a carpet fiber type is known [1010d]. In some embodiments, where a user indicates a carpet fiber type is known, a user selects a fiber type from a list [1010e], for example, in a drop down menu. In some embodiments, where a user then provides an indication of a fiber type, a user uploads fiber documentation [1010f]. In some embodiments, after a user next uploads fiber documentation or where a user does not know a fiber type, a user inputs a photo of a Side 1 of a carpet [1010g]. In some embodiments, a user then takes a close up photograph showing a Side 1 of a carpet [1010h]. In some embodiments, a user then takes a close up photograph showing a Side 2 of a carpet [1010i]. In some embodiments, a user then takes a photograph showing a Side 2 of a carpet [1010j]. In some embodiments, a user then takes a photograph showing a top of a carpet [1010k]. In some embodiments, a user then takes a photograph showing a backing of a carpet [1010l]. In some embodiments, a next display screen is a conditional point where a user indicates whether there is a carpet pad [1010m]. In some embodiments, where a user indicates a carpet pad is present, a user continues [1010n] with a carpet pad workflow [1020]. In some embodiments, where a user indicates a carpet pad is not present a user then submits [1010o] information, data, and photos to a service provider computing device.

Referring to the Pad level of the diagram [1020], in some embodiments, a user opens an app to initiate a new on-site test [1020a] and inputs general information regarding a claim and general identification information. In some embodiments, a user enters the Pad level workflow through a Carpet level workflow where the user has indicated that a carpet pad is present. In some embodiments, takes a photograph showing a carpet from a top down [1020b]. In some embodiments, a user will next take a photograph showing a bottom of a carpet pad [1020c]. In some embodiments, a user then takes a photograph showing a thickness of a carpet pad [1020d]. In some embodiments, a user then submits [1020e] information, data, and photos to a service provider computing device.

Referring to the Rugs level of the diagram [1030], in some embodiments, a user opens an app to initiate a new on-site test [1030a] and inputs general information regarding a claim and general identification information. In some embodiments, a user next acquires measurements of a rug [1030b]. In some embodiments, a user will then take a close up photograph of a front corner of a rug [1030c]. In some embodiments, a user will then take a close up photograph of a back corner of a rug [1030d]. In some embodiments, a user then takes a photograph showing a thickness of a rug [1030e]. In some embodiments, a next display screen is a conditional point where a user indicates whether a rug value, and provides a photo [1030f]. In some embodiments, a next display screen is a conditional point where a user indicates whether there is a prior appraisal and a user inputs a photo [1030g]. In some embodiments, a user then submits [1030j] information, data, and photos to a service provider computing device.

Referring to the Ceramic Tile level of the diagram [1040], in some embodiments, a user opens an app to initiate a test [1040a] and inputs general information regarding a claim and general identification information. In some embodiments, a user next takes a photograph showing a width of a tile [1040b]. In some embodiments, a user next takes a photograph showing a thickness of a tile [1040c]. In some embodiments, a user next takes a photograph showing a stain test of a tile [1040d]. In some embodiments, a user next takes a photograph showing a surface of a tile [1040e]. In some embodiments, a user then submits [1040f] information, data, and photos to a service provider computing device.

FIG. 11, illustrates the displays and options for the user using the on-site workflow for wood, underlayment, laminate, and vinyl [1100]. In some embodiments, workflow is performed using apparatus as described herein. In some embodiments, use of apparatus to perform workflow [1100] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user.

Referring to the Wood level of the diagram [1110], in some embodiments, a user opens an app to initiate a new on-site test [1110a] and inputs general information regarding a claim and general identification information. In some embodiments, a user will next take a photograph of a grain of a wood or parquet floor [1110b]. In some embodiments, a user then takes a photograph of a width of a wood or parquet floor [1110c]. In some embodiments, a next display screen is a conditional point where a user indicates whether a wood or parquet floor has a finish [1110d]. In some embodiments, if a user indicates that a wood or parquet floor has a finish then a user next enters a photograph showing a wood or parquet floor finish [1110e]. In some embodiments, if a user indicates a wood or parquet floor does not have a finish or after a user enters a photo showing a wood or parquet floor finish, a user then enters a photograph of a veneer of a wood or parquet floor [1110f]. In some embodiments, a user then takes a photograph of a thickness of a wood or parquet floor [1110g]. In some embodiments, a user then takes a photograph of a first edge of a wood or parquet floor [1110h]. In some embodiments, a user then takes a photograph of a second edge of a wood or parquet floor [1110i]. In some embodiments, a user then takes a photograph of a corner of a wood or parquet floor [1110j]. In some embodiments, a user then takes a photograph of a surface texture of a wood or parquet floor [1110k]. In some embodiments, a next display screen is a conditional point where a user indicates whether a wood or parquet floor has underlayment [1110l]. In some embodiments, if a user indicates that a wood or parquet floor has underlayment then a user next proceeds to an Underlayment workflow [1120]. In some embodiments, if a user indicates a wood or parquet floor does not have underlayment, then a user submits [1110m] information, data, and photos to a service provider computing device.

Referring to the Underlayment level of the diagram [1120], in some embodiments, a user opens an app to initiate a new on-site test [1120a] and inputs general information regarding a claim and general identification information. In some embodiments, a user enters the Underlayment level workflow through, for example, a Wood [1110] or Laminate [1130] level workflow where the user has indicated that underlayment is present. In some embodiments, a user will next take a photograph of a top of an underlayment [1120b]. In some embodiments, a user then takes a photograph of a bottom of an underlayment [1120c]. In some embodiments, a user then takes a photograph of a thickness of an underlayment

[1110d]. In some embodiments, a user then submits [1120e] information, data, and photos to a service provider computing device.

Referring to the Laminate level of the diagram [1130], in some embodiments, a user opens an app to initiate a new on-site test [1130a] and inputs general information regarding a claim and general identification information. In some embodiments, a user will next take a photograph of a width of a laminate floor [1130b]. In some embodiments, a user then takes a photograph of a veneer of a laminate floor [1130c]. In some embodiments, a user then takes a photograph of a bevel of a laminate floor [1130d]. In some embodiments, a user then takes a photograph of a thickness of a laminate floor [1130e]. In some embodiments, a user then takes a photograph of a first edge of a laminate floor [1130f]. In some embodiments, a user then takes a photograph of a second edge of a laminate floor [1130g]. In some embodiments, a user then takes a photograph of a bottom of a laminate floor [1130h]. In some embodiments, a user then takes a photograph of a top of a laminate floor [1130i]. In some embodiments, a user then takes a photograph of a corner of a laminate floor [1130j]. In some embodiments, a user then takes a photograph of a surface texture of a laminate floor [1130k]. In some embodiments, a next display screen is a conditional point where a user indicates whether a laminate floor has underlayment [1130l]. In some embodiments, if a user indicates that a laminate floor has underlayment then a user next proceeds to an Underlayment workflow [1120]. In some embodiments, if a user indicates a laminate floor does not have underlayment, then a user submits [1130m] information, data, and photos to a service provider computing device.

Referring to the Vinyl level of the diagram [1140], in some embodiments, a user opens an app to initiate a new on-site test [1140a] and inputs general information regarding a claim and general identification information. In some embodiments, a next display screen is a conditional point where a user indicates whether a vinyl floor is tile/plank or sheet [1140b]. In some embodiments, if a user indicates that a vinyl floor is a tile/plank vinyl floor then a user next enters a photograph showing a width of a tile/plank of a tile/plank vinyl floor [1140c]. In some embodiments, if a user indicates a vinyl floor is sheet or after a user enters a photo showing a width of a tile/plank of a tile/plank vinyl floor, a user then enters a photograph of a stain test of a vinyl floor [1140d]. In some embodiments, a user will next take a photograph of a backing of a vinyl floor [1140e]. In some embodiments, a user then takes a photograph of a side of a vinyl floor with a top down [1140f]. In some embodiments, a user then takes a photograph of a side of a vinyl floor with a top up [1140g]. In some embodiments, a user then submits [1140h] information, data, and photos to a service provider computing device.

FIG. 12 illustrates the displays and options for the user using the on-site workflow for siding and asphalt roofing [1200]. In some embodiments, workflow [1200] is performed using apparatus as described herein. In some embodiments, use of apparatus to perform workflow [1200] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows as adaptable, and, thus, these are exemplary. Moreover, the building materials products shown are exemplary and not intended to be limiting.

Referring to the Siding level of the diagram [1210], in some embodiments, a user opens an app to initiate a new on-site test [1210a] and inputs general information regarding a claim and general identification information. In some embodiments, a user will next enter measurements and/or take a photograph of a total exposed height of siding [1210b]. In some embodiments, a next display screen is a conditional point where a user indicates whether a projection of siding is Dutch Lap [1210c]. In some embodiments, if a user indicates that a projection of siding is Dutch Lap then a user next enters a photograph showing a Dutch Lap first surface [1210d]. In some embodiments, if a user indicates a projection of siding is not Dutch Lap or after a user enters a photo showing a Dutch Lap first surface, a user then enters a close up photograph of a straight view of siding [1210e]. In some embodiments, a user then takes an angled close up photograph of siding [1210f]. In some embodiments, a user then takes a photograph of a thickness of a Side 1 of siding [1210g]. In some embodiments, a user then takes a photograph of a thickness of a Side 2 of siding [1210h]. In some embodiments, a user then takes a photograph of a thickness of a Side 3 of siding [1210i]. In some embodiments, a next display screen is a conditional point where a user may provide data and/or a photograph to indicate a color of siding [1210j]. In some embodiments, a next display screen is a conditional point where a user may provide a photograph showing a nail helm of siding [1210k]. In some embodiments, a next display screen is a conditional point where a user may provide a photograph showing a weep hole of siding [1210l]. In some embodiments, a next display screen is a conditional point where a user may provide a photograph showing a code of siding [1210m]. In some embodiments, a user then submits [1210n] information, data, and photos to a service provider computing device.

Referring to the Asphalt Roofing level of the diagram [1220], in some embodiments, a user opens an app to initiate a new on-site test [1220a] and inputs general information regarding a claim and general identification information. In some embodiments, a next display screen is a conditional point where a user indicates first whether asphalt roofing was discontinued and whether asphalt roofing could be located [1220b]. In some embodiments, if a user indicates that asphalt roofing was discontinued and locatable, then at a next step a user must indicate whether asphalt roofing is a known product [1220c]. In some embodiments, if a user indicates that asphalt roofing was discontinued, locatable, but not known or a user previously indicated [1220b] either that asphalt roofing was discontinued and not locatable, not discontinued and locatable, or not discontinued and not locatable, then in some embodiments, a user enters data indicating a shingle width and takes a photograph showing a shingle width for asphalt roofing [1220d]. In some embodiments, a user then enters data indicating an exposed height of asphalt roofing and takes a photograph of an exposed height of asphalt roofing [1220e]. In some embodiments, a user then enters data indicating a thickness of asphalt roofing and takes a photograph of a thickness of asphalt roofing [1220*f*]. In some embodiments, a next display screen is a conditional point where a user may indicate a manufacturer type and/or takes a photograph of a manufacturer type of asphalt roofing [1220*g*]. In some embodiments, a next display screen or after a user had indicated that asphalt roofing was discontinued, locatable, and known [1220*d*], is a conditional point where a user may indicate a known color of asphalt roofing [1220*h*]. In some embodiments, if a user does not indicate a color of asphalt roofing, then a user next enters a photograph showing a color of asphalt roofing [1220*i*]. In some embodiments, if a user does not indicate a color of asphalt roofing, then a user next enters an angled photograph showing asphalt roofing [1220*j*]. In some embodiments, a next display screen is a conditional point where a user indicates whether a color card of asphalt roofing is known [1220*k*]. In some embodiments, if a user indicates that a color card of asphalt roofing is known then a user next enters data regarding a primary color, for example, using a drop down menu that provides a listing of primary colors and takes a photograph showing a primary color [1220*l*]. In some embodiments, a user next enters data regarding a secondary color, for example, using a drop down menu that provides a listing of secondary colors and takes a photograph showing a secondary color [1220*m*]. In some embodiments, if a user indicates that a color card of asphalt roofing is not known then a user next enters data regarding a primary color and takes a photograph showing a primary color [1220*n*]. In some embodiments, a user next enters data regarding a secondary color and takes a photograph showing a secondary color [1220*o*]. In some embodiments, a next step proceeding after either [1220*o*] or [1220*m*] or from [1220*h*] where a color name is known a user enters data indicating a number of shingles [1220*p*]. In some embodiments, a user then submits [1220*q*] information, data, and photos to a service provider computing device.

FIG. 13, FIG. 14, FIG. 15, and FIG. 16 illustrate eleven distinct new lab test submittal workflows. Lab submittal workflows guide the user display screens and options for submitting information, data, photos, and physical samples to the service provider.

Figure 13:
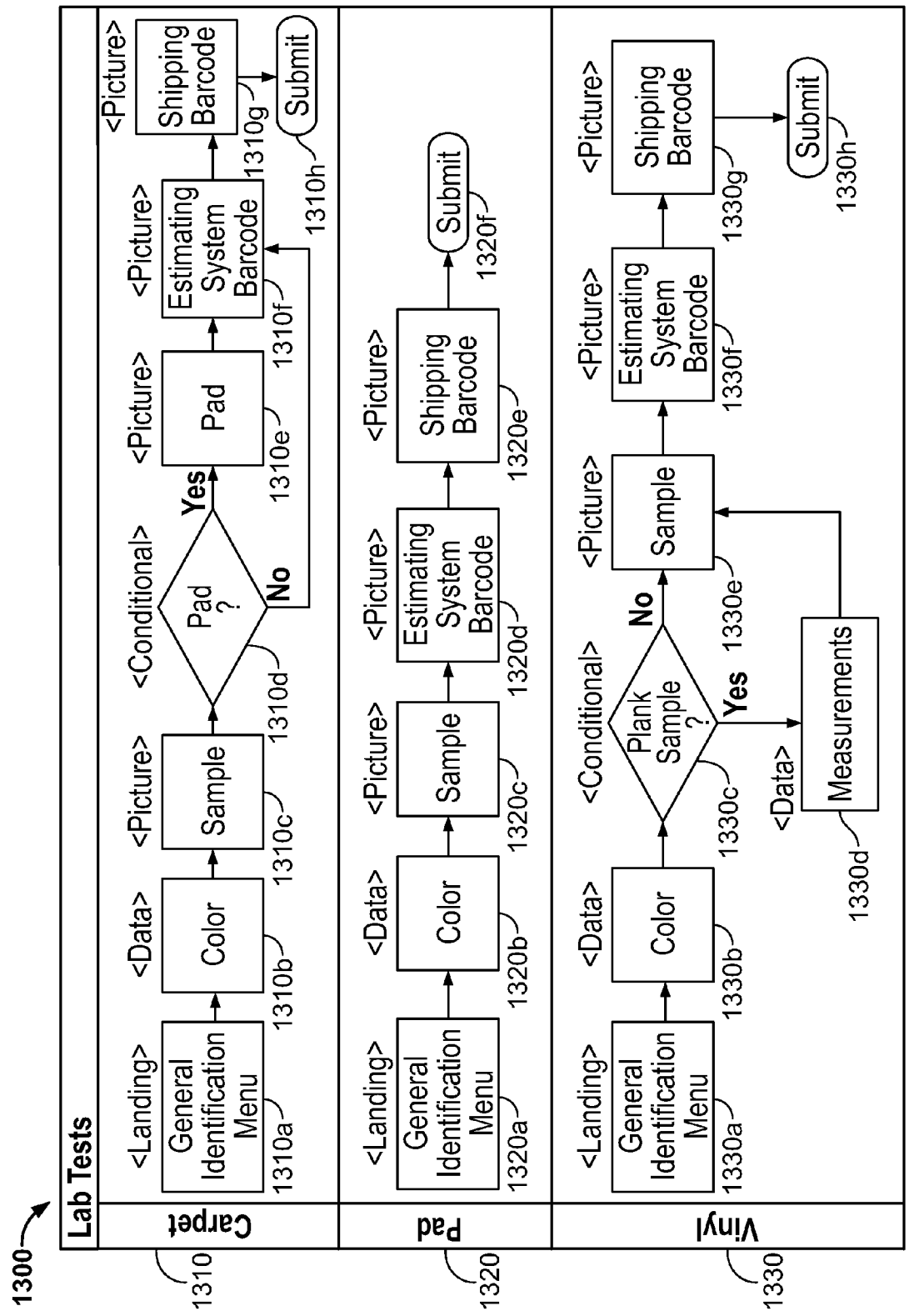
FIG. 13 shows an exemplary logic flow diagram for submitting a sample for lab testing and analysis of carpet, carpet pad, and vinyl in accordance with methods of the present disclosure.

FIG. 13 illustrates the displays and options for a user using a new lab test submittal workflow for carpet, carpet pad, and vinyl [1300]. In some embodiments, workflow [1300] is performed using apparatus as described herein. In some embodiments, use of apparatus to perform workflow [1300] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows are adaptable, and, thus, these are exemplary. Moreover, the building materials products shown are exemplary and not intended to be limiting.

Referring to the Carpet level of the diagram [1310], in some embodiments, a user opens an app to initiate a new lab test [1310*a*] and inputs general information regarding a claim and general identification information. In some embodiments, a user will next enter data indicating a color of a carpet [1310*b*]. In some embodiments, a user next takes a photograph showing a carpet [1310*c*]. In some embodiments, a next display screen is a conditional point where a user indicates whether there is a carpet pad [1310*d*]. In some embodiments, if a user indicates that there is a carpet pad then a user next enters a photograph showing a carpet pad [1310*e*]. In some embodiments, if a user indicates there is no carpet pad or after a user enters a photo showing a carpet pad, a user then enters a photograph estimating system barcode [1310*f*]. In some embodiments, a user next takes a photograph showing a shipping barcode [1310*g*]. In some embodiments, a user then submits [1310*h*] information, data, and photos to a service provider computing device.

Referring to the Pad level of the diagram [1320], in some embodiments, a user opens an app to initiate a new lab test [1320*a*] and inputs general information regarding a claim and general identification information. In some embodiments, a user will next enter data indicating a color of a carpet pad [1320*b*]. In some embodiments, a user next takes a photograph showing a carpet pad [1320*c*]. In some embodiments, a user then enters a photograph estimating system barcode [1320*d*]. In some embodiments, a user next takes a photograph showing a shipping barcode [1320*e*]. In some embodiments, a user then submits [1320*f*] information, data, and photos to a service provider computing device.

Referring to the Vinyl level of the diagram [1330], in some embodiments, a user opens an app to initiate a new lab test [1330*a*] and inputs general information regarding a claim and general identification information. In some embodiments, a user will next enter data indicating a color of a carpet [1330*b*]. In some embodiments, a next display screen is a conditional point where a user indicates whether vinyl flooring has planks [1330*c*]. In some embodiments, if a user indicates that there is a vinyl sample having planks, then a user next enters measurements of a vinyl sample having planks [1330*d*]. In some embodiments, if a user indicates there are no planks or after a user enters measurements of a vinyl sample having planks, a user next enters a photograph showing vinyl flooring [1330*e*]. In some embodiments, a user then enters a photograph estimating system barcode [1330*f*]. In some embodiments, a user next takes a photograph showing a shipping barcode [1330*g*]. In some embodiments, a user then submits [1330*h*] information, data, and photos to a service provider computing device.

Figure 14:
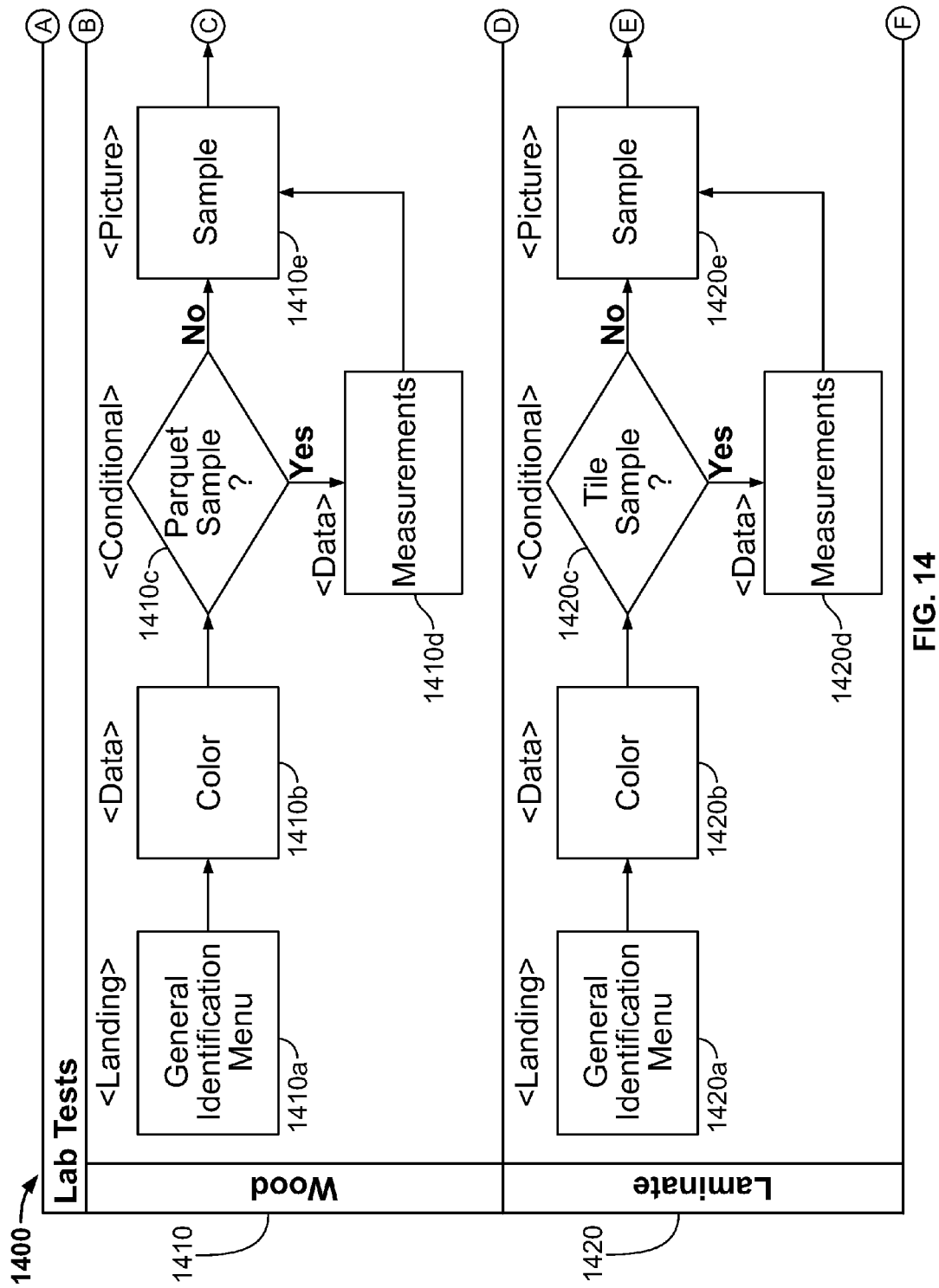
FIG. 14 shows an exemplary logic flow diagram for submitting a sample for lab testing and analysis of laminate and wood flooring products in accordance with methods of the present disclosure.
Figure 14:
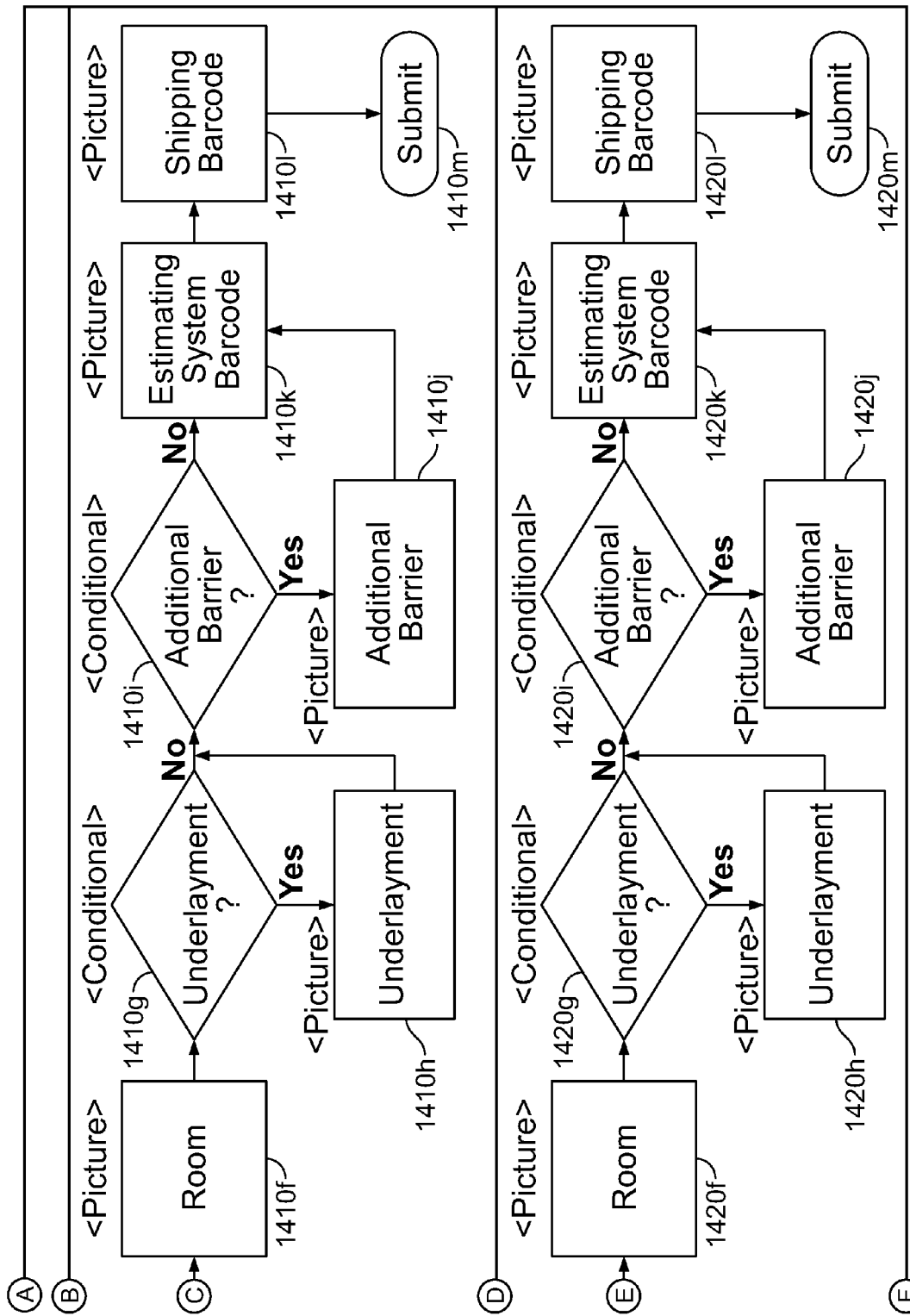

FIG. 14, illustrates the displays and options for a user using a new lab test submittal workflow for wood and laminate [1400]. In some embodiments, workflow [1400] is performed using apparatus as described herein. In some embodiments, use of apparatus to perform workflow [1400] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows as adaptable, and, thus, these are exemplary. Moreover, the building materials products shown are exemplary and not intended to be limiting.

Referring to the Wood level of the diagram [1410], in some embodiments, a user opens an app to initiate a new lab test [1410a] and inputs general information regarding a claim and general identification information. In some embodiments, a user will next enter data indicating a color of wood flooring [1410b]. In some embodiments, a next display screen is a conditional point where a user indicates whether wood flooring is a parquet floor [1410c]. In some embodiments, if a user indicates that wood flooring is a parquet floor, then a user next enters measurements of a parquet wood floor [1410d]. In some embodiments, if a user indicates a wood floor is not a parquet floor or after a user enters measurements of a parquet floor, a user next enters a photograph showing a wood floor [1410e]. In some embodiments, a user then enters a photograph of a whole room of wood floor [1410f]. In some embodiments, a next display screen is a conditional point where a user indicates whether there is underlayment [1410g]. In some embodiments, if a user indicates that there is underlayment then a user next enters a photograph showing underlayment [1410h]. In some embodiments, if a user indicates there is no underlayment or after a user enters a photo underlayment, then a next display screen is a conditional point where a user indicates whether there is an additional barrier [1410i]. In some embodiments, if a user indicates that there is an additional barrier then a user next enters a photograph showing an additional barrier [1410j]. In some embodiments, if a user indicates there is no an additional barrier or after a user enters a photo showing an additional barrier, a user then enters a photograph estimating system barcode [1410k]. In some embodiments, a user next takes a photograph showing a shipping barcode [1410l]. In some embodiments, a user then submits [1410m] information, data, and photos to a service provider computing device.

Referring to the Laminate level of the diagram [1420], in some embodiments, a user opens an app to initiate a new lab test [1420a] and inputs general information regarding a claim and general identification information. In some embodiments, a user will next enter data indicating a color of laminate flooring [1420b]. In some embodiments, a next display screen is a conditional point where a user indicates whether laminate flooring is a tile laminate floor [1420c]. In some embodiments, if a user indicates that laminate flooring is a tile laminate floor, then a user next enters measurements of a tile laminate floor [1420d]. In some embodiments, if a user indicates a laminate floor is not a tile laminate floor or after a user enters measurements of a tile laminate floor, a user next enters a photograph showing a laminate floor [1420e]. In some embodiments, a user then enters a photograph of a whole room of laminate floor [1420f]. In some embodiments, a next display screen is a conditional point where a user indicates whether there is underlayment [1420g]. In some embodiments, if a user indicates that there is underlayment then a user next enters a photograph showing underlayment [1420h]. In some embodiments, if a user indicates there is no underlayment or after a user enters a photo underlayment, then a next display screen is a conditional point where a user indicates whether there is an additional barrier [1420i]. In some embodiments, if a user indicates that there is an additional barrier then a user next enters a photograph showing an additional barrier [1420j]. In some embodiments, if a user indicates there is no an additional barrier or after a user enters a photo showing an additional barrier, a user then enters a photograph estimating system barcode [1420k]. In some embodiments, a user next takes a photograph showing a shipping barcode [1420l]. In some embodiments, a user then submits [1420m] information, data, and photos to a service provider computing device.

Figure 15:
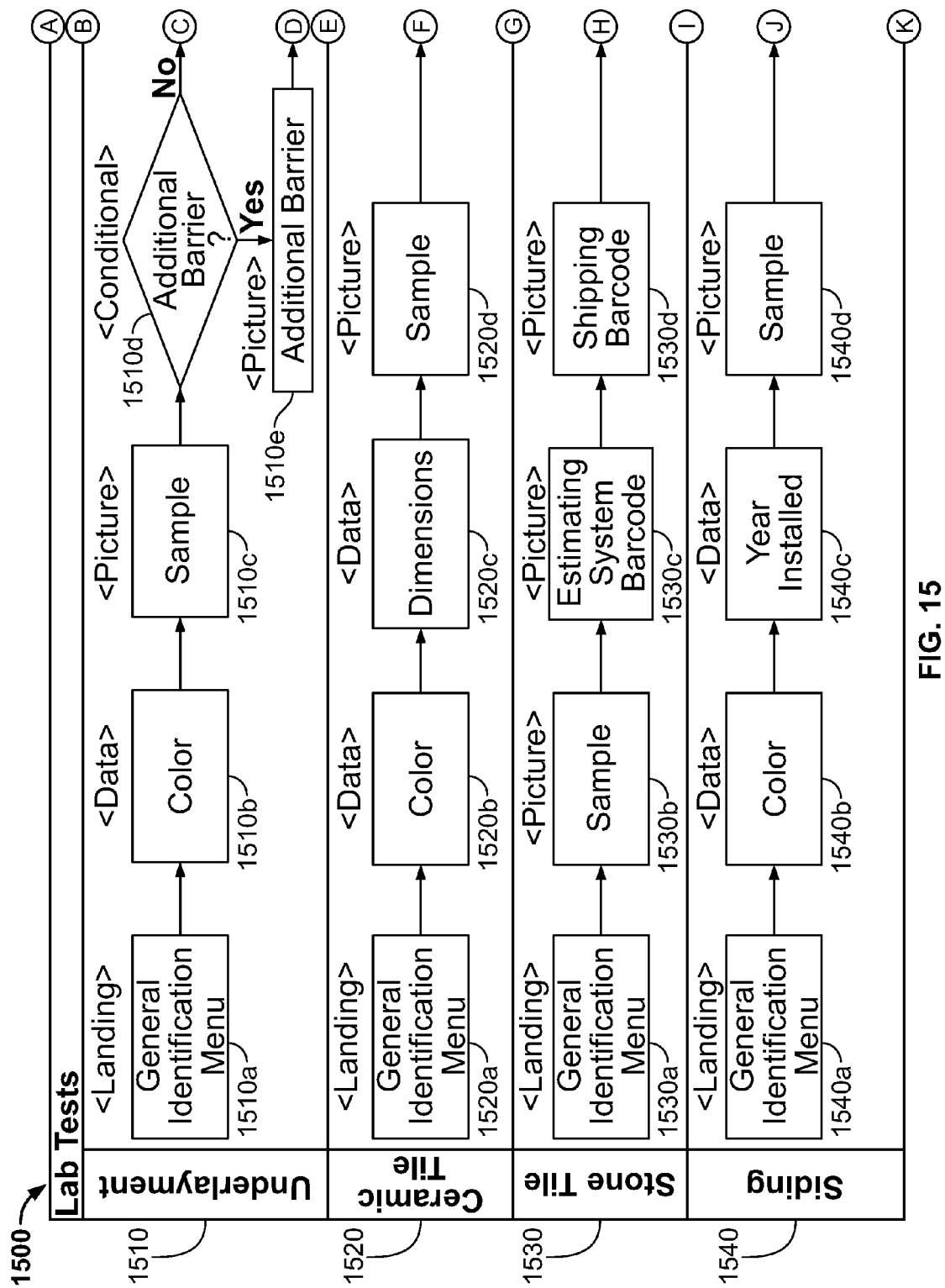
FIG. 15 shows an exemplary logic flow diagram for submitting a sample for lab testing and analysis of underlayment, ceramic tile, stone tile, and siding products in accordance with methods of the present disclosure.
Figure 15:
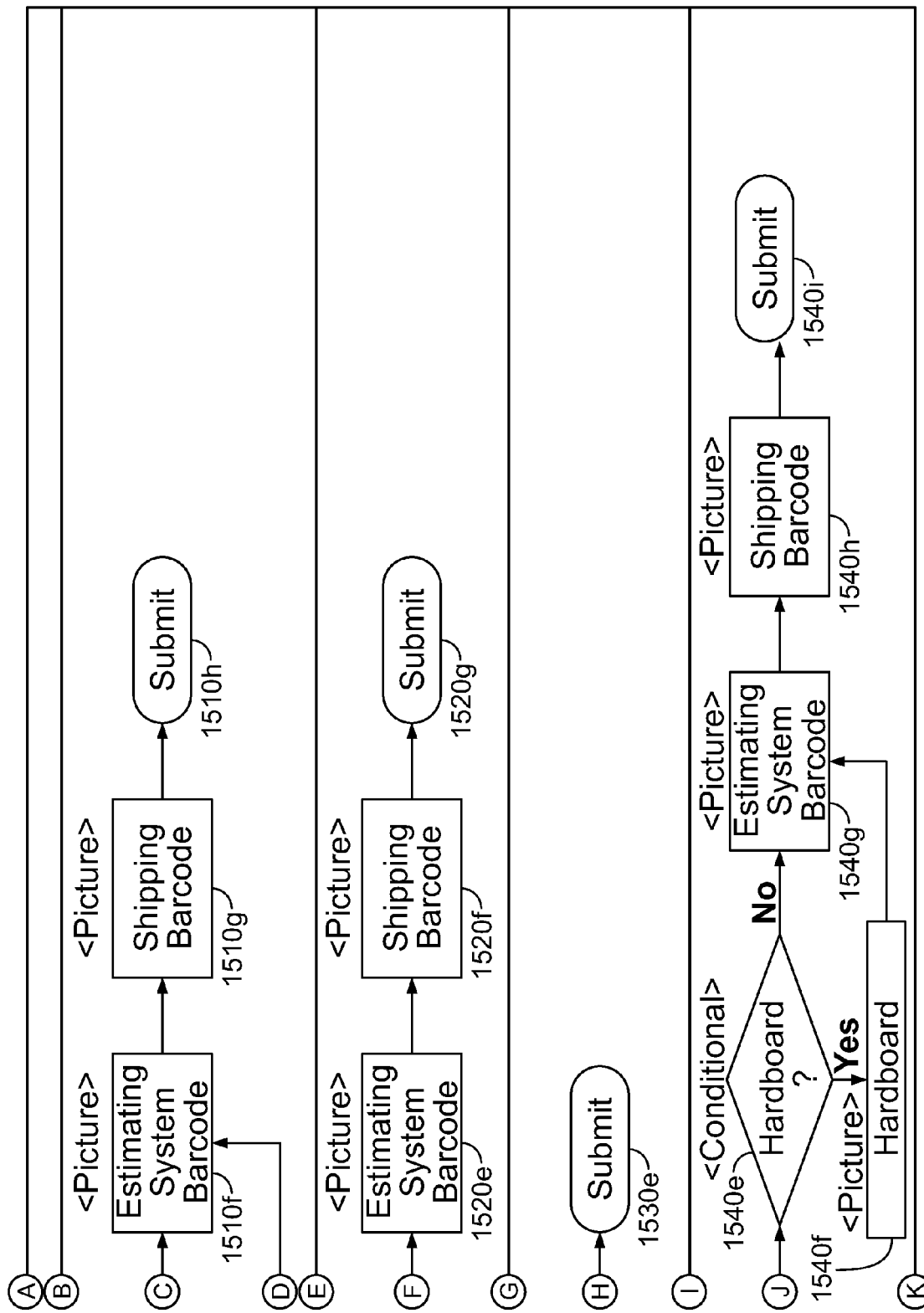

FIG. 15 illustrates the displays and options for a user using a new lab test submittal workflow for underlayment, ceramic tile, stone tile, and siding [1500]. In some embodiments, workflow [1500] is performed using apparatus as described herein. In some embodiments, use of apparatus to perform workflow [1500] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows as adaptable, and, thus, these are exemplary. Moreover, the building materials products shown are exemplary and not intended to be limiting.

Referring to the Underlayment level of the diagram [1510], in some embodiments, a user opens an app to initiate a new lab test [1510a] and inputs general information regarding a claim and general identification information. In some embodiments, a user will next enter data indicating a color of underlayment [1510b]. In some embodiments, a user then enters a photograph showing underlayment [1510c]. In some embodiments, a next display screen is a conditional point where a user indicates whether there is an additional barrier [1510d]. In some embodiments, if a user indicates that there is an additional barrier, then a user next enters a photograph showing an additional barrier [1510e]. In some embodiments, if a user indicates there is no an additional barrier or after a user enters a photo showing an additional barrier, a user then enters a photograph estimating system barcode [1510f]. In some embodiments, a user next takes a photograph showing a shipping barcode [1510g]. In some embodiments, a user then submits [1510h] information, data, and photos to a service provider computing device.

Referring to the Ceramic Tile level of the diagram [1520], in some embodiments, a user opens an app to initiate a new lab test [1520a] and inputs general information regarding a claim and general identification information. In some embodiments, a user will next enter data indicating a color of ceramic tile [1520b]. In some embodiments, a user will next enter data indicating dimensions of ceramic tile [1520c]. In some embodiments, a user then enters a photograph showing ceramic tile [1520d]. In some embodiments, a user then enters a photograph estimating system barcode [1520e]. In some embodiments, a user next takes a photograph showing a shipping barcode [1520f]. In some embodiments, a user then submits [1520g] information, data, and photos to a service provider computing device.

Referring to the Stone Tile level of the diagram [1530], in some embodiments, a user opens an app to initiate a new lab test [1530a] and inputs general information regarding a claim and general identification information. In some embodiments, a user then enters a photograph showing stone tile [1530b]. In some embodiments, a user then enters a photograph estimating system barcode [1530c]. In some embodiments, a user next takes a photograph showing a shipping barcode [1530d]. In some embodiments, a user then submits [1530e] information, data, and photos to a service provider computing device.

Referring to the Siding level of the diagram [1540], in some embodiments, a user opens an app to initiate a new lab test [1540a] and inputs general information regarding a claim and general identification information. In some embodiments, a user will next enter data indicating a siding color [1540b]. In some embodiments, a user will next enter data indicating a year siding was installed [1540c]. In some embodiments, a user then enters a photograph of siding [1540d]. In some embodiments, a next display screen is a conditional point where a user indicates whether there is hardboard [1540e]. In some embodiments, if a user indicates that there is hardboard, then a user next enters a photograph showing hardboard [1540f]. In some embodiments, if a user indicates there is no hardboard or after a user enters a photo showing hardboard, a user then enters a photograph estimating system barcode [1540g]. In some embodiments, a user next takes a photograph showing a shipping barcode [1540h]. In some embodiments, a user then submits [1540i] information, data, and photos to a service provider computing device.

Figure 16:
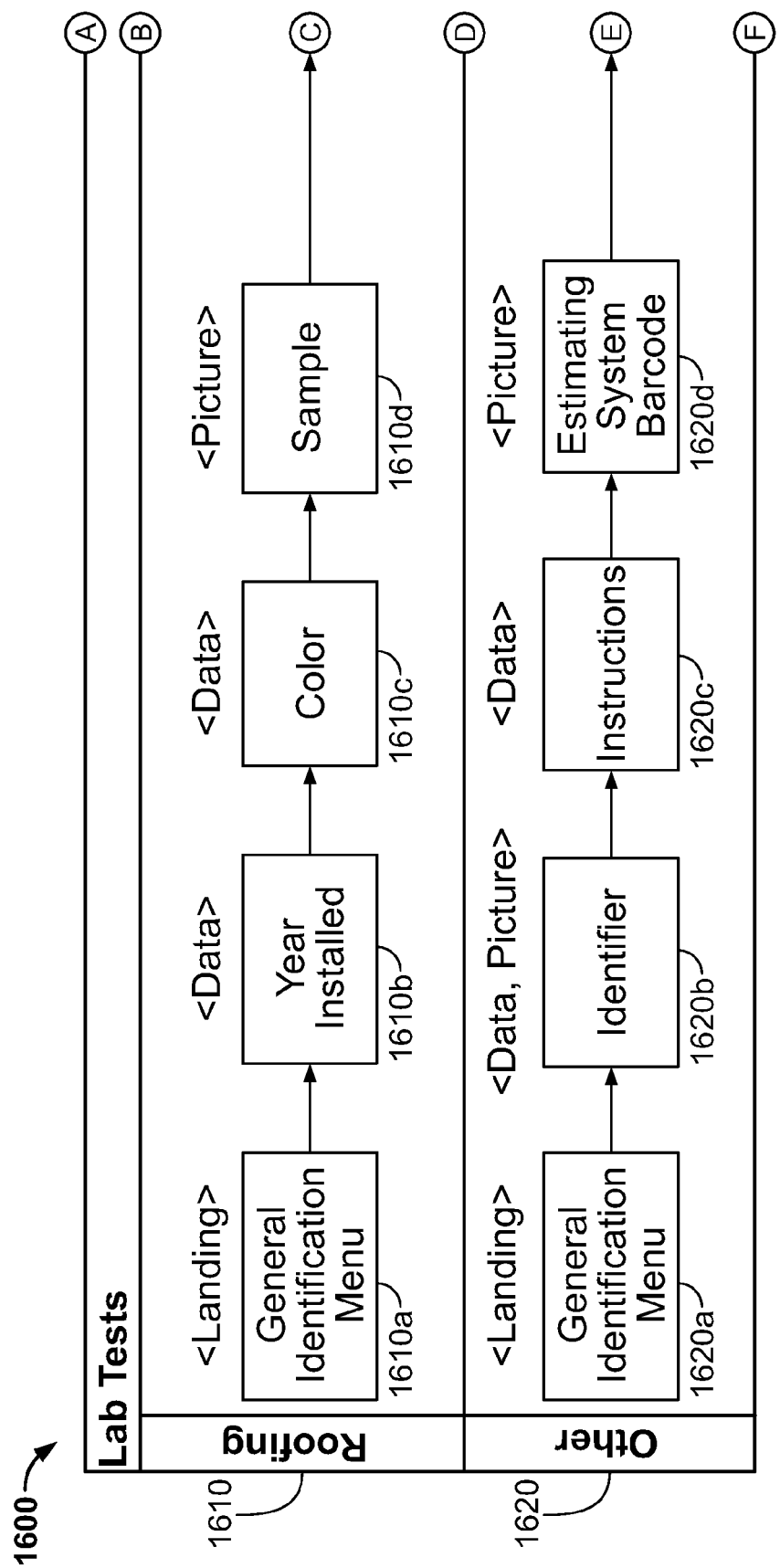
FIG. 16 shows an exemplary logic flow diagram for submitting a roofing sample or other sample for lab testing and analysis of roofing products in accordance with methods of the present disclosure.
Figure 16:
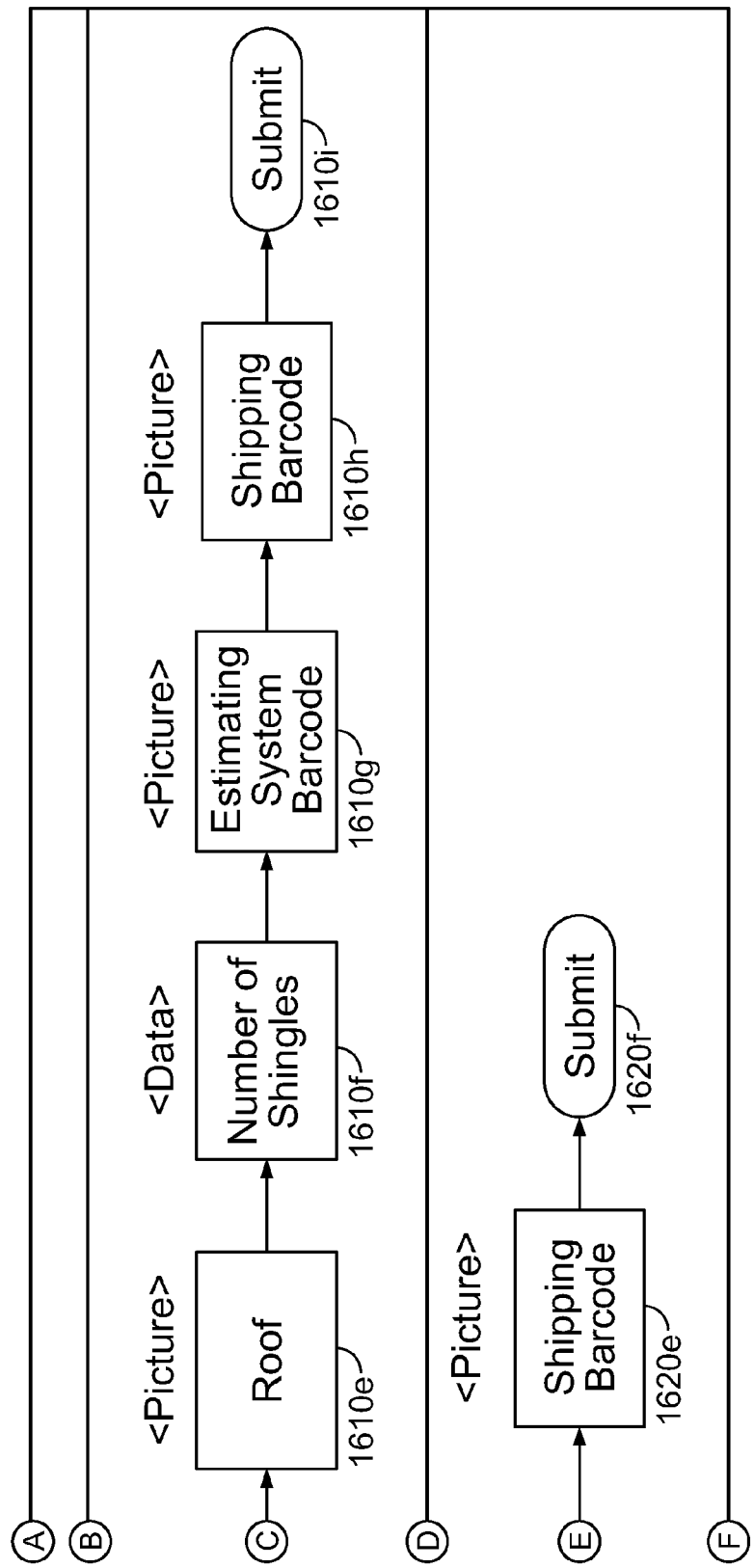

FIG. 16 illustrates the displays and options for a user using a new lab test submittal workflow for roofing materials and FIG. 16 also provides a generic workflow for submitting a physical sample of a building material sample in accordance with the present disclosure [1600]. In some embodiments, workflow [1600] is performed using apparatus as described herein. In some embodiments, use of apparatus to perform workflow [1600] is according to the present methods and/or as described herein. As indicated above, in some embodiments, the workflow paradigm of an app of the present disclosure is designed such that it leads a user through an efficient, wizard-style interface. In some embodiments, to proceed through the process workflow, a user provides user input entry. In some aspects, user input can include information input, data input, photographic input, or any combination of those. In some embodiments, where a user takes, inputs, enters, and/or uploads a photograph, a user may include multiple photographs, for example showing different angles of the identified feature. In some embodiments, an app may request a user enter a response to a question to define or clarify a specific situation and depending upon the response, present additional options for input. In some aspects, as a user enters information or selects from available choices, such antecedent screen choices affect display screens and choices in subsequent screens. This interface/layout creates a cohesive and consistent input experience for a user. As described above, work flows as adaptable, and, thus, these are exemplary. Moreover, the building materials products shown are exemplary and not intended to be limiting.

Referring to the Roofing level of the diagram [1610], in some embodiments, a user opens an app to initiate a new lab test [1610a] and inputs general information regarding a claim and general identification information. In some embodiments, a user will next enter data indicating a year roofing was installed [1610b]. In some embodiments, a user will next enter data indicating a color of roofing [1610c]. In some embodiments, a user then enters a photograph showing roofing [1610d]. In some embodiments, a user then enters a photograph showing a roof [1610e]. In some embodiments, a user will next enter data indicating a number of shingles [1610f]. In some embodiments, a user then enters a photograph estimating system barcode [1610g]. In some embodiments, a user next takes a photograph showing a shipping barcode [1610h]. In some embodiments, a user then submits [1610i] information, data, and photos to a service provider computing device.

Referring to the Other level of the diagram [1620], in some embodiments, a user opens an app to initiate a new lab test [1620a] and inputs general information regarding a claim and general identification information. In some embodiments, a user will next enter data indicating an identity of a building material sample for a new lab test and take a photograph of a building material sample for a new lab test [1620b]. In some embodiments, a user will next enter data indicating instructions [1620c]. In some embodiments, a user then enters a photograph estimating system barcode [1620d]. In some embodiments, a user next takes a photograph showing a shipping barcode [1620e]. In some embodiments, a user then submits [1620f] information, data, and photos to a service provider computing device.

According to some embodiments, workflows, screen content, data, and validation utilize a meta-data framework that effectively separates the content from the application program itself. The workflow and screen content can change with a change within the architecture. As such, this architecture improves turnaround times and to timely meet changing customer requirements. Changes are updated with the required data inputs, formats and validations without encountering an app ecosystem approval process (e.g., Apple Store, Android Store, etc.). The framework architecture also allows for customized workflows.

In some embodiments, upon completion of taking measurements and photos, a user may "submit" data to a service provider for analysis. According to some embodiments, the app will verify that all required data and photos have been acquired and that all data and photos are available for transmission. If there is missing data or photos, the app presents a display showing a request for the missing data in a linear format that is similar to the original paradigm but only presenting for display to user the missing information pages. Upon completion, the user may again try to submit to the service provider.

Following a successful submission of the user input to the service provider, in some embodiments, the information, data, and photos are displayed to a trained analyst for analysis. The analyst uses a suite of photographic and data analysis tools to assist in evaluating the user input for the unknown sample. In the case of an unknown carpet sample, for example, these inputs are processed through algorithms that transform the information into standard carpet specifications. The acquired product specifications are then further processed through a library of know carpet products to determine a value match or a like, kind, and quality match. The analyst then directs preparation of a report customized for the user. In some embodiments, the service provider's delivers this report directly back to the user through the app. In some implementations, the process from submission to completion takes less than a day. In some embodiments, the process from submission to completion takes, for example less than 30 minutes, less than 1 hour, less than 2 hours, less than 3 hours, less than 4 hours, less than 6 hours, less than 12 hours, less than 24 hours and/or less than 48 hours.

Offsite Analyst Assessment

According to some embodiments, for example, when the unknown sample is carpet, an analyst at the service provider may use the acquired and transmitted data to determine the construction method, the stitch, the gauge, and/or the pile height of the carpet and the fiber of the carpet. This information is then used in another computer system to find the closest like, kind, and quality carpets on the market matching these determined properties. Other non-limiting characteristics of carpet that an analyst may encounter include, for example: color, mill, style, fiber, width, construction, fiber ply, face weight, backing material, tufts/sq. inch, and/or pad type.

According to some embodiments, for example, when the unknown sample is wood, the analyst from the service provider may use the acquired, transmitted data to determine the width, thickness, veneer thickness, locking mechanism, and/or species. This information is then used in another computer system to find the closest like, kind, and quality wood products on the market matching these determined properties. Other non-limiting characteristics of wood that an analyst may encounter can include, for example: manufacturer, style, board thickness, length, width, species, veneer thickness, veneer cut, surface finish, ply composition, stained finish, cut, locking type, piles, visual, color, and whether there is an attached pad.

According to some embodiments, for example, when the material choice is laminate, the analyst may use the acquired, transmitted data to determine the width, thickness, veneer thickness, and/or locking mechanism. This information is then used in another computer system to find the closest like, kind, and quality laminate products on the market matching these determined properties. Other non-limiting characteristics of laminate that an analyst may encounter include, for example: manufacturer, style, surface texture, locking type, color, class, width, length, thickness, core thickness, core density, abrasion resistance, and whether there is an attached pad.

According to some embodiments, for example, when the material choice is vinyl, the analyst may use the acquired, transmitted data to determine the thickness, veneer thickness, wear layer, and/or number of layers. This information is then used in another computer system to find the closest like, kind, and quality vinyl products on the market matching these determined properties. Other non-limiting characteristics of vinyl that an analyst may encounter include, for example: color, manufacturer style, width, product form, tile/plank size, construction, backing, wearlayer type, wearlayer thickness, and overall thickness.

According to some embodiments, for example, when the material choice is siding, the analyst may use the acquired, transmitted data to determine the thickness, profile, projection, color, and/or grain pattern. This information is then used in another computer system to identify the manufacturer and product name of the siding.

According to some embodiments, for example, when the material choice is roofing, the analyst may use the acquired, transmitted data to determine the thickness, construction, size, and/or color. This information is then used in another computer system to identify the manufacturer and product name of the roofing.

According to some embodiments, for example, when the material choice is tile, the analyst may use the acquired, transmitted data to determine the characteristics of the tile. Other non-limiting characteristics of tile that an analyst may encounter include, for example: color, manufacture, style, product form, thickness, face dimension, wet coefficient, wear rating, moisture absorption, surface treatment, surface value, edge design, and/or MOH's hardness.

Measurement Stand

According to some embodiments, a remote, mobile computing device may be for example, a hand held computer, cell phone, smart phone, smart device, or tablet etc. In some embodiments, a remote, mobile computing device has an installed operating system. In some embodiments, an operating system may be an Apple or Android or some other system. In some embodiments, an app display takes advantage of a small form factor of a remote, mobile communication device.

Figure 17:
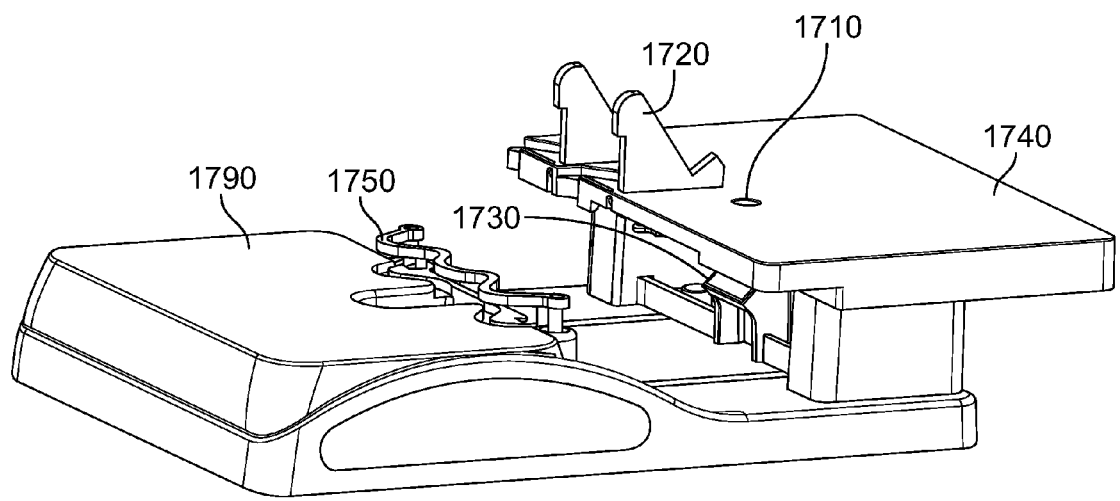
FIG. 17 shows an exemplary measurement stand for placement and alignment of a remote, mobile communications device and the building material sample.
Figure 17:
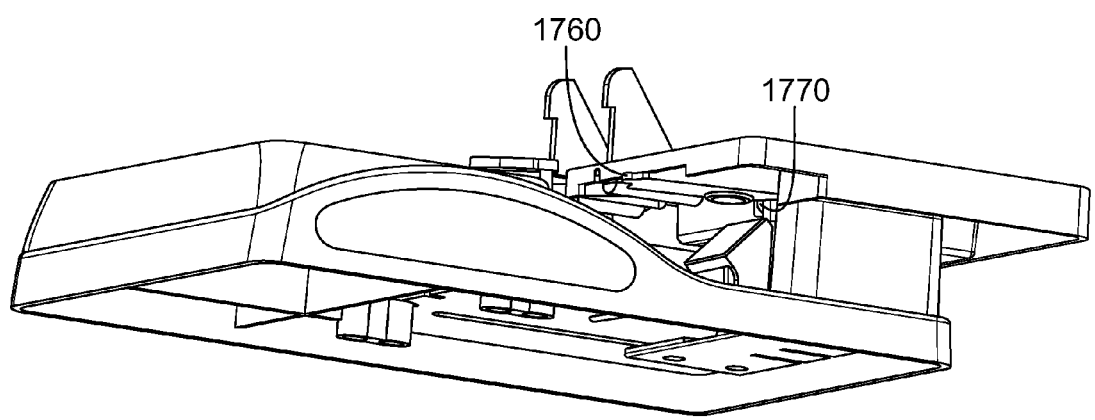
Figure 18:
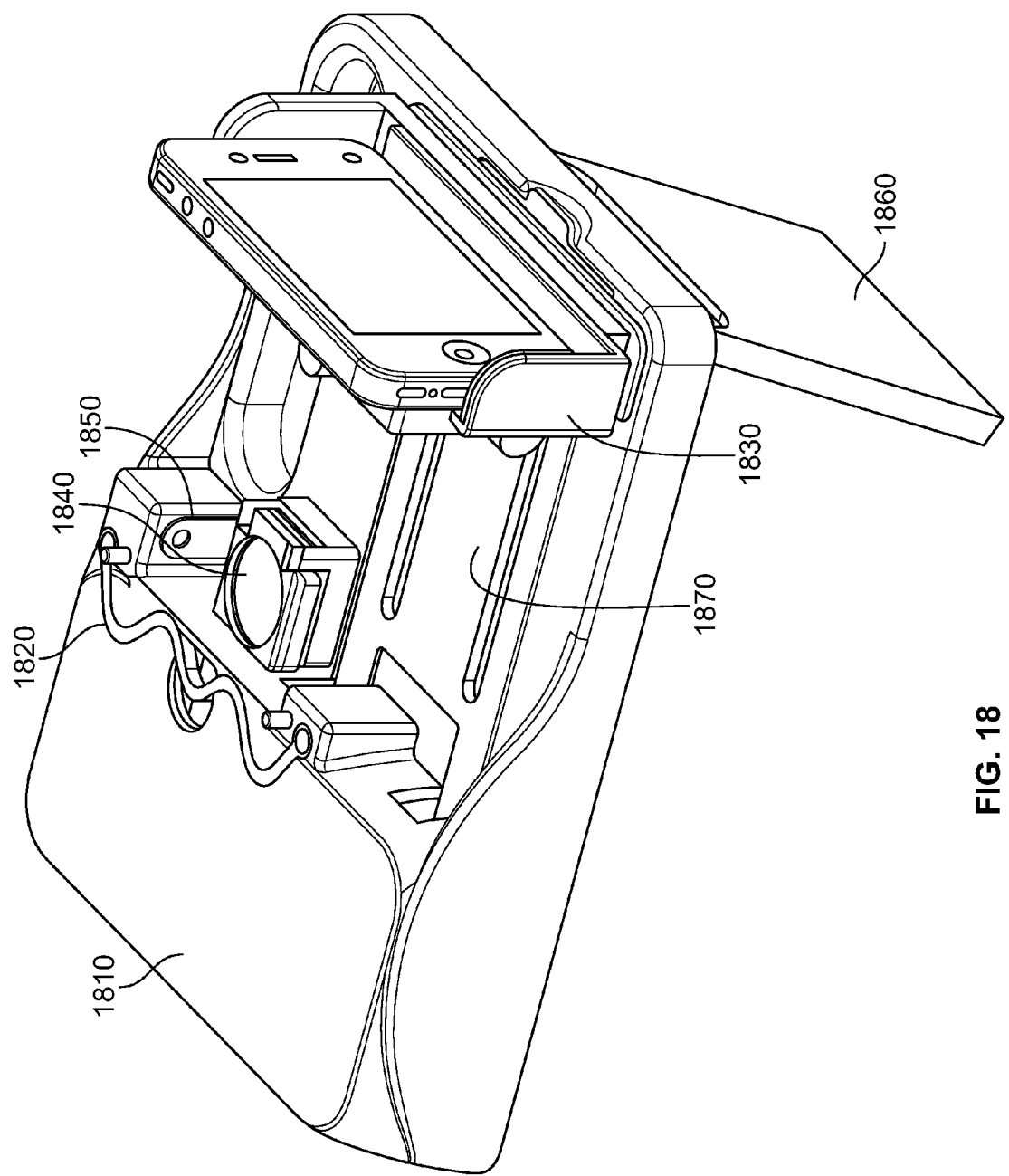
FIG. 18 shows an alternative exemplary measurement stand for placement and alignment of a remote, mobile communications device and the building material sample.
Figure 19:
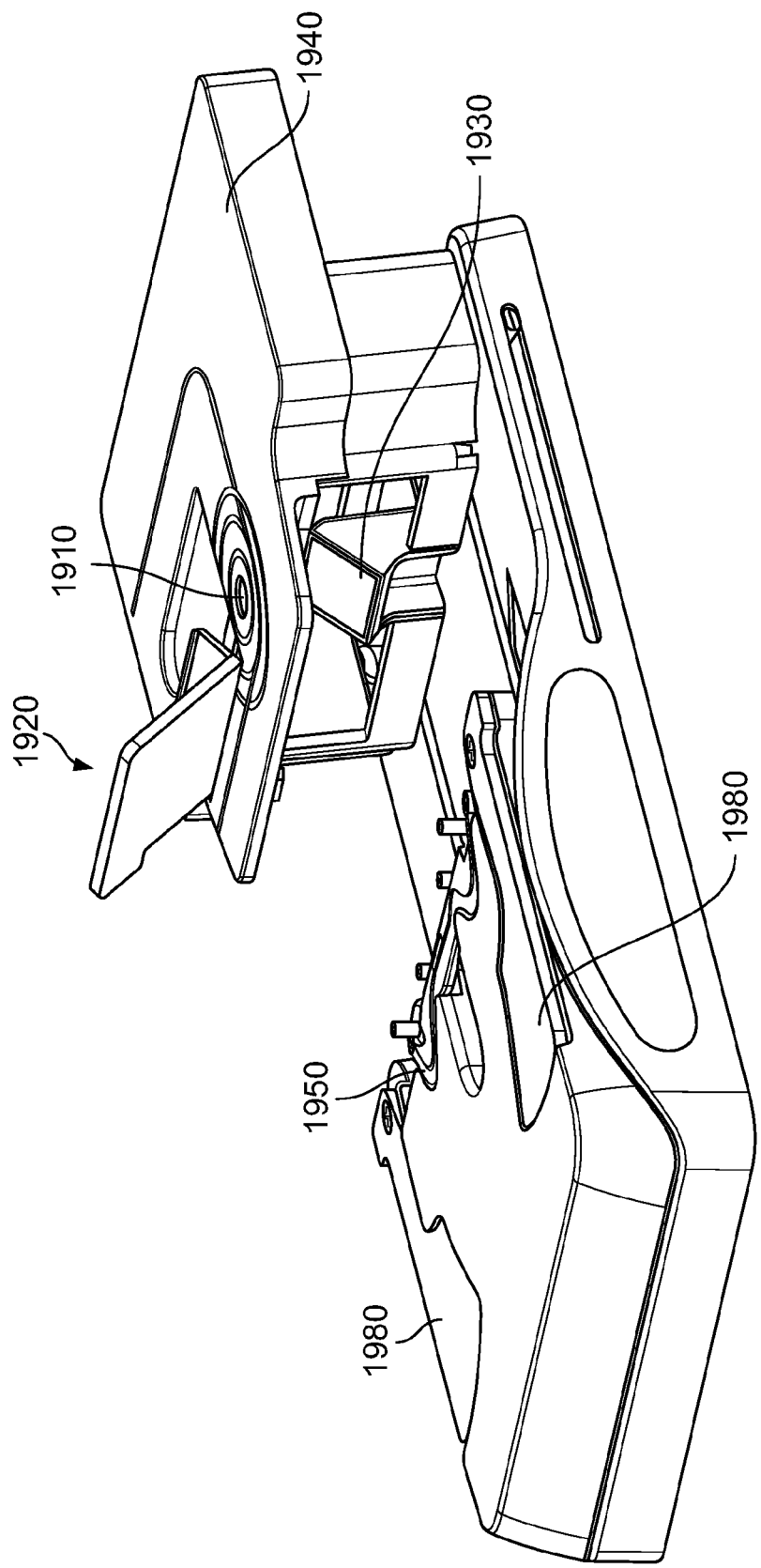
FIG. 19 shows an alternative exemplary measurement stand for placement and alignment of a remote, mobile communications device and the building material sample.
Figure 19:
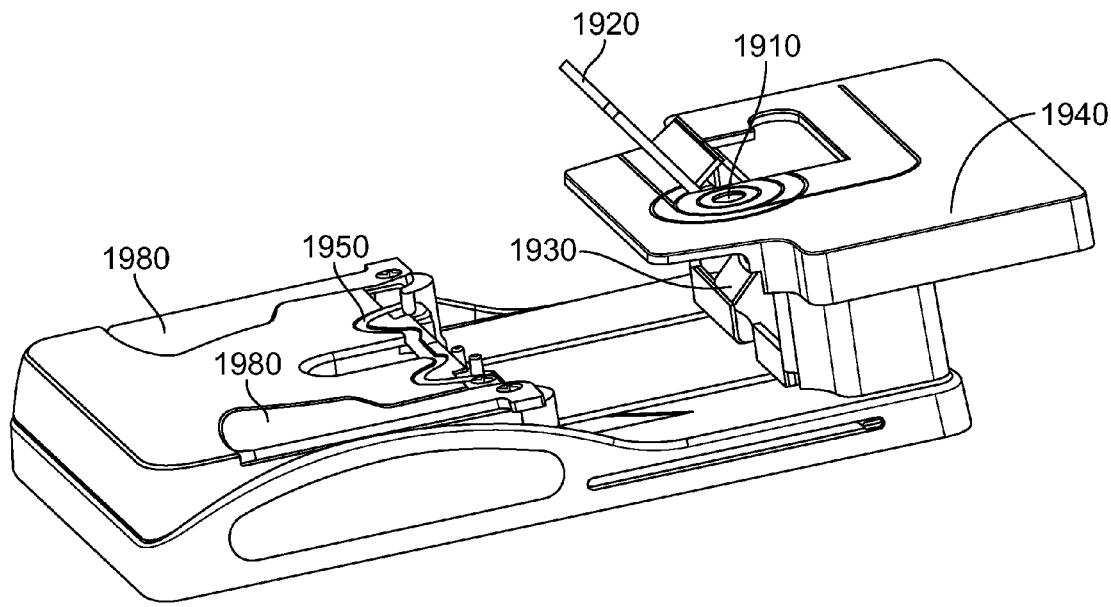
Figure 19:
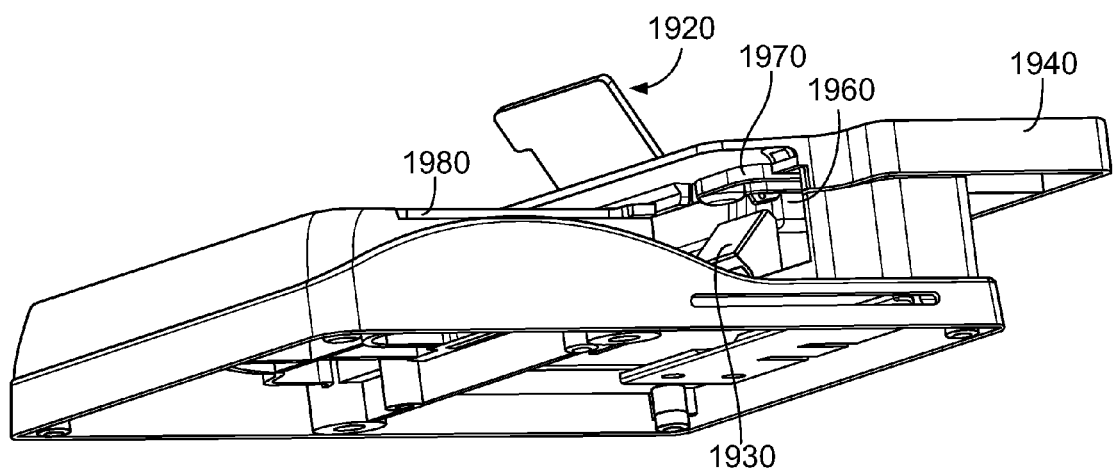

Referring now to FIG. 17-19, according to some embodiments of the present disclosure, a user at an on-site location with a remote, mobile computing device can acquire, collect and/or enter information, data, and/or photos using a measurement stand illustrated. The purpose of a measurement stand is to provide a stable environment to take precision photographs and measurements. A measurement stand provides various features to support collecting data from, for example, carpet, wood, laminate, tile, and/or vinyl flooring. In some embodiments, dimensions of a measurement stand are 10 L×7 W×2.5 H when a measurement stand is fully closed and 11.5 L×7 W×2.5 H when open.

In some embodiments, when a measurement stand is fully open a length is about 5 inches, about 5.5 inches, about 6 inches, about 6.5 inches, about 7 inches, about 7.5 inches, about 8 inches, about 8.5 inches, about 9 inches, about 9.5 inches, about 10 inches, about 10.5 inches, about 11 inches, about 11.5 inches, about 12 inches, about 12.5 inches, about 13 inches, about 13.5 inches, about 14 inches, about 14.5 inches, about 15 inches, about 15.5 inches, about 16 inches, about 16.5 inches, about 17 inches, about 17.5 inches, about 18 inches, about 18.5 inches, about 19 inches, about 19.5 inches, about 20 inches, about 20.5 inches, about 21 inches, about 21.5 inches, about 22 inches, about 22.5 inches, about 23 inches, about 23.5 inches, about 24 inches, about 24.5 inches, about 25 inches, about 25.5 inches, about 26 inches, or more. In some embodiments, when a measurement stand is fully open a width is about 3 inches, about 3.5 inches, about 4 inches, about 4.5 inches, about 5 inches, about 5.5 inches, about 6 inches, about 6.5 inches, about 7 inches, about 7.5 inches, about 8 inches, about 8.5 inches, about 9 inches, about 9.5 inches, about 10 inches, about 10.5 inches, about 11 inches, about 11.5 inches, about 12 inches, about 12.5 inches, about 13 inches, about 13.5 inches, about 14 inches, about 14.5 inches, about 15 inches, about 15.5 inches, about 16 inches, about 16.5 inches, about 17 inches, about 17.5 inches, about 18 inches, about 18.5 inches, about 19 inches, about 19.5 inches, about 20 inches, about 20.5 inches, about 21 inches, or more. In some embodiments, when a measurement stand is fully open a height is about 0.5 inch, about 1 inch, about 1.5 inches, about 2 inches, about 2.5 inches, about 3 inches, about 3.5 inches, about 4 inches, about 4.5 inches, about 5 inches, about 5.5 inches, about 6 inches, about 6.5 inches, about 7 inches, about 7.5 inches, about 8 inches, about 8.5 inches, about 9 inches, about 9.5 inches, about 10 inches, about 10.5 inches, or more.

FIG. 17 shows an exemplary measurement stand for placement and alignment of a remote, mobile communications device and a building material sample. Individual features are described in detail below.

FIG. 17A shows a top view of the exemplary measurement stand for placement and alignment of the remote, mobile communications device and a building material sample. In some aspects, a camera hole [1710] provides gross alignment of a camera of a remote, mobile computing device to take photographs of a building material sample. In some embodiments, an angle stand [1720] and mirror [1730] allow placement of a remote, mobile computing device in a user friendly position and for manipulating a building material sample and a display screen of a remote mobile computing device relative to one another. Ultimately, an angle stand [1720], camera hole [1710], and mirror [1730] facilitate acquiring photographs of a building material sample and acquiring accurate measurements. According to some aspects, a horizontal platform [1740] supports a remote, mobile computing device in a firm position to eliminate hand shake and blurry pictures. In some embodiments, a clamp [1750] secures a building material sample during acquisition of measurements and photos.

FIG. 17B shows a bottom/side view of an exemplary measurement stand for placement and alignment of a remote, mobile communications device and a building material sample. In some embodiments, a device allows movement in a plurality of positions, for example, for taking magnified photographs. A close position puts a camera lens of a remote mobile computing device behind a pivoting magnifying assembly [1760]. A close position allows a user to shoot photos through a pivoting magnifying assembly [1760] at a set distance. In some embodiments, a pivoting magnifying assembly [1760] provides a magnified view of a sample edge. In some embodiments, a magnifying assembly [1760] can be removed from a measurement stand and placed on top of a piece of tile. A user can then take a photo of a magnified tile surface for analysis. A lamp [1770] is provided for illuminating a building material sample.

In some embodiments, a measurement stand includes a building material sample platform [1790]. In some implementations a building material platform is horizontal with stop pins to ensure proper sample placement. Stop pins position a sample a known distance from a camera lens of a remote mobile computing device. In some embodiments, a measurement stand also includes a clamp [1750]. In some embodiments, a clamp [1750] is made of metal, e.g. aluminum. In some embodiments, a clamp [1750] is made of plastic, e.g. vinyl. In some embodiments, a clamp [1750] is configured to hold a small piece of vinyl in a proper position for photographing. A clamp [1750] is designed to spread pressure across a surface of a building material sample so that any distortion added from pressure away from a sample edge is avoided.

FIG. 18 shows an alternative exemplary measurement stand for placement and alignment of a remote, mobile communications device and a building material sample. A building material sample may be placed on a sample platform [1810] and stabilized with a clamp [1820]. A remote mobile computing device (e.g., cell phone with camera) is placed in a cradle [1830], which holds a remote mobile computing device stationary, thereby minimizing blurry pictures. A cradle [1830] can be adjusted, e.g., by movement along a track, to position a remote mobile computing device for taking photographs. A cradle also can automatically position a camera lens of a remote mobile computing device behind a raised magnifier ensemble [1840], which allows a user to take photographs through a magnifying glass with a camera of a remote mobile computing device at a set distance from a building material sample. A lamp [1850] is provided to illuminate an edge of a building material sample. A flip stand [1860] allows placement of a remote mobile computing device at an angle for easy viewing access of a display screen of a remote mobile computing device during operation of an app. A display screen of a remote mobile computing device provides on screen guidance for collection of data and to facilitate obtaining photographs of a building material sample. In some embodiments, an elevation stand [1870] allows raising of a camera of a remote mobile computing device above a horizontal to an optimal angle (e.g., from 15 to 45 degrees above the horizontal, e.g., from 30 to 35 degrees above a horizontal) to allow a standard, close-up view of a top of a building material sample. In some embodiment, there is no flip stand, and a housing itself is angled. In some embodiments, there is a mirror to facilitate obtaining photographs of a material.

FIG. 19 shows an exemplary measurement stand for placement and alignment of a remote, mobile communications device and a building material sample. Individual features are described in detail below.

Referring to FIG. 19A and FIG. 19B, in some embodiments, a camera hole [1910] provides gross alignment of a camera for a remote, mobile computing device to facilitate photographing building materials. In some embodiments, an angle stand [1920] and a mirror [1930] allow placement of a remote, mobile computing device in a user friendly position and for manipulating a building material sample and a display screen of a remote mobile computing device relative to one another. An angle stand [1920], a camera hole [1910], and mirror [1930] facilitate photographing and acquiring accurate measurements of a building material sample. According to some aspects, a horizontal platform [1940] supports a remote, mobile computing device in a firm position to eliminate hand shake and blurry pictures. In some embodiments, a clamp [1950] secures a sample during acquisition of measurements and photos. In some embodiments, an oversized building material sample may be supported by at least one adjustable extension flap [1980] laterally disposed on a sample platform. In some embodiments, an adjustable extension flap includes a pair arms designed to hold hard surface samples of various widths, lengths, and/or thickness. In some embodiments, an adjustable extension flap [1980] holds a weight of a measurement stand with a remote mobile computing device. In some embodiments, an adjustable extension flap [1980] is configured to support an oversized material sample, for example, uncut and/or long boards, without an additional supporting surface.

FIG. 19C shows a bottom/side view of an exemplary measurement stand for placement and alignment of a remote, mobile communications device and a building material sample. In some embodiments as above described, a device is allowed to move to a plurality of positions, for example, for taking magnified photographs. In some embodiments, a close position puts a camera lens behind a pivoting magnifying assembly [1960]. In some embodiments, a close position allows a user to shoot photos through a magnifying pivoting magnifying assembly [1960] at a set distance. In some embodiments, a pivoting magnifying assembly [1960] provides a magnified view of an edge of a building material sample. In some embodiments, a magnifying assembly [1960] can be removed from an exemplary measurement stand and placed on top of a piece of tile, for example. In some embodiments, a user can then take a photo of a magnified tile surface for analysis (not shown). In some embodiments, a lamp [1970] illuminates a building material sample, for example, an edge of a building material sample.

Portable Spectrometer

According to some embodiments, the present disclosure includes a photo spectrometer for material qualitative analysis. In industry there are many instances when it is necessary to distinguish one material from another. Often this discrimination is done with a broadband infrared spectrometer, such as the type that employs a diffraction grating and precise angular displacement to determine the wavelength being measured. By collecting data over some continuous range of optical absorption, the resulting spectrum can help identify a material under test.

Though it has proven quite effective in material identification, near infrared spectrum analysis, as it has been practiced to date, has been generally confined to the laboratory environment due to the size and complexity of the measuring apparatus. In various embodiments, the invention is intended to replace the bulky and expensive laboratory apparatus often used with an inexpensive, mobile and/or hand held device that that may be used in the field without concern for sensitive optical alignment and a vibration free bench. The mobile device can obtain intensity measurements at discrete wavelengths and identify material type from this limited amount of data, rather than obtaining and analyzing an entire spectrum as with laboratory systems.

In some embodiments, infrared spectroscopy is used to determine which carpet fiber or other material is being used in a particular floor covering. For purposes of explanation, and not intending to be limiting, the spectrometer may be used to discriminate between types of carpet fibers. For example, four fibers used in carpeting material include: nylon, acrylic, olefin, and polyester, though it is clear that other embodiments can apply the same principals to discriminate many different types of fibers and materials.

Figure 20:
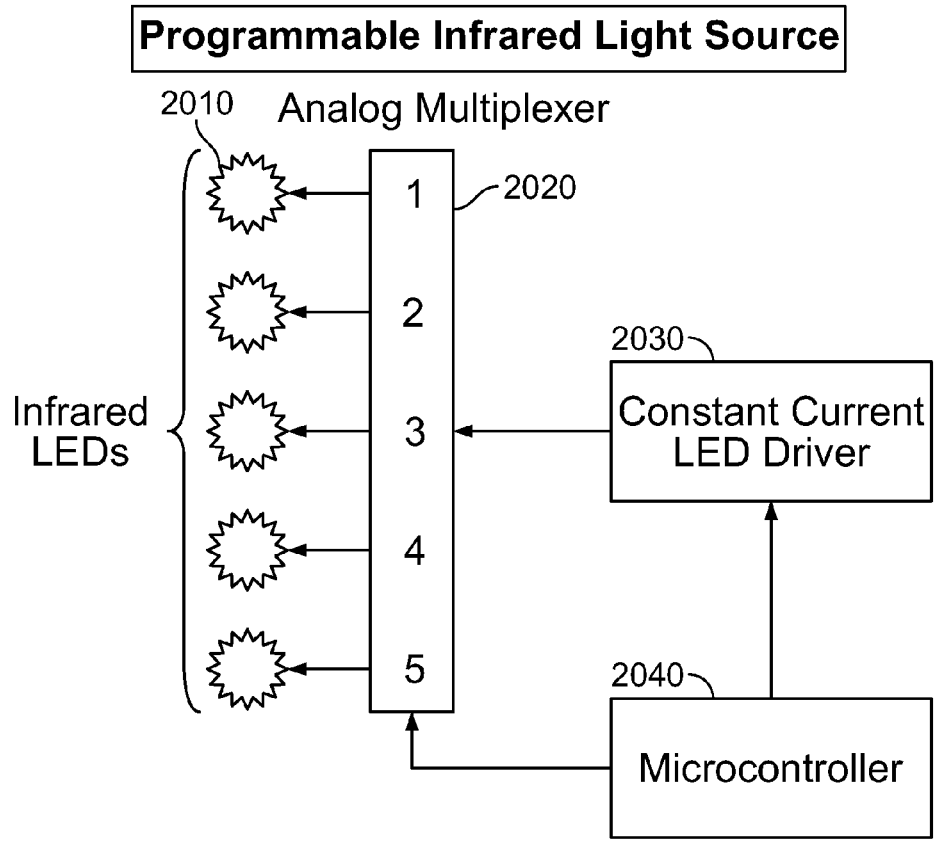
FIG. 20 shows light source components of a spectrophotometer device of the present disclosure.

In some embodiments, of the present disclosure, as illustrated in FIG. 20 the spectrometer apparatus has a light source device comprised of a plurality of infrared LEDs [2010], an analog multiplexer [2020] that is used to control which LED is illuminated at any given time, a constant current LED driver [2030], and a microcontroller [2040]. The microcontroller [2040] may control the current being applied to an LED and by use of the multiplexer [2020], control which LED is on. This apparatus will only illuminate one LED at a time in order to collect reflectance data for one wavelength in the recognition spectrum.

Figure 21:
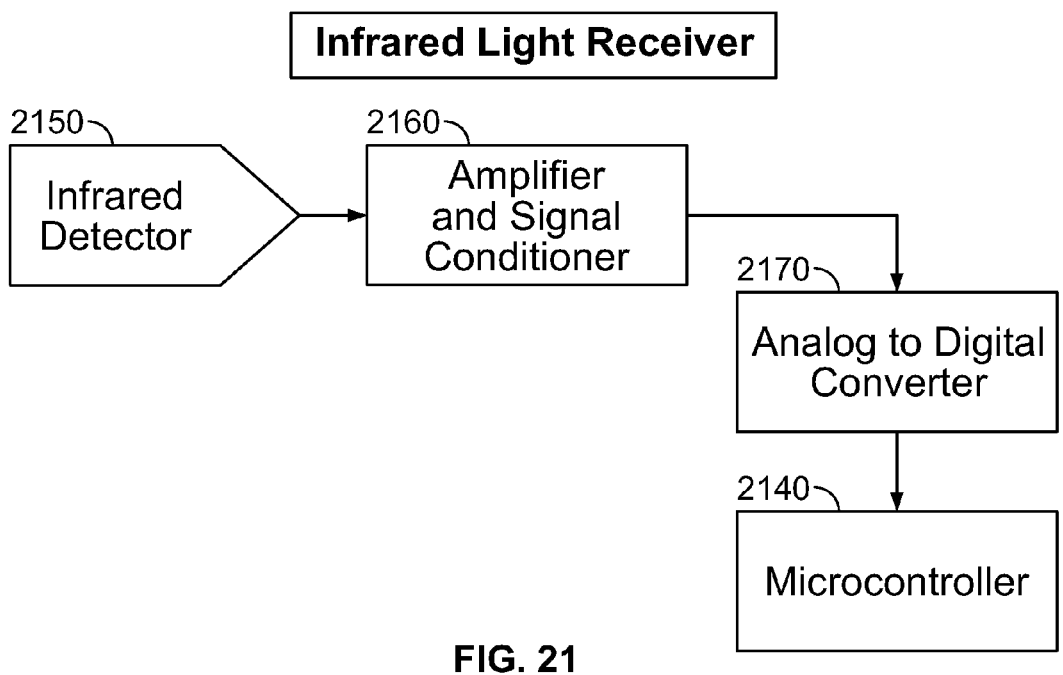
FIG. 21 shows light detection components of a spectrophotometer device of the present disclosure.

FIG. 21 shows the light detection components of the spectrophotometer device of the present disclosure. In some embodiments, a broad spectrum photodiode [2150] is used to receive the reflected infrared light from a test sample. In some embodiments, a signal amplifier and conditioner [2160] is used to convert the signal from the photodiode [2150] to the proper voltage range for input to the analog to digital converter [2170]. The signal from the analog to digital converter [2170] is fed to the microcontroller [2140] for analysis. The illustration of FIG. 21 shows them as separate; however, the signal amplifier and conditioner [2160] and the analog to digital converter [2170] may be internal to the microcontroller [2140] device. In this device the photo-responsivity of the photodiode [2150] will be good but not necessarily flat across the various wavelengths of interest.

Figure 22:
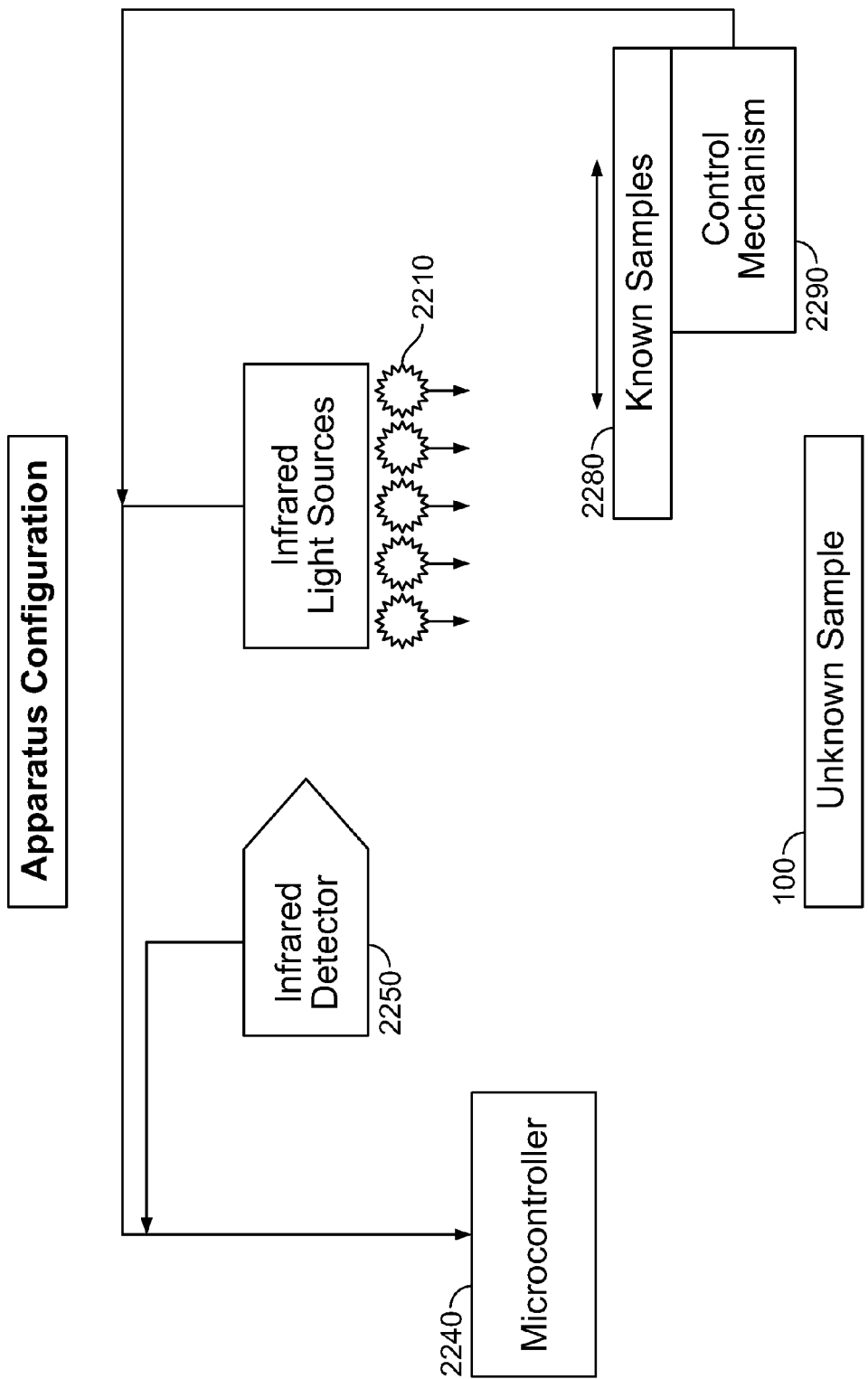
FIG. 22 shows an exemplary configuration of a complete spectrophotometer device of the present disclosure.

In accordance with some embodiments, FIG. 22 shows an exemplary configuration of the complete spectrophotometer device of the present disclosure. In some implementations, this device allows the system to interpose a known sample so that its spectral data may be compared to the unknown sample. Each of the known samples may be individually scanned in this fashion so that each may be compared to the data from the unknown sample under test [100] when there are none of the known samples [2280] in the optical path. The control mechanism [2290] is used to place the known samples in the proper position for testing and comparison and it reports what is in the optical path to the microcontroller [2240]. In some embodiments, the control mechanism [2290] may be automated and under the microcontroller [2240] control. In some embodiments, the control mechanism [2290] may be operated by the user who would activate the imposition of the known sample for comparison.

Spectrometer Operation

In some embodiments, fiber samples are included in the design so that new comparison data is collected whenever an unknown fiber is scanned. In some embodiments, this is been done to compensate for thermal and other short and long term variations in the operating environment that could affect performance. With further testing it may well become evident to a user that when the unknown data is properly normalized and then analyzed, these effects will be found to be insignificant to the objective of simply identifying an unknown sample as one of a small set of expected materials. In some embodiments, the spectrometer does not include known samples or control mechanism, for example, there would only be a table with the data sets that represent the set of expected known materials.

Figure 23:
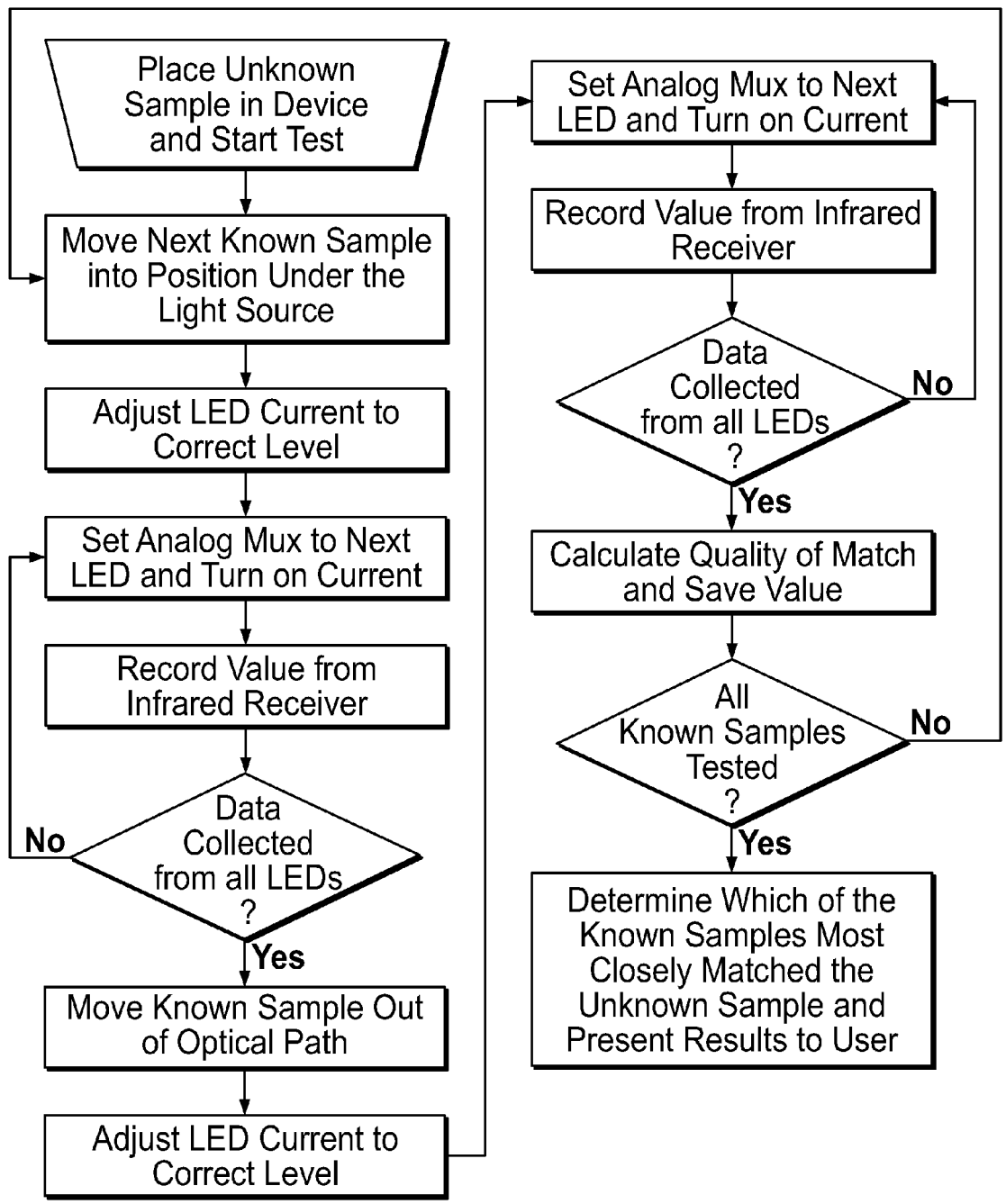
FIG. 23 shows an exemplary flow chart showing a process of collecting data using a spectrophotometer device of the present disclosure.

Referring now to FIG. 23, an exemplary flow chart shows the process of collecting data using the spectrophotometer device of the present disclosure. In some embodiments, for each possible matching fiber the known sample and the unknown sample are scanned and then the quality of the match is determined. After this process has been done for all of the members of the set of expected fibers, then the best match can be determined. In the case where no physical samples of the set of known fibers are included in the device, the first step of scanning the internal known sample is skipped.

Figure 24:
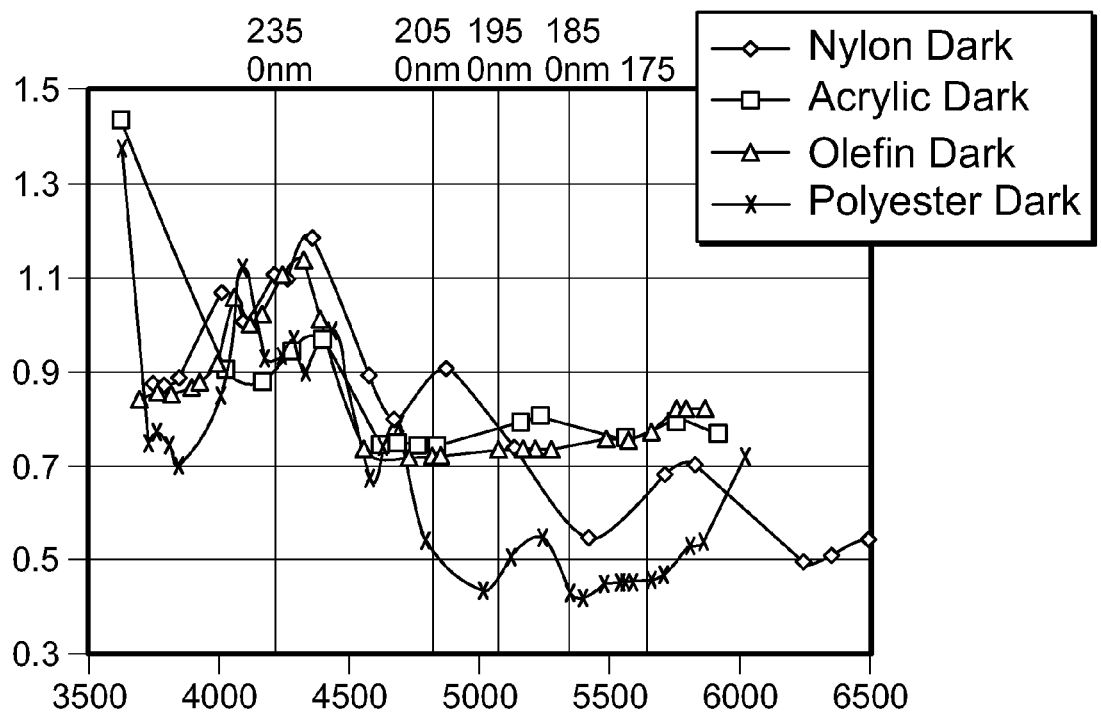
FIG. 24 shows a plot of infrared spectra of four synthetic fibers of nylon, acrylic, olefin, and polyester.
Figure 25:
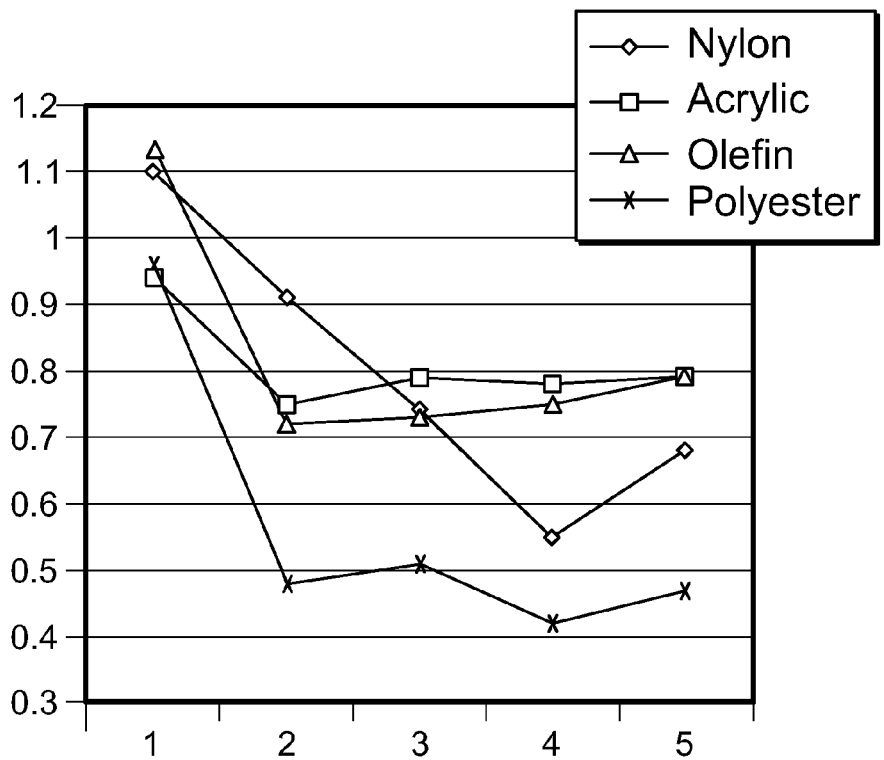
FIG. 25 shows a plot analyzing infrared spectra data points based on five intersections of each spectrum with vertical lines creating a unique recognition pattern for each of the four fibers of interest, including nylon, acrylic, olefin, and polyester.

FIG. 24 shows a plot of infrared spectra of four synthetic fibers of nylon, acrylic, olefin, and polyester. These fibers are only examples of how this invention can simplify material qualitative analysis. Also on this chart are five vertical lines corresponding to different wavelengths within these spectra. Monochromatic LEDs are available at these wavelengths. On the chart, the horizontal axis is labeled with the CGS wave number, and the vertical axis is the normalized reflected light amplitude. FIG. 24 illustrates a continuous infrared spectrum of each fiber shown on the graph. Each fiber has a unique pattern within this part of the optical spectrum. But, at the intersections of the vertical lines with each of those spectra, the data points represent a unique identifier for each fiber. All five intersections of each spectrum with the vertical lines are collected to create a unique recognition pattern, or function, for each of the four fibers of interest. This is listed in Table 1 and illustrated in FIG. 25. There are many mathematical means by which these four functions can be compared to a set of five data points, or a function, representing an unknown fiber, in order to calculate which of the four known fibers is the best match, and thereby identifying an unknown fiber that is within the set of fibers of interest.

TABLE 1

|  | 2350 nm | 2050 nm | 1950 nm | 1850 nm | 1750 nm |
| --- | --- | --- | --- | --- | --- |
| Nylon | 1.10 | 0.91 | 0.74 | 0.55 | 0.68 |
| Acrylic | 0.94 | 0.75 | 0.79 | 0.78 | 0.79 |
| Olefin | 1.13 | 0.72 | 0.73 | 0.75 | 0.79 |
| Polyester | 0.96 | 0.48 | 0.51 | 0.42 | 0.47 |

Figure 26:
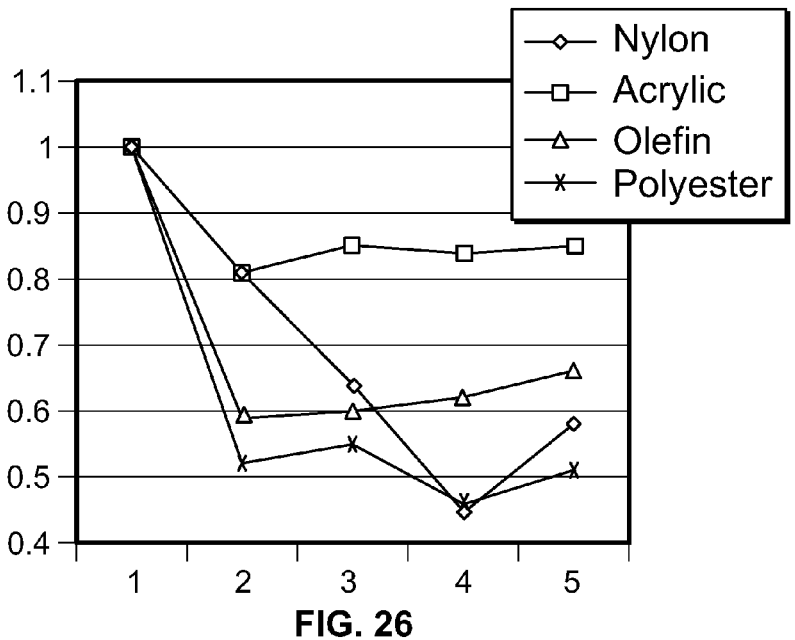
FIG. 26 shows a plot analyzing infrared spectra data points normalized for calculating an offset for data for comparison for each of the four fibers of interest, including nylon, acrylic, olefin, and polyester.

FIG. 26 shows a plot analyzing the infrared spectra data points normalized for calculating the offset for the data for comparison.

Since this invention is intended to be used in the field, the determination of a matching set of data points must be done with minimal machine cycles. In some embodiments, the following method might be employed. In each recognition pattern of five points there are only variations in amplitude. The wavelength at which the data are gathered is always the same five wavelengths of the LEDs being employed. It is expected that successive readings of the same type of fiber will not always exactly produce the same spectral pattern. Variations due to age, sun light exposure, dyes, and other contamination of the sample are expected. There needs to be a scoring method that identifies the likelihood that any unknown sample is a match for one of the known sets of spectral patterns.

In certain embodiments, data corresponding to the discrete wavelengths for distinguishing materials is obtained for an unknown sample using the mobile spectrometer, and the detected intensities at those wavelengths are compared to expected values for known materials. For example, the degree of match between the unknown sample data and known samples may be computed for each known material type the unknown sample is suspected to be (e.g., nylon, acrylic, olefin, and polyester). The data may be normalized by calculating an offset from the first LED (2350 nm) to the first data point of the known spectrum for comparison. As shown in FIG. 26, this offset would be applied to all the data points in the unknown measurement. In this comparison method no adjustment is made for gain. Next, an absolute value of a difference between each of the remaining data points in known and unknown samples is calculated and summed. This sum would be used to decide which of the four known spectra is the best match for the unknown sample, based on the lowest value. In some embodiments, the root mean square of the deviations may be used from one sample to the next, or any of many known methods to test correlation or quality of fit.

Other methods of analysis of the data obtained at the discrete wavelengths for identification of the unknown material could be performed as well. In certain embodiments, data analysis is performed by a processor on-site. In other embodiments, data analysis is performed offsite, e.g., at a lab. In certain embodiments, a user is guided in the operation of the mobile infrared spectrometer by an app on their mobile computing device (e.g., the app described in more detail herein). The data from the spectrometer may be analyzed by a processor which is part of the spectrometer device, itself, or the data may be analyzed offsite at a laboratory. The spectrometer may transmit data wirelessly for offsite analysis, or the spectrometer may transmit data to the user mobile computing device for transmission of data to an offsite laboratory for real-time (or near real-time) analysis.

Network Environment

Figure 27:
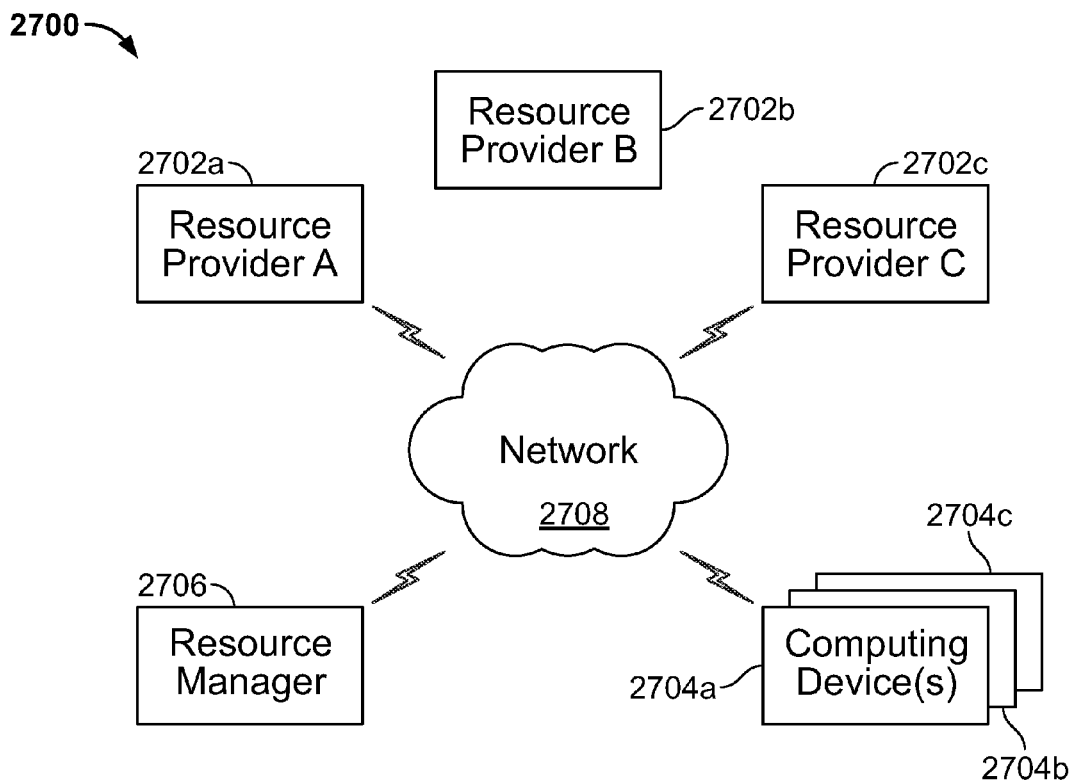
FIG. 27 is a block diagram of an example network environment for implementing data collection platform.

FIG. 27 is a block diagram of an example network environment for implementing data collection platform. As shown in FIG. 27, an implementation of a network environment [2700] for use in data collection is shown and described. In brief overview, referring now to FIG. 27, a block diagram of an exemplary cloud computing environment [2700] is shown and described. The cloud computing environment [2700] may include one or more resource providers [2702a], [2702b], [2702c] (collectively, [2702]). Each resource provider [2702] may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider [2702] may be connected to any other resource provider [2702] in the cloud computing environment [2700]. In some implementations, the resource providers [2702] may be connected over a computer network [2708]. Each resource provider [2702] may be connected to one or more computing device [2704a], [2704b], [2704c] (collectively, [2704]), over the computer network [2708].

The cloud computing environment [2700] may include a resource manager [2706]. The resource manager [2706] may be connected to the resource providers [2702] and the computing devices [2704] over the computer network [2708]. In some implementations, the resource manager [2706] may facilitate the provision of computing resources by one or more resource providers [2702] to one or more computing devices [2704]. The resource manager [2706] may receive a request for a computing resource from a particular computing device [2704]. The resource manager [2706] may identify one or more resource providers [2702] capable of providing the computing resource requested by the computing device [2704]. The resource manager [2706] may select a resource provider [2702] to provide the computing resource. The resource manager [2706] may facilitate a connection between the resource provider [2702] and a particular computing device [2704]. In some implementations, the resource manager [2706] may establish a connection between a particular resource provider [2702] and a particular computing device [2704]. In some implementations, the resource manager [2706] may redirect a particular computing device [2704] to a particular resource provider [2702] with the requested computing resource.

Remote, Mobile Computing Device

Figure 28:
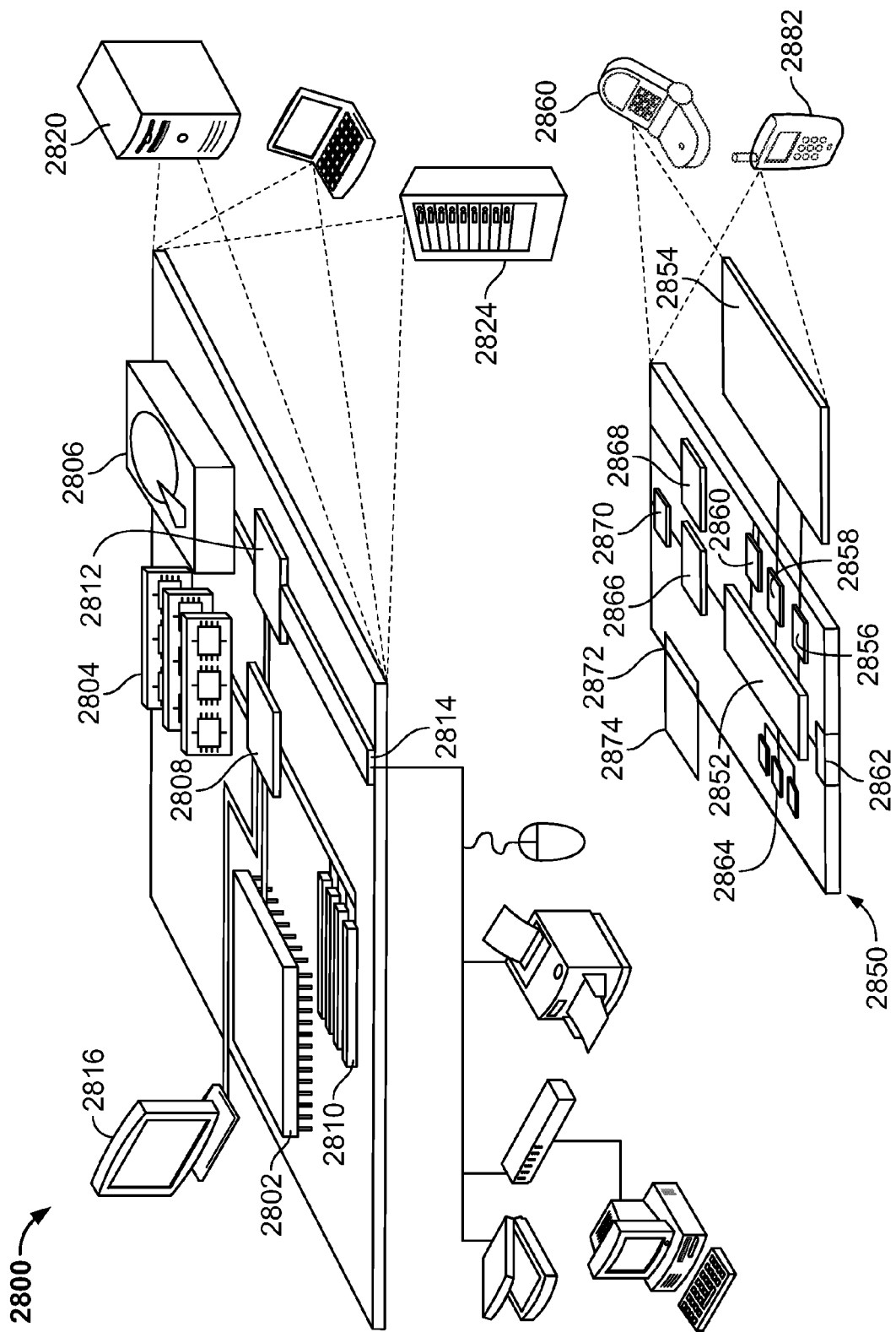
FIG. 28 is a block diagram of a computing device and a mobile computing device.

FIG. 28 shows an example of a computing device [2800] and a mobile computing device [2850] that can be used to implement the techniques described in this disclosure. The computing device [2800] is intended to represent various forms of digital computers, such as laptops, desktops, workstations, personal digital assistants, servers, blade servers, mainframes, and other appropriate computers. The mobile computing device [2850] is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device [2800] includes a processor [2802], a memory [2804], a storage device [2806], a high-speed interface [2808] connecting to the memory [2804] and multiple high-speed expansion ports [2810], and a low-speed interface [2812] connecting to a low-speed expansion port [2814] and the storage device [2806]. Each of the processor [2802], the memory [2804], the storage device [2806], the high-speed interface [2808], the high-speed expansion ports [2810], and the low-speed interface [2812], are interconnected using various busses, and may be mounted on a common motherboard or in other manners as appropriate. The processor [2802] can process instructions for execution within the computing device [2800], including instructions stored in the memory [2804] or on the storage device [2806] to display graphical information for a GUI on an external input/output device, such as a display [2816] coupled to the high-speed interface [2808]. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory [2804] stores information within the computing device [2800]. In some implementations, the memory [2804] is a volatile memory unit or units. In some implementations, the memory [2804] is a non-volatile memory unit or units. The memory [2804] may also be another form of computer-readable medium, such as a magnetic or optical disk.

The storage device [2806] is capable of providing mass storage for the computing device [2800]. In some implementations, the storage device [2806] may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor [2802]), perform one or more methods, such as those described above. The instructions can also be stored by one or more storage devices such as computer- or machine-readable mediums (for example, the memory [2804], the storage device [2806], or memory on the processor [2802]).

The high-speed interface [2808] manages bandwidth-intensive operations for the computing device [2800], while the low-speed interface [2812] manages lower bandwidth-intensive operations. Such allocation of functions is an example only. In some implementations, the high-speed interface [2808] is coupled to the memory [2804], the display [2816] (e.g., through a graphics processor or accelerator), and to the high-speed expansion ports [2810], which may accept various expansion cards (not shown). In the implementation, the low-speed interface [2812] is coupled to the storage device [2806] and the low-speed expansion port [2814]. The low-speed expansion port [2814], which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device [2800] may be implemented in a number of different forms, as shown in the figure. For example, it may be implemented as a standard server [2820], or multiple times in a group of such servers. In addition, it may be implemented in a personal computer such as a laptop computer [2822]. It may also be implemented as part of a rack server system [2824]. Alternatively, components from the computing device [2800] may be combined with other components in a mobile device (not shown), such as a mobile computing device [2850]. Each of such devices may contain one or more of the computing device [2800] and the mobile computing device [2850], and an entire system may be made up of multiple computing devices communicating with each other.

The mobile computing device [2850] includes a processor [2852], a memory [2864], an input/output device such as a display [2854], a communication interface [2866], and a transceiver [2868], among other components. The mobile computing device [2850] may also be provided with a storage device, such as a micro-drive or other device, to provide additional storage. Each of the processor [2852], the memory [2864], the display [2854], the communication interface [2866], and the transceiver [2868], are interconnected using various buses, and several of the components may be mounted on a common motherboard or in other manners as appropriate.

The processor [2852] can execute instructions within the mobile computing device [2850], including instructions stored in the memory [2864]. The processor [2852] may be implemented as a chipset of chips that include separate and multiple analog and digital processors. The processor [2852] may provide, for example, for coordination of the other components of the mobile computing device [2850], such as control of user interfaces, applications run by the mobile computing device [2850], and wireless communication by the mobile computing device [2850].

The processor [2852] may communicate with a user through a control interface [2858] and a display interface [2856] coupled to the display [2854]. The display [2854] may be, for example, a TFT (Thin-Film-Transistor Liquid Crystal Display) display or an OLED (Organic Light Emitting Diode) display, or other appropriate display technology. The display interface [2856] may comprise appropriate circuitry for driving the display [2854] to present graphical and other information to a user. The control interface [2858] may receive commands from a user and convert them for submission to the processor [2852]. In addition, an external interface [2862] may provide communication with the processor [2852], so as to enable near area communication of the mobile computing device [2850] with other devices. The external interface [2862] may provide, for example, for wired communication in some implementations, or for wireless communication in other implementations, and multiple interfaces may also be used.

The memory [2864] stores information within the mobile computing device [2850]. The memory [2864] can be implemented as one or more of a computer-readable medium or media, a volatile memory unit or units, or a non-volatile memory unit or units. An expansion memory [2874] may also be provided and connected to the mobile computing device [2850] through an expansion interface [2872], which may include, for example, a SIMM (Single In Line Memory Module) card interface. The expansion memory [2874] may provide extra storage space for the mobile computing device [2850], or may also store applications or other information for the mobile computing device [2850]. Specifically, the expansion memory [2874] may include instructions to carry out or supplement the processes described above, and may include secure information also. Thus, for example, the expansion memory [2874] may be provided as a security module for the mobile computing device [2850], and may be programmed with instructions that permit secure use of the mobile computing device [2850]. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor [2852]), perform one or more methods, such as those described above. The instructions can also be stored by one or more storage devices, such as one or more computer- or machine-readable mediums (for example, the memory [2864], the expansion memory [2874], or memory on the processor [2852]). In some implementations, the instructions can be received in a propagated signal, for example, over the transceiver [2868] or the external interface [2862].

The mobile computing device [2850] may communicate wirelessly through the communication interface [2866], which may include digital signal processing circuitry where necessary. The communication interface [2866] may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver [2868] using a radio-frequency. In addition, short-range communication may occur, such as using a Bluetooth®, Wi-Fi™, or other such transceiver (not shown). In addition, a GPS (Global Positioning System) receiver module [2870] may provide additional navigation- and location-related wireless data to the mobile computing device [2850], which may be used as appropriate by applications running on the mobile computing device [2850].

The mobile computing device [2850] may also communicate audibly using an audio codec [2860], which may receive spoken information from a user and convert it to usable digital information. The audio codec [2860] may likewise generate audible sound for a user, such as through a speaker, e.g., in a handset of the mobile computing device [2850]. Such sound may include sound from voice telephone calls, may include recorded sound (e.g., voice messages, music files, etc.) and may also include sound generated by applications operating on the mobile computing device [2850].

The mobile computing device [2850] may be implemented in a number of different forms, as shown in the figure. For example, it may be implemented as a cellular telephone [2880]. It may also be implemented as part of a smart-phone [2882], personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for data collection are provided. Having described certain implementations of methods and apparatus for supporting remote data collection, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

EXEMPLIFICATION

Referring to FIG. 10, an exemplary logic workflow diagram for on-site testing of carpet, carpet pad, rugs, and ceramic tile in accordance with methods of the present disclosure is shown. A user with a remote, mobile communications device logs into the app. The user and the app are oriented through the general identification menu. Herein, the user identifies the material, for example, carpet. The user may also identify other informational criteria, such as billing information, address, etc. For a carpet sample the next step in the workflow of FIG. 10 requires the user take a whole room photo of the carpet. For the next input in the workflow of FIG. 10 the user is asked to take a Top Down photo of the carpet.

A user may know the fiber type and/or have fiber documentation. For such an instance, the next display screen is a conditional point. This point allows the user to indicate whether the fiber type is known. If the response is no, then the next display screen prompts the user for entry of a plurality of measurements, other data, and/or and photos, for the carpet and backing, for example, including sides, top, backing and/or or close up photos thereof. If the response is yes, the next display screen prompts the user to input the fiber type and upload a photograph of any documentation. In some embodiments, a data entry display may appear allowing a user to confirm carpet fiber specifications. Additionally, in some embodiments, the user may be able to change or adjust parameters on the fiber documentation data display to further customize and/or match the fiber specifications to the fiber documentation. Following entry of any known data, the user display screen prompts the user to input various measurements, other data, and/or photos for the carpet and backing.

After entry of all corresponding data for the carpet, the user is provided to option to provide user input with respect to a carpet pad. If there is no carpet pad, then the user is prompted to submit the user input for the carpet. If there is a carpet pad, the next display screen prompts the user for user input with respect to the carpet pad in the pad workflow. In some embodiments, user input with respect to a carpet pad may include, for example, any known information about the manufacture or make of the carpet pad. User input may also include data, measurements, and/or photos, for example, including top, bottom, and thickness (height). Upon completion of the carpet pad workflow and collecting of all user input for the carpet pad, the user is prompted to submit the user input for both the carpet and the carpet pad.

The workflow illustrated in FIG. 16 shows an exemplary logic workflow diagram for shipping a physical sample to the lab for testing and analysis in accordance with some embodiments of the present disclosure. This shipping workflow prompts entry of user input including biographical information, such as, company name, billing information, and address. The next step in the workflow asks the user for user input to identify the building material product sample being shipped to the lab. In some embodiments, the user input can be a description. In some embodiments, the user input may be a photo. As there are different carriers and different methods of shipping, the user is prompted to input special instructions for the carrier. Before submitting, the user may provide tracking input to associate the shipment with the entry of user input acquired by the user during the onsite evaluation. For example, the user may enter a tracking number or the device reads the barcode and transmits the code corresponding with the information, data, and photos acquired during the evaluation. Upon receipt, the service provider can utilize the user input information, data, and photos and correlate those inputs with any data acquired from the physical sample during lab tests. Ultimately, the collective of information can arm an analyst with information to match a sample for value or like, kind, and quality.

OTHER EMBODIMENTS AND EQUIVALENTS

While the present disclosure has explicitly discussed certain particular embodiments and examples of the present disclosure, those skilled in the art will appreciate or be able to ascertain using no more than routine experimentation that the invention is not intended to be limited to such embodiments or examples. On the contrary, the present disclosure encompasses various alternatives, modifications, and equivalents of such particular embodiments and/or example, as will be appreciated by those of skill in the art.

To give but a few examples, methods and diagrams of should not be read as limited to a particular described order or arrangement of steps or elements unless explicitly stated or clearly required from context (e.g., otherwise inoperable). Furthermore, different features of particular elements that may be exemplified in different embodiments may be combined with one another in some embodiments.

The scope of the present disclosure is not intended to be limited to the above description, but rather is as set forth in the following claims.

What is claimed:

1. A method for on-site assignment of value and/or for on-site assessment of like kind and quality, the method comprising:
    providing, for access by a remote, mobile client computing device, an interactive program configured to enable collection of data from the remote client computing device for the assignment of value and/or the assessment of like kind and quality, wherein the interactive program is configured to display to a user a sequence of screens on the remote computing device prompting entry of user input about a building material sample;
    receiving, by a processor of a service provider computing device, over a network, from the remote computing device, user input about the building material sample; and
    transmitting, by the processor of the service provider computing device, to the remote client computing device, results of an analysis for the assignment of value and/or the assessment of like kind and quality, for display to the user,
    wherein the user input comprises at least one photo of the building material sample, and
    wherein the sequence of screens prompting entry of user input comprises one or more graphical prompts instructing the user in acquiring the at least one photo of the building material sample using the remote, mobile client computing device, wherein the one or more graphical prompts comprises one or more members selected from the group consisting of: a photographic prompt, a schematic prompt, and a pictorial prompt, and
    wherein the user input comprises at least one piece of information indicative of the building material sample, wherein the at least one piece of information indicative of the building material sample comprises one or more members selected from the group consisting of: an identification of a user, an identification of a site, an identification of a sample number, and a characteristic corresponding to the building material sample, and
    wherein the characteristic corresponding to the building material sample is a measurement of the building material sample, a type of material of the building material sample, or combinations thereof, and further wherein the type of material of the building material sample comprises one or more members selected from the group consisting of: carpet, wood, vinyl, laminate, tile, siding, roofing, rug, or combinations thereof.

2. The method of claim 1, wherein the interactive program is further configured to manipulate the at least one photo of the sample before the receiving step when the user accesses a prompt displayed on at least one screen for photo management, a prompt for the user to acquire additional photos for the user input before the receiving step, and/or a prompt for the user to delete the at least one photo from the user input before the receiving step.

3. The method of claim 1, wherein entry of the at least one piece of information indicative of the sample comprises one or more members selected from the group consisting of: follows one or more prompts displayed on at least one screen presented based on responses provided by the user on one or more preceding screens and ensues from a selection by the user from a dynamic list displayed on the remote computing device, and further wherein the dynamic list is displayed as one or more members selected from the group consisting of: a text box, a dropdown list box, or a radio button.

4. The method of claim 1, wherein the providing step further comprises identifying whether all required data about the building material sample has been entered by the user before the receiving step and, if it is determined that there is missing data, prompt the user to enter the missing data.

5. The method of claim 1, wherein the interactive program is further configured to identify an incorrect entry of user input about the building material sample and prompt the user to correct the incorrect entry.

6. The method of claim 1, wherein the interactive program is further configured to store user input when the remote, mobile computing device is offline.

7. The method of claim 1, wherein the interactive program is further configured to connect the user to an offsite analyst.

8. The method of claim 7, wherein entry of user input is substantially concurrent with the connection to the offsite analyst.

9. The method of claim 7, wherein the interactive program is configured to display queries by the offsite analyst regarding the building material sample and/or the user input.

10. The method of claim 9, wherein the query is a prompt to supply missing data and/or a prompt to correct erroneous data.

11. The method of claim 1, wherein the providing step further comprises transmitting, by the processor of the service provider computing device, to the remote client computing device, a prompt for the user to provide a response to a query posed by an offsite analyst.

12. The method of claim 1, wherein the results of the analysis are transmitted to the client computing device within about 5 hours of receipt of the user input, thereby allowing on-site completion of the assignment of value and/or the assessment of like kind and quality.

13. The method of claim 1, wherein the interactive program is further configured to display an application help system and/or associate the user input with a physical sample of the building material sample sent by the user to a lab.

* * * * *